(12) United States Patent
Moore et al.

(10) Patent No.: US 8,865,684 B2
(45) Date of Patent: Oct. 21, 2014

(54) MORPHOLIN-4-IUM 4 METHOXYPHENYL (MORPHOLINO) PHOSPHINODITHIOATE (GYY4137) AS A NOVEL VASODILATOR AGENT

(71) Applicant: National University of Singapore, Singapore (SG)

(72) Inventors: Philip Keith Moore, Singapore (SG); Choon-Hong Tan, Singapore (SG); Ling Li, Singapore (SG); Yan Yi Guan, Singapore (SG)

(73) Assignee: National University of Singapore, Singapore (SG)

( * ) Notice: Subject to any disclaimer, the term of this patent is extended or adjusted under 35 U.S.C. 154(b) by 0 days.

(21) Appl. No.: 13/967,527

(22) Filed: Aug. 15, 2013

(65) Prior Publication Data
US 2013/0331360 A1 Dec. 12, 2013

Related U.S. Application Data

(62) Division of application No. 12/429,661, filed on Apr. 24, 2009, now Pat. No. 8,541,396.

(51) Int. Cl.
*A61K 31/675* (2006.01)
*A61K 31/662* (2006.01)
*A61K 31/66* (2006.01)

(52) U.S. Cl.
CPC .............. *A61K 31/675* (2013.01); *A61K 31/662* (2013.01); *A61K 31/66* (2013.01); *Y10S 514/885* (2013.01); *Y10S 514/957* (2013.01)
USPC .............................. 514/90; 514/885; 514/957

(58) Field of Classification Search
CPC .............. A61K 31/675; Y10S 514/885; Y10S 514/957
See application file for complete search history.

(56) References Cited

U.S. PATENT DOCUMENTS

| | | | |
|---|---|---|---|
| 2,954,379 | A | 9/1960 | Hook et al. |
| 7,928,067 | B2 | 4/2011 | Baguisi et al. |
| 8,541,396 | B2 * | 9/2013 | Moore et al. |
| 2006/0270635 | A1 | 11/2006 | Wallace et al. |
| 2007/0265223 | A1 | 11/2007 | Tomaselli et al. |
| 2009/0214673 | A1 | 8/2009 | Ohia et al. |
| 2009/0306412 | A1 | 12/2009 | Wallace et al. |
| 2010/0143503 | A1 | 6/2010 | Szabo et al. |
| 2010/0247680 | A1 | 9/2010 | Szabo |
| 2010/0273743 | A1 | 10/2010 | Moore et al. |
| 2013/0064904 | A1 | 3/2013 | Gojon-Romanillos et al. |

FOREIGN PATENT DOCUMENTS

| | | |
|---|---|---|
| CN | 101928240 A | 12/2010 |
| CN | 102552235 A | 7/2012 |
| JP | H 0225478 A | 1/1990 |
| RU | 2406477 C1 | 12/2010 |
| WO | WO 2006/102536 A2 | 9/2006 |
| WO | WO 2008/043081 A2 | 4/2008 |
| WO | WO 2008/070741 A1 | 6/2008 |
| WO | WO 2012/067947 A1 | 5/2012 |
| WO | WO 2012/075242 A2 | 6/2012 |
| WO | WO 2012/075244 A2 | 6/2012 |
| WO | WO 2012/154126 A1 | 11/2012 |
| WO | WO 2013/045951 A1 | 4/2013 |

OTHER PUBLICATIONS

Li et al., Circulation, 2008 (available online Apr. 28, 2008), vol. 117, pp. 2351-2360.*

Emory University (ScienceDaily, Nov. 13, 2008, "Treating Heart Failure With a Gas", Retrieved Dec. 9, 2013, from http://www.sciencedaily.com/releases/2008/11/081111112059.htm).*

Ali, M., et al., "Regulation of Vascular Nitric Oxide In Vitro and In Vivo; A New Role for Endogenous Hydrogen Sulphide?," *British Journal of Pharmacology*, 149:625-634 (2006).

Ashraf, M.Z., et al., "Endothelium Medicated Vasorelaxant Response of Garlic in Isolated Rat Aorta: Role of Nitric Oxide," *Journal of Ethnopharmacology*, 90:5-9 (2004).

Baskar, R., et al., "Hydrogen Sulfide-Induces DNA Damage and Changes in Apoptotic Gene Expression in Human Lung Fibroblast Cells," *The FASEB Journal*, 21:247-255 (2007).

Benavides, G.A., et al., "Hydrogen Sulfide Mediates the Vasoactivity of Garlic," *PNAS*, 104(46):17977-17982 (2007).

Berkenboom, G., et al., "Endothelium-Dependent Effects of Pentoxifylline in Rat Aorta," *European Journal of Pharmacology*, 193:81-86 (1991).

Berkhart, E.M., et al., "Role of Stat3 in Lipopolysaccharide-Induced IL-10 Gene Expression," *The Journal of Immunology*, 165:1612-1617 (2000).

Bhatia, M., et al., "Hydrogen Sulphide is a Mediator of Carrageenan-Induced Hindpaw Oedema in the Rat," *British Journal of Pharmacology*, 145:141-144 (2005).

Bhatia, M., et al., "Role of Hydrogen Sulfide in Acute Pancreatitis and Associated Lung Injury," *FASEB J.*, 19(6):623-625 (2005).

(Continued)

*Primary Examiner* — Savitha Rao
*Assistant Examiner* — Gregg Polansky
(74) *Attorney, Agent, or Firm* — Hamilton, Brook, Smith & Reynolds, P.C.

(57) ABSTRACT

The invention is directed to a method of administering hydrogen sulfide ($H_2S$) slowly and sustainably to an individual in need thereof comprising administering an effective amount of a compound represented by the following structural formula:

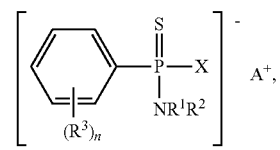

or a pharmaceutically acceptable salt thereof.

1 Claim, 20 Drawing Sheets

(56) References Cited

OTHER PUBLICATIONS

Blackwell, T.S., et al., "Multiorgan Nuclear Factor Kappa B Activation in a Transgenic Mouse Model of Systemic Inflammation," *Am J Respir Crit Care Med*, 162:1095-1101 (2000).
Ceron, P., et al., "The Relaxation Induced by S-Nitroso-Glutathione and S-Nitroso-N-Acetylcysteine in Rat Aorta Is Not Related to Nitric Oxide Production," *The Journal of Pharmacology and Experimental Therapeutics*, 298(2):686-694 (2001).
Chen, Y-H., et al., "Endogenous Hydrogen Sulfide Reduces Airway Inflammation and Remodeling in a Rat Model of Asthma," *Cytokine*, 45:117-123 (2009).
Cheng, Y., et al., "Hydrogen Sulfide-Induced Relaxation of Resistance Mesenteric Artery Beds of Rats," *Am J Physiol Heart Circ Physiol*, 287:H2316-H2323 (2004).
Chunyu, Z., et al., "The Regulatory Effect of Hydrogen Sulfide on Hypoxic Pulmonary Hypertension in Rats," *Biochemical and Biophysical Research Communications*, 302:810-816 (2003).
Collin, M., et al., "Inhibition of Endogenous Hydrogen Sulfide Formation Reduces the Organ Injury Caused by Endotoxemia," *British Journal of Pharmacology*, 146:498-505 (2005).
Collin, M., et al., "Reduction of the Multiple Organ Injury and Dysfunction Caused by Endotoxemia in 5-Lipoxygenase Knockout Mice and by the 5-Lipoxygenase Inhibitor Zileuton," *Journal of Leukocyte Biology*, 76:961-970 (2004).
d'Emmanuele di Villa Bianca, R., et al., "Hydrogen Sulfide as a Mediator of Human Corpus Cavernosum Smooth-Muscle Relaxation," *PNAS*, 016(11):4513-4518, Mar. 17, 2009.
Dal-Secco, D., et al., "Hydrogen Sulfide Augments Neutrophil Migration through Enhancement of Adhesion Molecule Expression and Prevention of CXCR2 Internalization: Role of ATP-Sensitive Potassium Channels," *The Journal of Immunology*, 181:4287-4298 (2008).
Distrutti, E., et al., "Evidence That Hydrogen Sulfide Exerts Antinociceptive Effects in the Gastrointestinal Tract by Activating $K_{ATP}$ Channels," *J Pharmacol Exp Ther*, 316:325-335 (2006).
Feelisch, M., et al., "The Soluble Guanylyl Cyclase Inhibitor 1H-[1,2,4]Oxadiazolo-[4,3,-a]quinoxalin- 1-one is a Nonselective Heme Protein Inhibitor of Nitric Oxide Synthase and Other Cytochrome P-450 Enzymes Involved in Nitric Oxide Donor Bioactivation," *Molecular Pharmacology*, 56:243-253 (1999).
Feng, X., et al., "Hydrogen Sulfide from Adipose Tissue is a Novel Insulin Resistance Regulator," *Biochemical and Biophysical Research Communications*, 380:153-159 (2009).
Fiorucci, S., et al., "Enhanced Activity of a Hydrogen Sulphide-Releasing Derivative of Mesalamine (ATB-429) in a Mouse Model of Colitis," *British Journal of Pharmacology*, 150:996-1002 (2007).
Fiorucci, S., et al., "Inhibition of Hydrogen Sulfide Generation Contributes to Gastric Injury Caused by Anti-Inflammatory Nonsteroidal Drugs," *Gastroenterology*, 129:1210-1224 (2005).
Florian, B., et al., "Long-Term Hypothermia Reduces Infarct Volume in Aged Rats After Focal Ischemia," *Neuroscience Letters*, 438:180-185 (2008).
Geng, B., et al., "$H_2S$ Generated by Heart in Rat and Its Effects on Cardiac Function," *Biochemical and Biophysical Research Communications*, 313:362-368 (2004).
Geng, B., et al., "Hydrogen Sulfide Downregulates the Aortic L-arginine/nitric oxide pathway in Rats," *Am J Physiol Regul Integr Comp Physiol*, 293:R1608-R1618 (2007).
Ikegami, M., et al., "STAT-3 Regulates Surfactant Phospholipid Homeostatis in Normal Lung and During Endotoxin-Mediated Lung Injury," *J Appl Physiol*, 104:1753-1760 (2008).
Janciauskiene, S.M., et al., "$\alpha_1$-Antitrypsin, Old Dog, New Tricks," *The Journal of Biological Chemistry*, 282(12):8573-8582 (2007).
Janssen-Heininger, Y.M.W., et al., "Recent Advances Towards Understanding Redox Mechanisms in the Activation of Nuclear Factor κB," *Free Radical Biology & Medicine*, 28(9):1317-1327 (2000).
Jeney, V., et al., "Supression of Hemin-Mediated Oxidation of Low-Density Lipoprotein and Subsequent Endothelial Reactions by Hydrogen Sulfide ($H_2S$)," *Free Radical Biology & Medicine*, 46616-623 (2009).
Kamoun, P., "Endogenous Production of Hydrogen Sulfide in Mammals," *Amino Acids*, 26:243-254 (2004).
Kaneko, Y., et al., "Glucose-Induced Production of Hydrogen Sulfide May Protect the Pancreatic Beta-Cells from Apoptotic Cell Death by High Glucose," *FEBS Letters*, 583:377-382 (2009).
Kang, J.L., et al., "Inhaled Nitric Oxide Attenuates Acute Lung Injury Via Inhibition of Nuclear Factor-κB and Inflammation," *J Appl Physiol*, 92:795-801 (2002).
Kawabata, A., et al., "Hydrogen Sulfide as a Novel Nociceptive Messenger," *Pain*, 132:74-81 (2007).
Kiss, L., et al., "Hydrogen Sulfide Decreases Adenosine Triphosphate Levels in Aortic Rings and Leads to Vasorelaxation via Metabolic Inhibition," *Life Sciences*, 83:589-594 (2008).
Koenitzer, J.R., et al., "Hydrogen Sulfide Mediates Vasoactivity in an $O_2$-Dependent Manner," *Am J Physiol Heart Circ Physiol*, 292:H1953-H1960 (2007).
Kubo, S., et al., "Direct Inhibition of Endothelial Nitric Oxide Synthase by Hydrogen Sulfide: Contribution to Dual Modulation of Vascular Tension," *Toxicology*, 232:138-146 (2007).
Kulkarni, K.H., et al., "Effect of Hydrogen Sulfide on Sympathetic Neurotransmission and Catecholamine Levels in Isolated Procine Iris-Ciliary Body," *Neurochem. Res.*, 34:400-406 (2009).
Labarca, C. and Paigen, K., "A Simple, Rapid, and Sensitive DNA Assay Procedure," *Analytical Biochemistry*, 102:344-352 (1980).
Lee, S.W., et al., "Hydrogen Sulphide Regulates Intracellular pH in Vascular Smooth Muscle Cells," *Biochemical and Biophysical Research Communications*, 358:1142-1147 (2007).
Leschelle, X., et al., "Adaptative Metabolic Response of Human Colonic Epithelial Cells to the Adverse Effects of the Luminal Compound Sulfide," *Biochimica et Biophysica Acta*, 1725:201-212 (2005).
Li, L. and Moore, P.K., "Putative Biological Roles of Hydrogen Sulfide in Health and Disease: A Breath of Not so Fresh Air?," *Trends in Pharmacological Sciences*, 29(2):84-90 (2007).
Li, L., et al., "Anti-Inflammatory and Gastrointestinal Effects of a Novel Diclofenac Derivative," *Free Radical Biology & Medicine*, 42:706-719 (2007).
Li, L., et al., "Characterization of a Novel, Water-Soluble Hydrogen Sulfide-Releasing Molecule (GYY4137) New Insights into the Biology of Hydrogen Sulfide," *Circulation*, pp. 2351-2360, May 6, 2008.
Li, L., et al., "Hydrogen Sulfide is a Novel Mediator of Lipopolysaccaride-Induced Inflammation in the Mouse," *FASEB J.*, 19(9):1196-1198 (2005).
Li, X., et al., "Endogenous Hydrogen Sulfide Regulates Pulmonary Artery Collagen Remodeling in Rats with High Pulmonary Blood Flow," *Society for Experimental Biology and Medicine*, pp. 504-512 (2009).
Li, X., et al., "The Regulatory Effect of Endogenous Hydrogen Sulfide on Pulmonary Vascular Structure and Gasotransmitters in Rats with High Pulmonary Blood Flow," *Life Sciences*, 81:841-849 (2007).
Liu, H., et al., "Hydrogen Sulfide Protects from Intestinal Ischaemia-Reperfusion Injury in Rats," *Journal of Pharmacy and Pharmacology*, 61:207-212 (2009).
Marshall, M. and Moore, P.K., "Effect of Nitric Oxide Releasing Paracetamol and Flurbiprofen on Cytokine Production in Human Blood," *European Journal of Pharmacology*, 483:317-322 (2004).
Mok, Y-Y, et al., "Role of Hydrogen Sulphide in Haemorrhagic Shock in the Rat: Protective Effect of Inhibitors of Hydrogen Sulphide Biosynthesis," *British Journal of Pharmacology*, 143:881-889 (2004).
Monjok, E.M., et al., "Inhibitory Action of Hydrogen Sulfide on Muscarinic Receptor-Induced Contraction of Isolated Porcine Irides," *Experimental Eye Research*, 87612-616 (2008).
Moore, P.K., et al., "Hydroxylamine Dilates Resistance Blood Vessels of the Perfused Rat Kidney and Mesentery," *J. Pharm. Pharmacol.*, 41:426-429 (1988).
Muellner, M.K., et al., "Hydrogen Sulfide Destroys Lipid Hydroperoxides in Oxidized LDL," *Biochemical Journal Immediate Publication*, Published on Mar. 5, 2009 as Manuscript BJ20082421.

(56) References Cited

OTHER PUBLICATIONS

Muzaffar, S., et al., "Exogenous Hydrogen Sulfide Inhibits Superoxide Formation, NOX-1 Expression and Rac$_1$ Activity in Human Vascular Smooth Muscle Cells," *J. Vasc. Res.*, 45:521-528 (2008).

Muzaffar, S., et al., "H$_2$S-Donating Sildenafil (ACS6) Inhibits Superoxide Formation and gp91$^{phox}$ Expression in Arterial Endothelial Cells: Role of Protein Kinases A and G," *British Journal of Pharmacology*, 155:984-994 (2008).

Nicholls, P. and Kim, J-K, "Sulphide as an Inhibitor and Electron Donor for the Cytochrome C Oxidase System," *Can. J. Biochem.*, 60:613-623 (1982).

O'Sullivan, SE, "What is the Significance of Vascular Hydrogen Sulphide (H$_2$S)?," *British Journal of Pharmacology*, 149:609-610 (2006).

Oh, G-S., et al., "Hydrogen Sulfide Inhibits Nitric Oxide Production and Nuclear Factor-κb Via Heme Oxygenase-1 Expression in RAW264.7 Macrophages Stimulated with Lipopolysaccharide," *Free Radical Biology & Medicine*, 41:106-119 (2006).

Olson, K.R., et al., "Hydrogen Sulfide as an Oxygen Sensor/Transducer in Vertebrate Hypoxic Vasoconstriction and Hypoxic Vasodilation," *The Journal of Experimental Biology*, 209:4011-4023 (2006).

Pérez-Vizcaino, F., et al., "Vasodilator Effects of Sodium Nitroprusside, Levcromakalim and their Combination in Isolated Rat Aorta," *British Journal of Pharmacology*, 128:1419-1426 (1999).

Qingyou, Z., et al., "Impact of Hydrogen Sulfide on Carbon Monoxide/Heme Oxygenase Pathway in the Pathogenesis of Hypoxic Pulmonary Hypertension," *Biochemical and Biophysical Research Communications*, 317:30-37 (2004).

Wu, R., et al., "The Regulatory Effect of Endogenous Hydrogen Sulfide on Acute Asthma," *Chin J. Tuberc Respir Dis.*, 30(7):522-526 (2007). Abstract Only.

Shukla, N., et al., "Effect of Hydrogen Sulphide-Donating Sildenafil (ACS6) on Erectile Function and Oxidative Stress in Rabbit Isolated Corpus Cavernosum and in Hypertensive Rats," *BJU International*, pp. 1-8 (2009).

Simmonds, R.E. and Foxwell, B.M., "Signalling, Inflammation and Arthritis NF-κB and its Relevance to Arthritis and Inflammation," *Rheumatology*, 47:584-590 (2008).

Simon, F., et al., "Hemodynamic and Metabolic Effects of Hydrogen Sulfide During Procine Ischemia/Reperfusion Injury," *Shock*, 30(4):359-364 (2008).

Srilatha, B., MD, PhD., et al., "Hydrogen Sulphide: A Novel Endogenous Gasotransmitter Facilitates Erectile Function," *J. Sex Med.*, 4:1304-1311 (2007).

Stipanuk, M.H., "Sulfur Amino Acid Metabolism: Pathways for Production and Removal of Homocysteine and Cysteine," *Annu. Rev. Nutr.*, 24:539-577 (2004).

Szabó, C., "Hydrogen Sulphide and Its Therapeutic Potential," *Nature Reviews*, 6:917-935 (2007).

Tripatara, P., et al., "Generation of Endogenous Hydrogen Sulfide by Cystathionine γ-lyase Limits Renal Ischemia/Reperfusion Injury and Dysfunction," *Laboratory Investigation*, 88:1038-1048 (2008).

Trzeciak, S., et al., "Early Increases in Microcirculatory Perfusion During Protocol-Directed Resuscitation are Associated with Reduced Multi-Organ Failure at 24 h in Patients with Sepsis," *Intensive Care Med.*, 34:2210-2217 (2008).

Wallace, J.L., et al., "Gastrointestinal Safety and Anti-Inflammatory Effects of a Hydrogen Sulfide-Releasing Diclofenac Derivative in the Rat," *Gastroenterology*, 132:261-271 (2007).

Wallace, J.L:, "Hydrogen Sulfide-Releasing Anti-Inflammatory Drugs," *Trends in Pharmacological Sciences*, 28(10):501-505 (2007).

Wellman, G.C., et al., "Inhibition of Vascular K$_{ATP}$ Channels by U-37883A: A Comparison with Cardiac and Skeletal Muscle," *British Journal of Pharmacology*, 128:909-916 (1999).

Su, Y-W., et al., "Hydrogen Sulfide Regulates Cardiac Function and Structure in Adriamycin-Induced Cardiomyopathy," *Circulation Journal*, 73:741-749 (2009).

Whiteman, M., et al., "Hydrogen Sulfide Regulates the Availability of Nitric Oxide through the Formation of a Novel Nitrosothiol: Implications for Cardiovascular Function and Human Disease," *Posters/Nitric Oxide*, 14:A39-A44, Abstract P073 on p. A40 (2006).

Whiteman, M., et al., "The Novel Neuromodulator Hydrogen Sulfide: An endogenous Peroxynitrite 'Scavenger'?," *Journal of Neurochemistry*, 90:765-768 (2004).

Wu, L., et al., "Pancreatic Islet Overproduction of H$_2$S and Suppressed Insulin Release in Zucker Diabetic Rats," *Laboratory Investigation*, 89:59-67 (2009).

Xia, M., et al., "Production and Actions of Hydrogen Sulfide, a Novel Gaseous Bioactive Substance, in the Kidneys," *American Society for Pharmacology and Experimental Therapeutics*, pp. 1-28 (2009).

Xiao, X-H and Allen, D.G., "Role of Na$^+$/H$^+$ Exchanger During Ischemia and Preconditioning in the Isolated Rat Heart," *Circulation Research*, 85:723-730 (1999).

Li, X-H., et al., "Impact of Hydrogen Sulfide Donor on Experimental Pulmonary Hypertension Induced by High Pulmonary Flow and Endogenous Carbon Monoxide/Heme Oxygenase Pathway," *Journal of Peking University (Health Sciences)*, 38(2):135-139 (2006). Abstract Only.

Li, X-H., et al., "Impact of Hydrogen Sulfide Donor on Pulmonary Vascular Structure and Vasoactive Peptides in Rats with Pulmonary Hypertension Induced by High Pulmonary Blood Flow," *Acta Academiae Medicinae Sinicae*, 28(2):159-163 (2006). Abstract Only.

Li, X-H., et al., "Mechanism by Which Hydrogen Sulfide Regulates Pulmonary Vascular Structural Remodeling Induced by High Pulmonary Blood Flow in Rats," *Chin. J. Pediatr.*, 44(12):941-945 (2006). Abstract Only.

Li, X-H., "Sodium Hydrosulfide Alleviates Pulmonary Artery Collagen Remodeling in Rats with High Pulmonary Blood Flow," *Heart Vessels*, 23:409-419 (2008).

Li, X-H., et al., "Sodium Hydrosulfide Alleviated Pulmonary Vascular Structural Remodeling Induced by High Pulmonary Blood Flow in Rats," *Acta Pharmacologica Sinica*, 27(8):971-980 (2006).

Yan, H., et al., "The Possible Role of Hydrogen Sulfide on the Pathogenesis of Spontaneous Hypertension in Rats," *Biochemical and Biophysical Research Communications*, 313:22-27 (2004).

Yang, G., et al., "H$_2$S as a Physiologic Vasorelaxant: Hypertension in Mice with Deletion of Cystathionine γ-Lyase," *Science*, 322:587-590 (2008).

Yang, G., et al., "Hydrogen Sulfide-Induced Apoptosis of Human Aorta Smooth Muscle Cells Via the Activation of Mitogen-Activated Protein Kinases and Caspase-3," *FASEB J.*, 18(14):1782-1784 (2004).

Yang, W., et al., "Activation of K$_{ATP}$ Channels by H$_2$S in Rat Insulin-Secreting Cells and the Underlying Mechanisms," *J. Physiol.* 569. 2:519-531 (2005).

Yusof, M., et al., "Hydrogen Sulfide Triggers Late-Phase Preconditioning in Postischemic Small Intestine by an NO- and p38 MAPK-dependent Mechansim," *Am. J. Physiol. Heart Circ. Physiol.*, 296:H868-H876 (2009).

Yusuf, M., et al., "Streptozotocin-Induced Diabetes in the Rat is Associated with Enhanced Tissue Hydrogen Sulfide Biosynthesis," *Biochemical and Biophysical Research Communications*, 333:1146-1152 (2005).

Zanardo, R.C.O., et al., "Hydrogen Sulfide is an Endogenous Modulator of Leukocyte Mediated Inflammation," *the FASEB Journal*, 20:2118-2128 (partial article), pp. E1411-E1418 (full article) (2006).

Zhang, H., et al., "Endogenous Hydrogen Sulfide Regulates Leukocyte Trafficking in Cecal Ligation and Puncture-Induced Sepsis," *Journal of Leukocyte Biology*, 82:894-905 (2007).

Zhao, W. and Wang, R., "H$_2$S-Induced Vasorelaxation and Underlying Cellular and Molecular Mechanisms," *Am J Physiol Heart Circ Physiol*, 283:H474-H480 (2002).

Zhao, W., et al., "The Vasorelaxant Effect of H$_2$S as a Novel Endogenous Gaseous K$_{ATP}$ Channel Opener," *The EMBO Journal*, 20(21):6008-6016 (2001).

Zhi, L., et al., "Hydrogen Sulfide Induces the Synthesis of Proinflammatory Cytokines in Human Monocyte Cell Line U937 Via the ERK-NF-κB Pathway," *Journal of Leukocyte Biology*, 81:1322-1332 (2007).

(56) References Cited

OTHER PUBLICATIONS

Zhu, Y.Z., et al., "Hydrogen Sulfide and its Possible Roles in Myocardial Ischemia in Experimental Rats," *J Appl Physiol*, 102:261-268 (2007).

* Non-published U.S. Appl. No. 60/936,578, filed Jun. 21, 2007, entitled "Identification of Morpholin-4-IUM 4 Methoxyphenyl (Morpholino) Phosphinodithioate (GYY4137) as a Novel Vasodilator Agent."

Li, L., et al., "GYY4137, a Novel Hydrogen Sulfide-Releasing Molecule, Protects Against Endotoxic Shock in the Rat", *Free Radical Biology & Medicine*, (47) 103-113 (2009).

Wu, R., et al., "The Regulatory Effect of Endogenous Hydrogen Sulfide on Acute Asthma", *Chin. J. Tubero Respir. Dis.*, 30(7) 522-6 (2007).

Yu, F., et al., "Effect of synthesized GYY4137, a Slowly Releasing Hydrogen Sulfide Donor, on Cell Viability and Distribution of Hydrogen Sulfide in Mice", *Journal of Peking University (Health Sciences)*, 42(5):493-497 (2010).

Whiteman, M., et al., "The Effect of Hydrogen Sulfide Donors on Lipopolysaccharide-Induced Formation of Inflammatory Mediators in Macrophages", *Antioxidants & Redox Signaling*, 12(10):1147-1154 (2010).

Beltkowski, J., et al., Hydrogen Sulfide and its Modulation in Arterial Hypertension and Atherosclerosis. [Article] *Cardiovascular & Hematological Agents in Medicinal Chemistry*. 8(4):173-186, 2010.

Gan, XB, et al., "Hydrogen sulfide in paraventricular nucleus enhances sympathetic activity and cardiac sympathetic afferent reflex in chronic heart failure rats." *PLOS ONE*, 7(11):e50102, Nov. 2012.

Liu, YH, et al., "Hydrogen sulfide in the mammalian cardiovascular system," *Antioxidants & Redox Signaling*. Jul. 1, 2012, 17(1): 141-185. doi:10.1089/ars.2011.4005.

Kashfi, K. and Olson, K.R., "Biology and therapeutic potential of hydrogen sulfide and hydrogen sulfide-releasing chimeras," *Biochem. Pharmacol.* Mar. 1, 2013: 85(5): 689-703. doi:10.1016/j.bcp.2012.10.019.

Esechi, A., et al., "Beneficial effect of a hydrogen sulphide donor (sodium sulphide) in an ovine model of burn- and smoke-induced acute lung injury," *British Journal of Pharmacology* (2009), 158, 1442-1453.

Grambow, E., et al., "Effect of the hydrogen sulfide donor GYY4137 on platelet activation and microvascular thrombus formation in mice," *Platelets* [online], 2013 [retrieved on Apr. 8, 2014]. Retrieved from the Internet URL: http://informahealthcare.com/plt.

Dellavalle, B., et al., "Investigation of Hydrogen Sulfide Gas as a Treatment against *P. falciparum*, Murine Cerebral Malaria, and the Importance of Thiolation State in the Development of Cerebral Malaria." *PLOS One*, Mar. 2013, 8(3) e59271.

Miller L.W. and Missov E.D., "Epidemiology of heart failure." *Cardiol Clin*. Nov. 2001;19(4):547-55. PubMed PMID: 11715176. Epub Nov. 22, 2001.

Lloyd-Jones D., et al., "Heart disease and stroke statistics—2010 update: a report from the American Heart Association." *Circulation*. Feb. 23, 2010;121(7):e46-e215. PubMed PMID: 20019324. Epub Dec. 19, 2009.

Li L, et al., "Hydrogen sulfide and cell signaling." *Annual review of pharmacology and toxicology*. 2011;51:169-187. PubMed PMID: 21210746.

Calvert J.W., et al. "Genetic and pharmacologic hydrogen sulfide therapy attenuates ischemia-induced heart failure in mice." *Circulation*. Jul. 6, 2010;122(1):11-19. PubMed PMID: 20566952. Pubmed Central PMCID: 2955293. Epub Jun. 23, 2010.

Wang Q., et al., "Protective effects of cysteine analogues on acute myocardial ischemia: novel modulators of endogenous H(2)S production." *Antioxid Redox Signal*. May 15;12(10):1155-1165. PubMed PMID: 19842912. Epub Nov. 22, 2009.

Li L, et al., "GYY4137, a novel hydrogen sulfide-releasing molecule, protects against endotoxic shock in the rat." *Free radical biology & medicine*. Jul. 1, 2009;47(1):103-113. PubMed PMID: 19375498.

Kovačić D., et al. "Total Plasma Sulfide in Congestive Heart Failure." *Journal of Cardiac Failure*. 2012;18(7):541-548.

Kondo K, et al. "$H_2S$ Protects Against Pressure Overload—Induced Heart Failure via Upregulation of Endothelial Nitric Oxide Synthase (eNOS)." *Circulation*. Mar. 12, 2013;127(10):1116-1127.

Lee Z.W., et al. "The slow-releasing hydrogen sulfide donor, GYY4137, exhibits novel anti-cancer effects in vitro and in vivo." *PLOS ONE*. 2011;6(6):e21077. PubMed PMID: 21701688. Pubmed Central PMCID: 3119065.

Laggner H., et al. "The novel gaseous vasorelaxant hydrogen sulfide inhibits angiotensin-converting enzyme activity of endothelial cells." *J Hypertens*. Oct. 2007; 25(10):2100-2104. PubMed PMID: 17885553. Epub Sep. 22, 2007.

Sigurdsson A., et al., "Short- and long-term neurohormonal activation following acute myocardial infarction." *Am Heart J*. Nov. 1993;126(5):1068-1076. PubMed PMID: 8237747. Epub Nov. 1, 1993.

Jneid H., et al., "Combining neuroendocrine inhibitors in heart failure: reflections on safety and efficacy." *Am J Med*. Dec. 2007; 120(12):1090e1-1090e8. PubMed PMID: 18060931. Epub Dec. 7, 2007.

van Rooij E., et al. "Dysregulation of microRNAs after myocardial infarction reveals a role of miR-29 in cardiac fibrosis." *Proceedings of the National Academy of Sciences of the United States of America*. Sep. 2, 2008;105(35):13027-13032. PubMed PMID: 18723672. Pubmed Central PMCID: 2529064.

* cited by examiner

Figure 3A
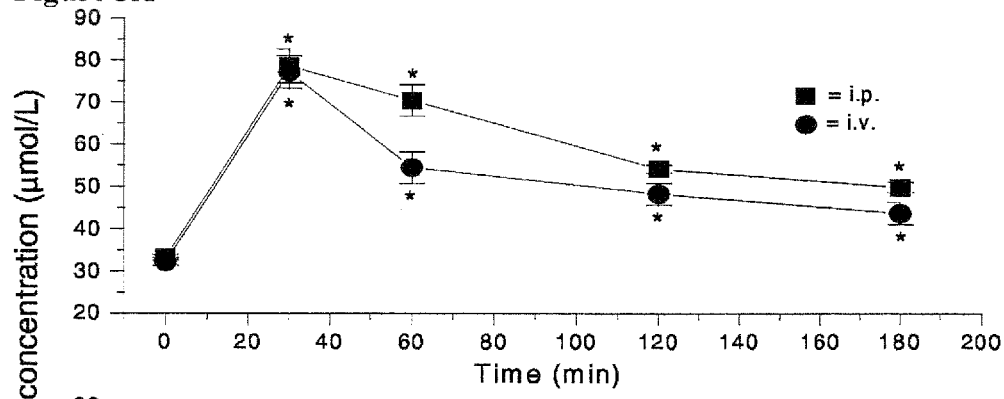
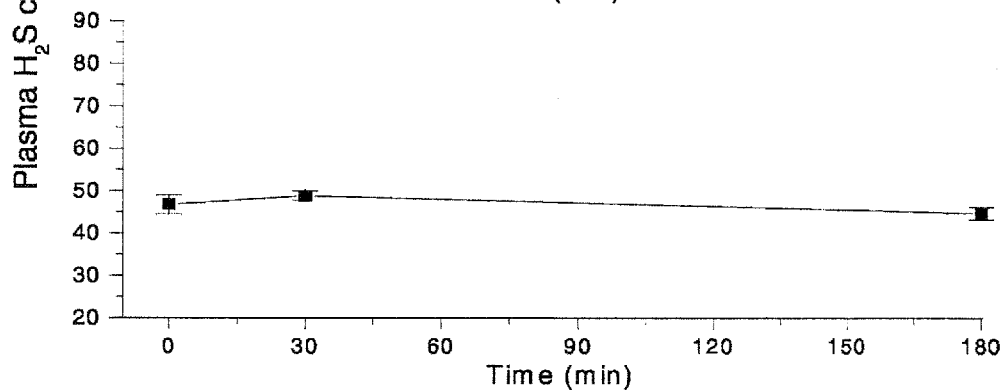
Figure 3B

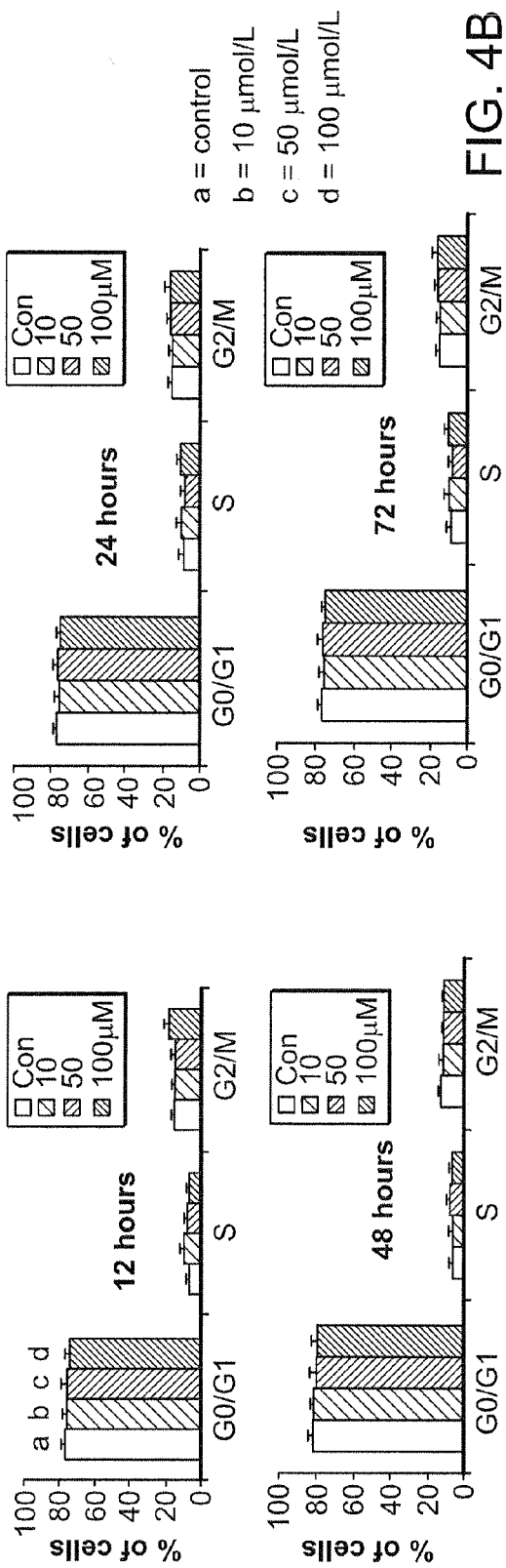
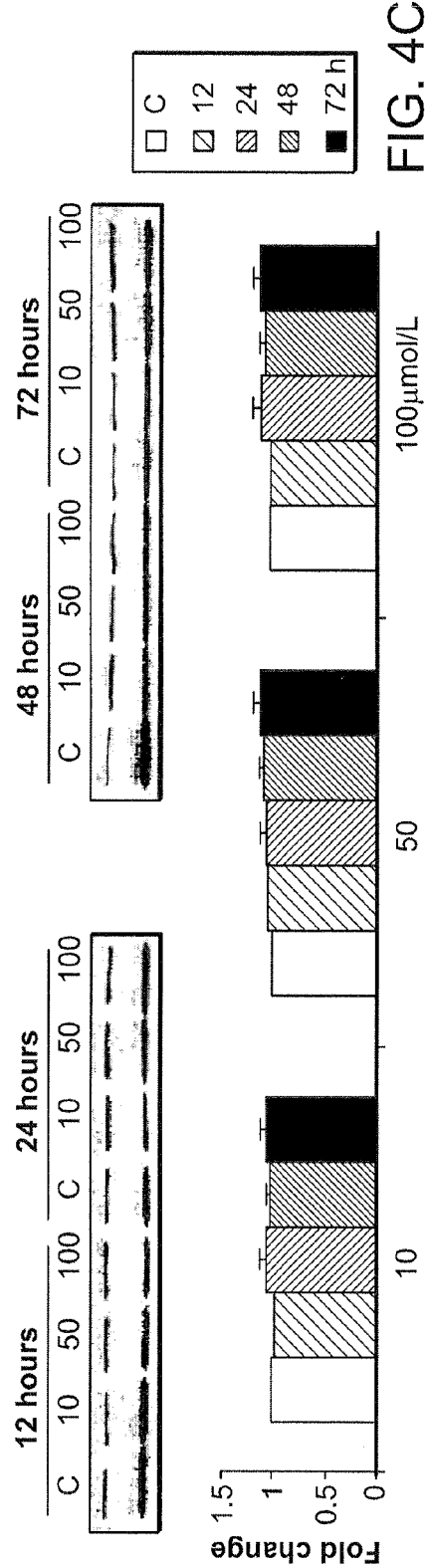
FIG. 4B
FIG. 4C

Figure 7A
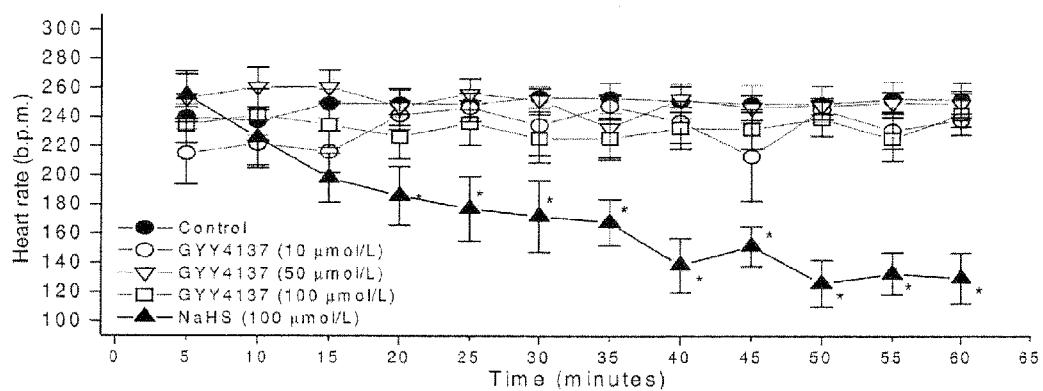
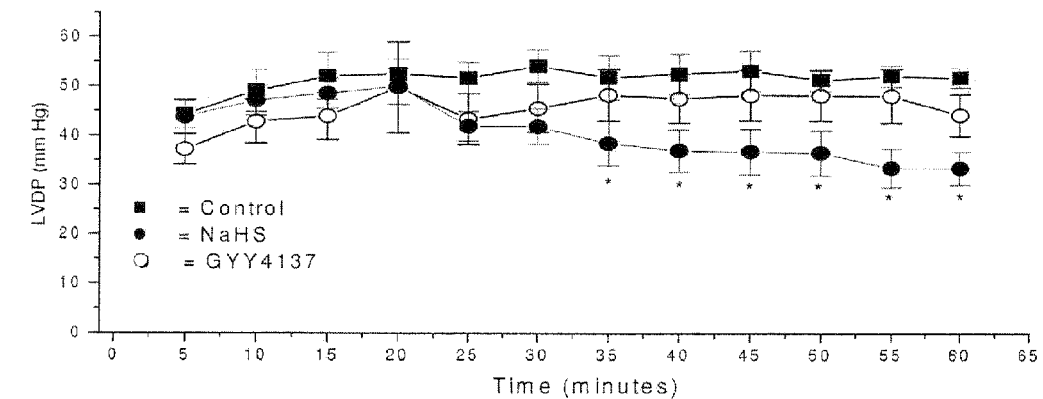
Figure 7B

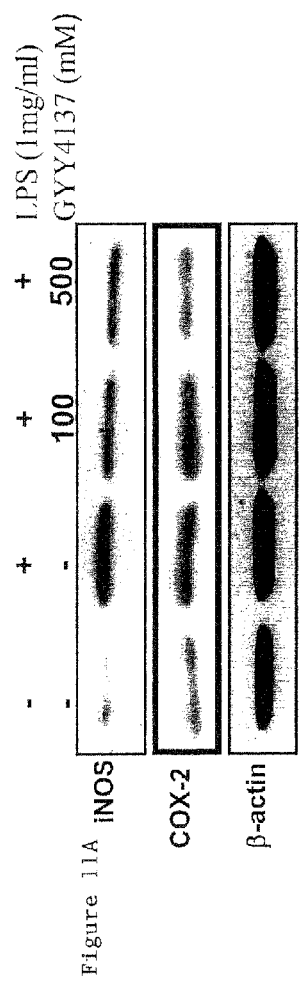
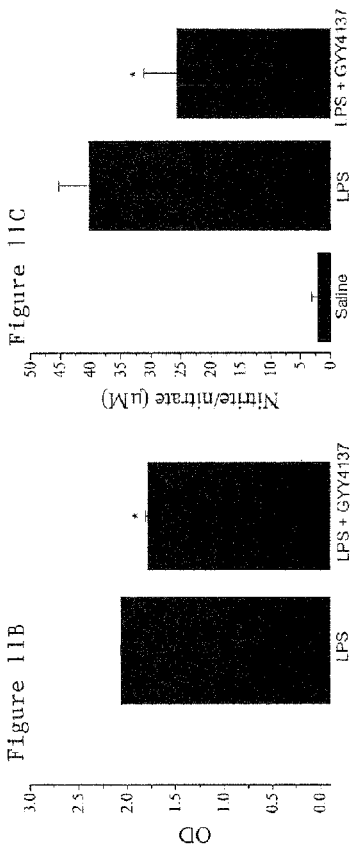
Figure 11A  Figure 11B  Figure 11C  Figure 11D  Figure 11E

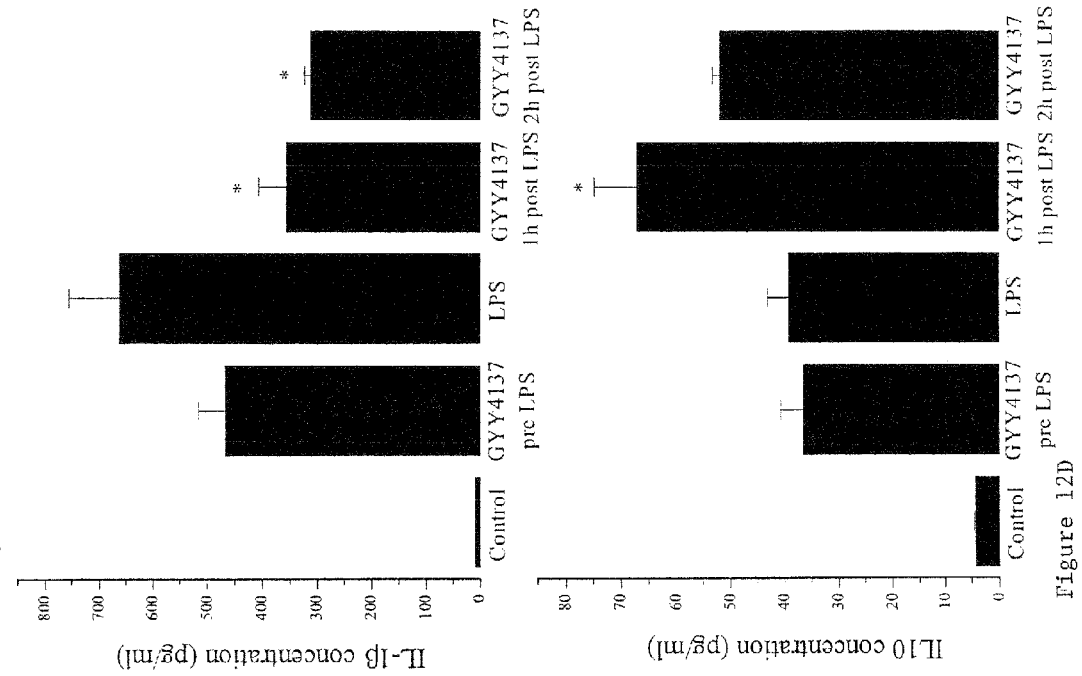
Figure 12A
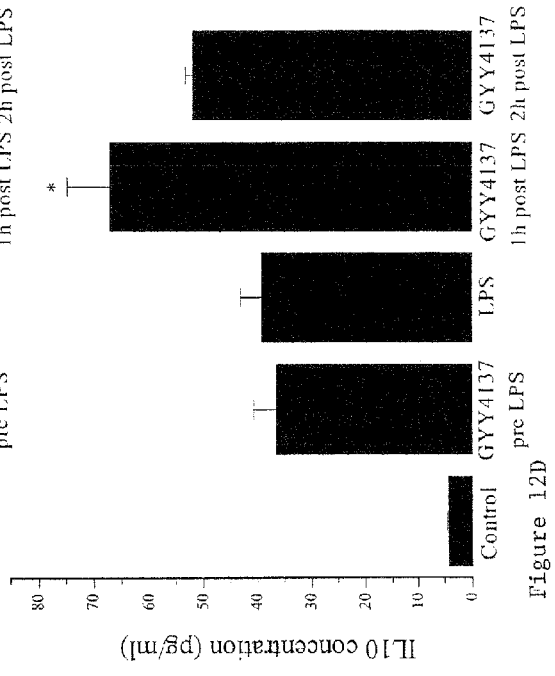
Figure 12B
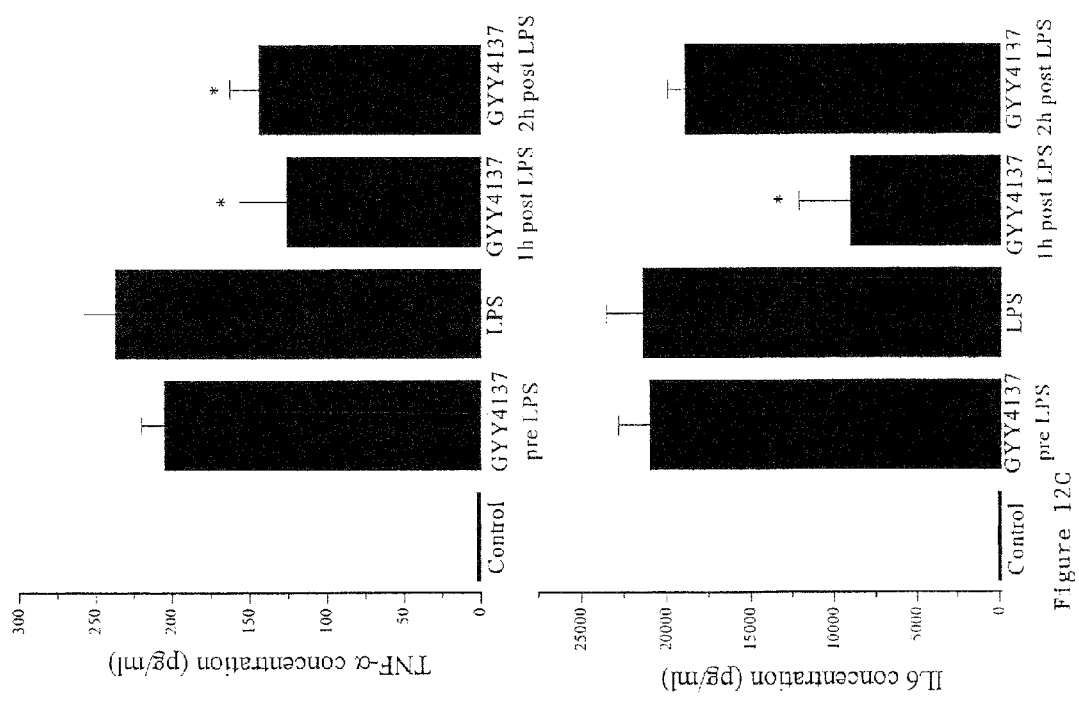
Figure 12C
Figure 12D

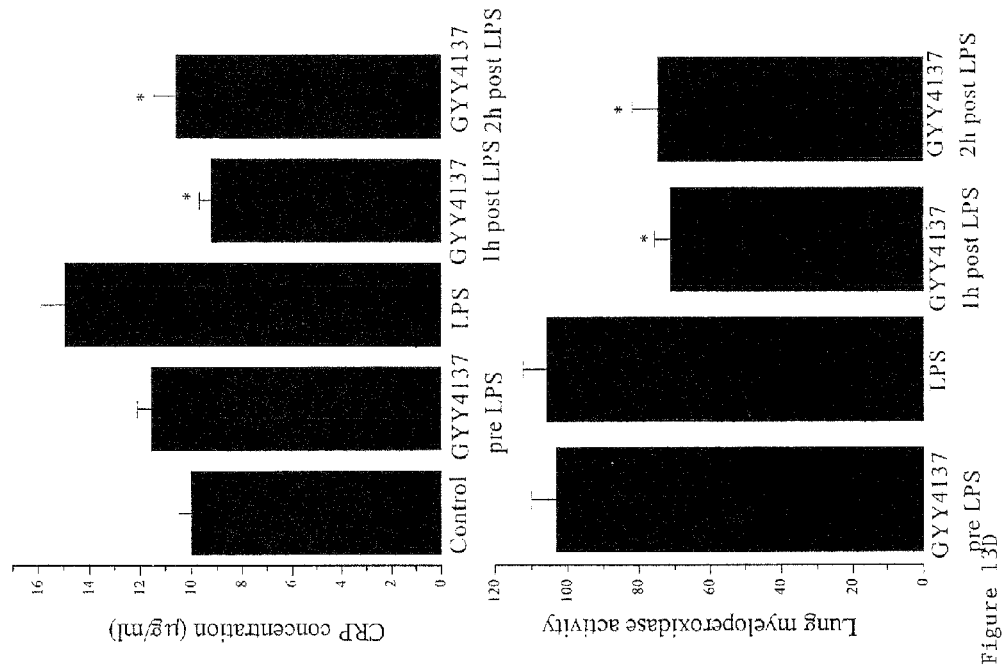
Figure 13B
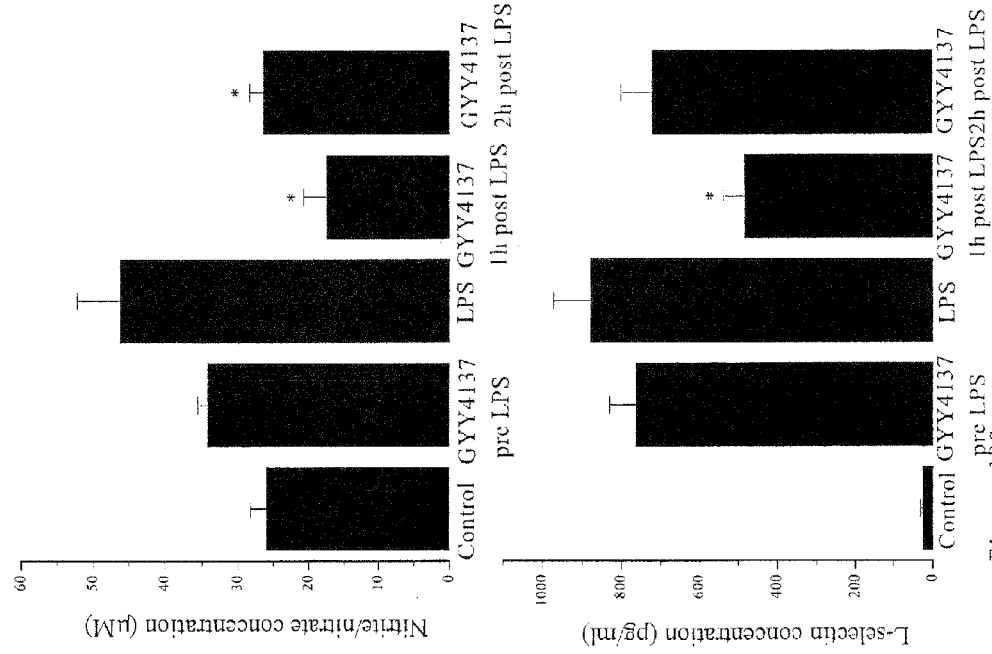
Figure 13A
Figure 13C
Figure 13D

MORPHOLIN-4-IUM 4 METHOXYPHENYL (MORPHOLINO) PHOSPHINODITHIOATE (GYY4137) AS A NOVEL VASODILATOR AGENT

RELATED APPLICATION

This application is a divisional of U.S. application Ser. No. 12/429,661, filed Apr. 24, 2009. The entire teachings of the above application are incorporated herein by reference.

BACKGROUND OF THE INVENTION

Numerous clinical conditions are associated with excessive constriction of one or more vascular beds. These include hypertension, angina pectoris and peripheral vascular disease all of which predispose to myocardial infarction, stroke and heart failure and erectile dysfunction. The healthcare and socioeconomic consequences of cardiovascular disease are staggering. According to World Health Organisation (WHO) estimates, 16.7 million people worldwide died of cardiovascular disease in 2003 which amounts to some 29% of all death globally. 80% of such deaths occur in low and middle income countries and account for more than 5 times the total number of deaths due to HIV/AIDS in these countries (American Heart Association, 2007). In economic terms, it has been estimated that cardiovascular disease costs every European Union (EU) citizen 230 Euros/year in healthcare and accounts for 268.8 million lost working days. Furthermore, at any one time approximately 600 million individuals globally suffer from hypertension and estimates suggest that this number will rise to 1.56 billion in 2025. Angina pectoris is also common and affected more than 6 million people in the USA in 2004 with a further 400,000 new cases diagnosed each year (Parker J. O. (2004) Am. J. Geriatric Cardiology, 13, 261-266). This number is expected to double by 2030. Other examples of cardiovascular disease include peripheral vascular disease which afflicts over 27 million people in Europe and North America (Belch J J, et al. (2003) Arch Int. Med., 163, 884-892). Finally, the incidence of erectile dysfunction globally is also rising from 152 million in 1995 to an estimated 322 million in 2025 (Aytak™, M., Krane, R. J. (1999) BJI Int., 84, 50-56).

The incidence of each of these cardiovascular disease states is rising perhaps as the population lives longer. Existing drug therapy for these conditions is based largely on the use of drugs which either directly or indirectly elicit vasodilation. These include, amongst others, $Ca^{++}$ channel antagonists, angiotensin converting enzyme inhibitors, sympatholytics and diuretics. However, the ever increasing incidence of these diseases is testimony to the fact that currently available drugs are not able "to stem the tide" and it is generally recognized that such treatments are inadequate.

The need for new vasodilator agents with novel mechanisms of action is clear.

SUMMARY OF THE INVENTION

In one aspect, the invention is directed to a method of administering hydrogen sulfide ($H_2S$) slowly and sustainably to an individual in need thereof comprising administering an effective amount of a compound represented by the following structural formula:

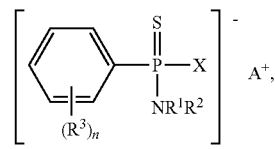

or a pharmaceutically acceptable salt thereof.

In another aspect, the invention is directed to a method of inducing vasodilation in an individual in need thereof comprising administering an effective amount of a compound represented by the following structural formula:

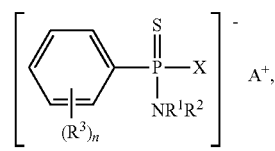

or a pharmaceutically acceptable salt thereof.

In another aspect, the invention is directed to a method of lowering blood pressure in an individual in need thereof comprising administering an effective amount of a compound represented by the following structural formula:

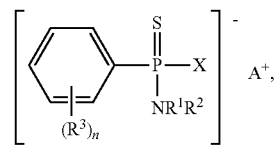

or a pharmaceutically acceptable salt thereof.

In another aspect, the invention is directed to a method of treating a condition associated with constriction of one or more vascular beds an individual in need thereof comprising administering an effective amount of a compound represented by the following structural formula:

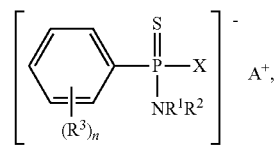

a pharmaceutically acceptable salt thereof.

In another aspect, the invention is directed to a method of treating hypertension in an individual in need thereof comprising administering an effective amount of a compound represented by the following structural formula:

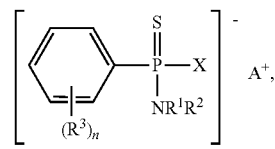

or a pharmaceutically acceptable salt thereof.

In another aspect, the invention is directed to a method of treating inflammation in an individual in need thereof comprising administering an effective amount of a compound represented by the following structural formula:

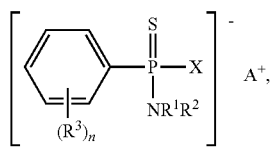

or a pharmaceutically acceptable salt thereof.

BRIEF DESCRIPTION OF THE DRAWINGS

FIGS. 3A-3B are graphs showing plasma concentrations of $H_2S$ (defined as $H_2S$, $HS^-$, and $S_2^-$) in animals administered either GYY4137 (133 μmol/kg IV or IP) (3A) or (3B) NaHS (20 μmol/kg IV) (3B). Results show time course and are mean±SEM; n=6. *P<0.05 vs baseline values.

FIGS. 4A-4C show cytotoxic effect of GYY4137 on cultured A10 vascular smooth cells as determined by effect on cell viability (trypan blue exclusion) (4A), cell cycle distribution (4B), and p53 expression (4C). Cells were exposed to different concentrations of GYY4137 (0 to 100 μmol/L) for 12 to 72 hours. Results show percent cell survival (4A), percentage of cells in each phase of the cell cycle (4B), and fold change in p53 expression (4C) and are mean±SEM of 4 separate experiments. Inset to 4C indicates representative blots at 12, 24, 48, and 72 hours for p53 (top panel) and actin (bottom panel).

FIGS. 7A-7B shows graphs of (7A) a time course of effect of GYY4137 (50 to 200 μmol/L) and NaHS (100 μmol/L) on heart rate (bpm) in Langendorff-perfused rat heart; and (7B) Left ventricular diastolic pressure (LVDP) of perfused rat hearts exposed to GYY4137 (100 μmol/L), NaHS (100 μmol/L), or vehicle (control). Hearts were perfused for 30 minutes before addition of drugs and thereafter for an additional 30 minutes. All results show mean±SEM; n=5 to 9. *P<0.05 vs control.

FIGS. 11A-11E shows the effect of GYY4137 (100 and 500 μM) on LPS (1 μg/ml, 24 h) induced upregulation of inducible nitric oxide synthase and cyclooxygenase-2 in RAW 264.7 cells (FIG. 11A). Effect of GYY4137 (100 μM) on NF-κB activation (FIG. 11B), nitrite/nitrate (FIG. 11C), $PGE_2$ (FIG. 11D) and TNF-α (FIG. 11E) concentration in RAW 264.7 cells exposed to LPS (1 μg/ml, 24 h). GYY4137 was co-incubated with LPS. Results show (FIG. 11A) representative blots from 3 independent experiments or (FIGS. 11B-11E) mean±s.e. mean, n=6, *P<0.05 c.f. LPS alone.

FIGS. 12A-12D shows the effect of GYY4137 (50 mg/kg, i.p.) on LPS-induced increase in plasma TNF-α (FIG. 12A), IL-1β (FIG. 12B), IL-6 (FIG. 12C) and IL-10 (FIG. 12D). GYY4137 was administered either 1 h before or 1 h or 2 h after LPS injection. Animals were killed 4 h after LPS injection. 'Control' indicates plasma concentration of each cytokine 4 h after administration of saline (1 ml/kg, i.p.) in place of LPS. Results show mean±s.e. mean, n=5-7, *P<0.05 c.f. LPS alone.

FIGS. 13A-13D show the effect of GYY4137 (50 mg/kg, i.p.) on LPS-induced increase in plasma nitrite/nitrate (FIG.

Figure 1:
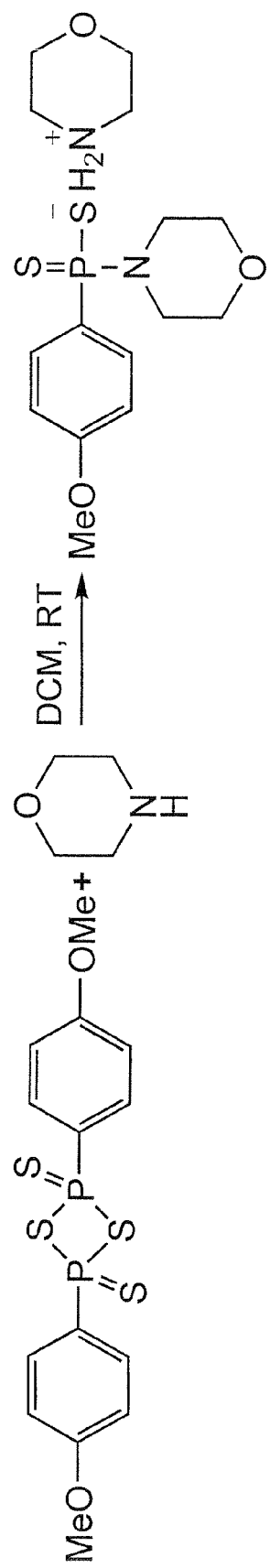
FIG. 1 shows the chemical synthesis of GYY4137; DCM indicates dichloromethane; RT, room temperature.

13A), □□C-reactive protein□□ (FIG. 13B), □L-selectin (FIG. 13C) and lung myeloperoxidase activity (FIG. 13D). GYY4137 was administered either 1 h before or 1 h or 2 h after LPS injection. Animals were killed 4 h after LPS injection. 'Control' indicates plasma concentration/enzyme activity 4 h after administration of saline (1 ml/kg, i.p.) in place of LPS. Myeloperoxidase activity is shown as % change compared with control (mean activity, 0.0123 OD405/μg DNA). Results show mean±s.e. mean, n=6-9, *P<0.05 c.f. LPS alone.

FIGS. 14A-14F show the effect of LPS administration on lung (14A, 14B) and liver (14C-14F) structure. LPS was either injected alone (14A, 14C, 14E) or followed 1 h thereafter by GYY4137 (14B, 14D, 14F). All animals were killed 4 h after LPS injection. Figure shows photomicrographs (×600) representative of at least 4 separate animals.

Figure 15:
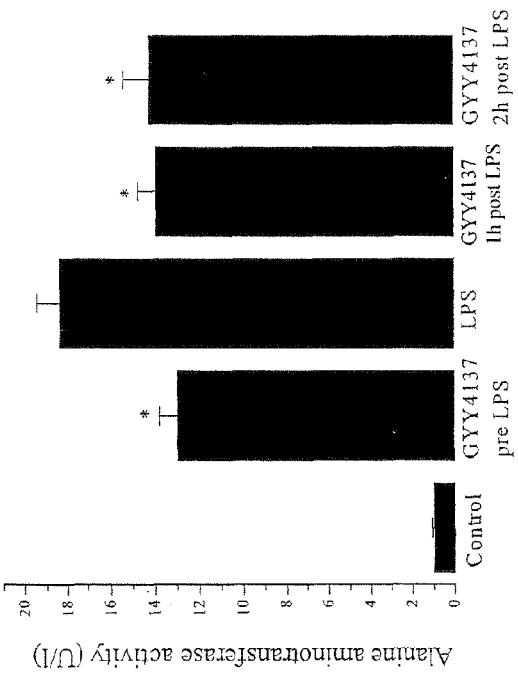
Figure 15A:
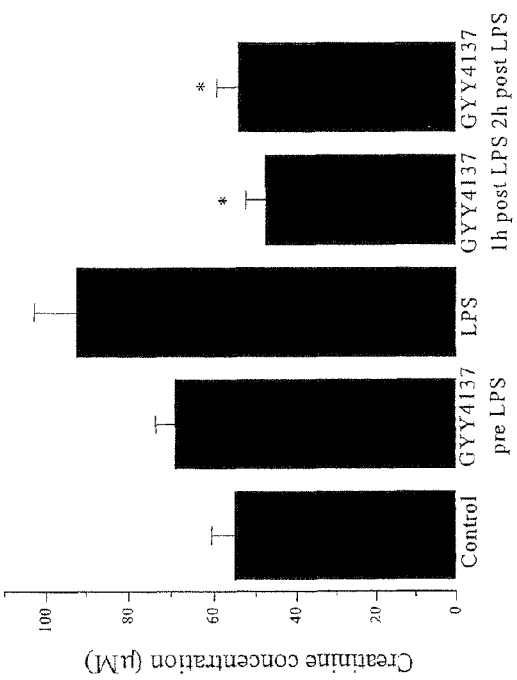
Figure 15C:
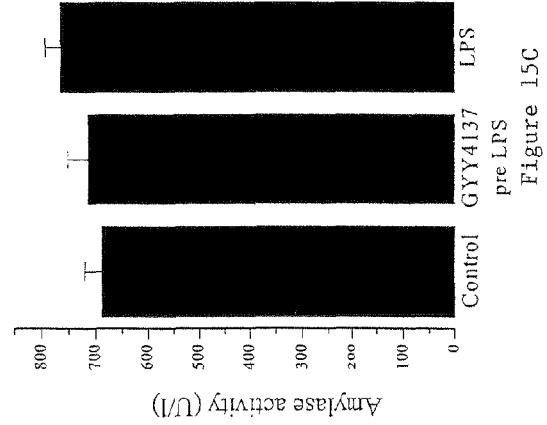

FIGS. 15A-15C show the effect of GYY4137 (50 mg/kg, i.p.) on LPS-induced increase in plasma creatinine (15A), □alanine aminotransferase (15B) □□ and amylase (15C). GYY4137 was administered either 1 h before or 1 h or 2 h after LPS injection. Animals were killed 4 h after LPS injection. 'Control' indicates plasma concentration/enzyme activity 4 h after administration of saline (1 ml/kg, i.p.) in place of LPS. Results show mean±s.e. mean, n=5-9, *P<0.05 c.f. LPS alone.

Figure 16A:
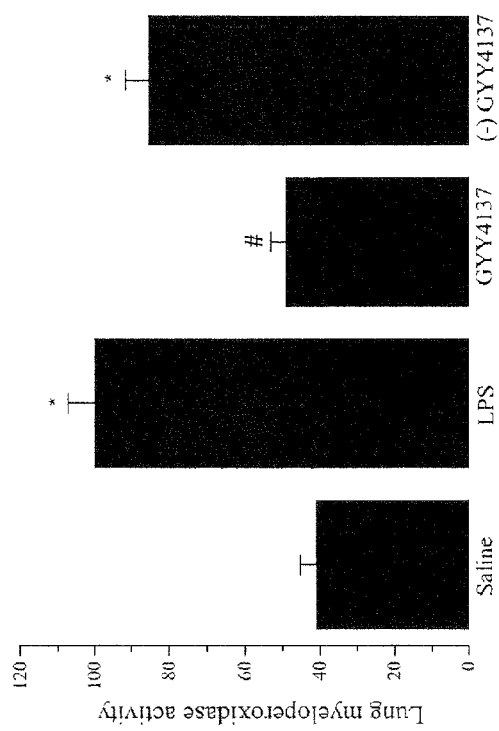
Figure 16B:
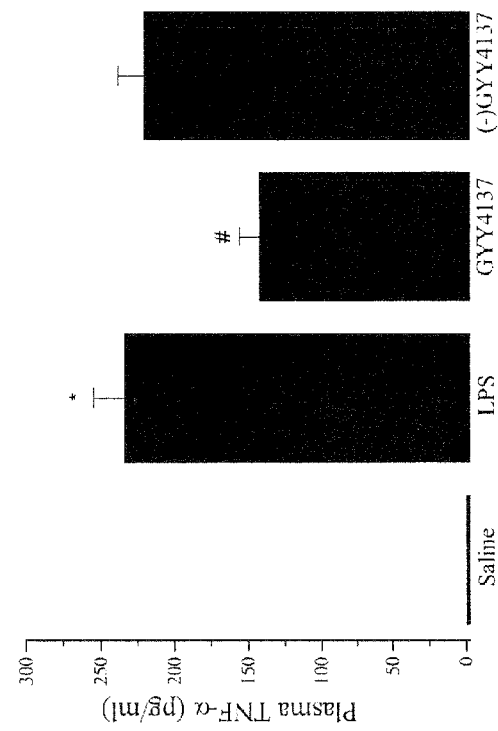

FIGS. 16A-16B show the comparison of the anti-inflammatory effect of 'decomposed GYY4137' (left at room temperature for 72 h; indicated here as (−) GYY4137) and authentic GYY4137 (both 50 mg/kg, i.p.) on LPS-induced increase in lung myeloperoxidase activity (16A) and plasma TNF-α (16B) concentration. (−) GYY4137 or GYY4137 were administered 1 h after LPS injection. Animals were killed 4 h after LPS injection. Results show mean±s.e. mean, n=6, *P<0.05 c.f. saline and *P<0.05 c.f. LPS.

Figure 17A:
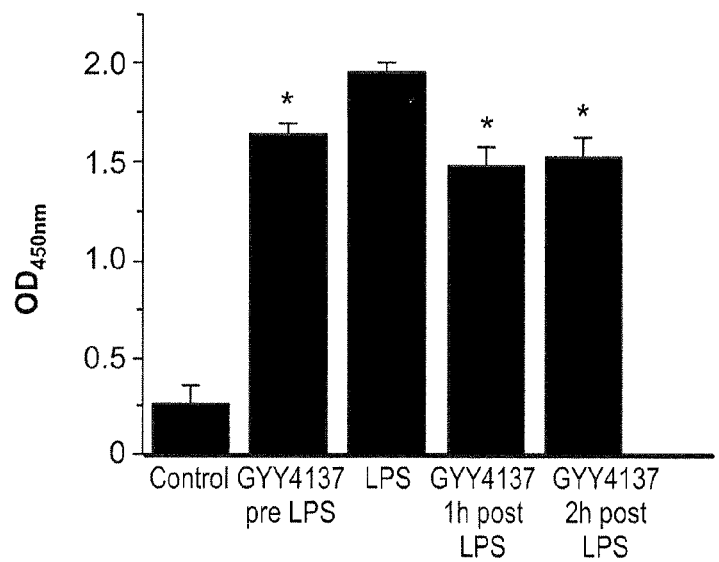
Figure 17B:
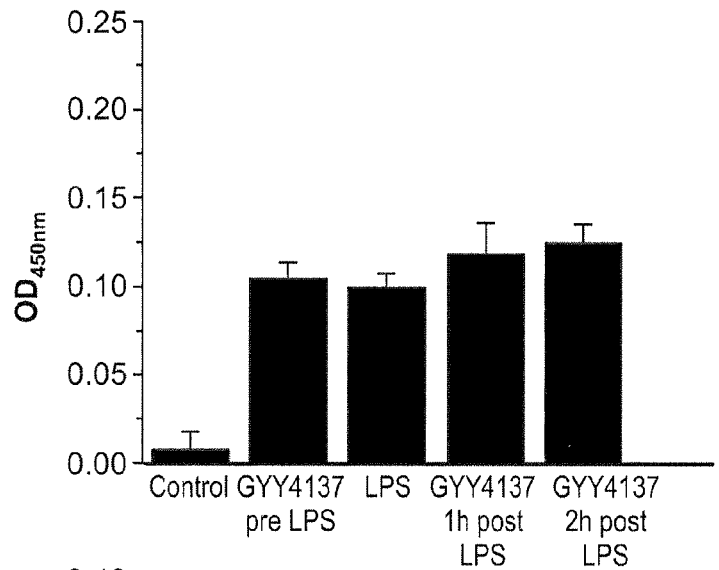
Figure 17C:
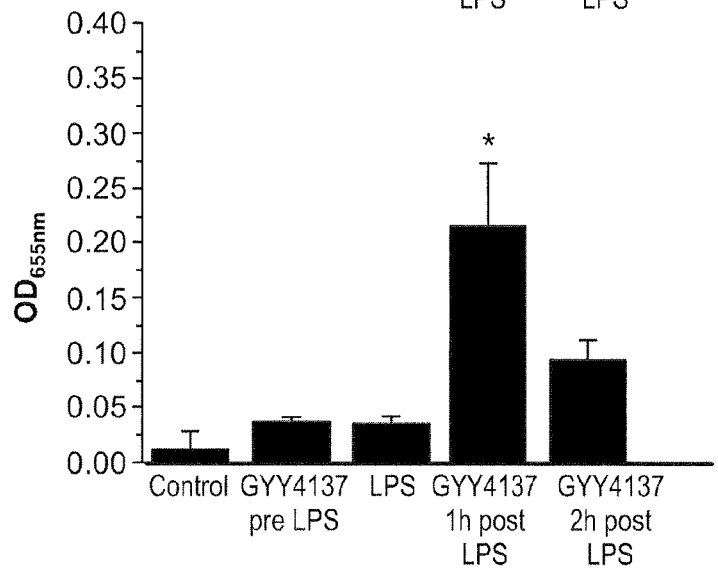

FIGS. 17A-17C show the effect of GYY4137 (50 mg/kg, i.p.) on LPS-induced increase in liver NF-κκB (17A), AP-1 (17B) and STAT-3 (17C) activation. GYY4137 was administered either 1 h before or 1 h or 2 h after LPS injection. Animals were killed 4 h after LPS injection. 'Control' indicates OD reading for each transcription factor 4 h after administration of saline (1 ml/kg, i.p.) in place of LPS. Results show mean±s.e. mean, n=6-9, *P<0.05 c.f. LPS alone.

DETAILED DESCRIPTION OF THE INVENTION

Over the years, one form of drug treatment for selected cardiovascular disease has involved the use of compounds which either mimic the activity or potentiate the effect of the naturally occurring vasodilator agent, nitric oxide (NO). For example, angina pectoris has been treated successfully with glyceryl trinitrate (GTN—an NO donor) for well over a hundred years and erectile dysfunction has, to some extent, been countered by the use of sildenafil which promotes the activity of NO by preventing the catabolism of cGMP. Whilst NO is now widely believed to exert a range of effects on the cardiovascular system—recent years has seen increased interest in the possible biological effects of another seemingly analogous gaseous mediator, hydrogen sulphide ($H_2S$). Within the cardiovascular system, $H_2S$ has been shown to mimic the vasodilator effect of NO both in vitro and in vivo.

Parallel lines of investigation have revealed changes in endogenous $H_2S$ formation/activity in animals with experimentally induced animal disease models characterized by excessive blood vessel constriction. These conditions include hypertension and hypoxic pulmonary vasoconstriction. In both of these animal models, $H_2S$ formation is deficient as evidenced by reduced plasma levels of $H_2S$.

Accordingly, as shown herein, under the appropriate experimental condition(s), an $H_2S$ donor drug will, exert vasodilator activity in isolated blood vessels in vitro and, lower blood pressure in anaesthetized animals in vivo.

Based on the observation (noted above) that $H_2S$ is deficient in animals with experimentally induced vasoconstrictor states, whether administration of an $H_2S$ donor drug is of value in such conditions was investigated. Further investigated was that while some $H_2S$ "donor drugs" have already been identified (e.g. sodium hydrosulfide, NaHS), this and related sulfide salts release $H_2S$ explosively (over a period of seconds) in solution and are consequently not likely to be of utility in the clinical setting. Described herein are molecules with the ability to release $H_2S$ in a sustained manner over an extended period of time.

Experiments described herein show that GYY4137 releases $H_2S$ in a slow and sustained manner in vitro and in vivo and exerts vasodilator activity in vitro and in vivo commensurate with a potential for clinical utility. Accordingly, the invention provides methods of administering $H_2S$ slowly and sustainably to an individual in need thereof comprising administering an effective amount of a compound represented by the following structural formula:

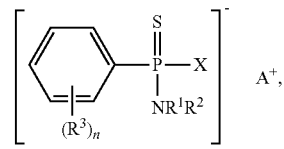

or a pharmaceutically acceptable salt thereof.

As used herein release of $H_2S$ "slowly and sustainably" (e.g., in vivo) refers to release of $H_2S$ at about 20, 30 seconds or longer (e.g., about 1 minute, 1.5 minutes, 2 minutes, 3 minutes, 4 minutes, 5 minutes, 10 minutes, 20 minutes, 30 minutes, 40 minutes, 50 minutes, 60 minutes, 70 minutes, 80 minutes, 90 minutes, 100 minutes, 110 minutes, 120 minutes, 130 minutes, 140 minutes, 150 minutes, 160 minutes, 170 minutes, 180 minutes, 3.5 hours, 4 hours, 4.5 hours, 5 hours and increments thereof) after administration to the individual (in contrast to "explosively" (e.g., immediately or within about one or two seconds) after administration to the individual). In addition, release of $H_2S$ "slowly and sustainably" refers to elevation (increased expression) of $H_2S$ in the individual for about 5 minutes, 10 minutes, 20, minutes, 30 minutes, 40 minutes, 50 minutes, 60 minutes, 70 minutes, 80 minutes, 90 minutes, 100 minutes, 110 minutes, 120 minutes, 130 minutes, 140 minutes, 150 minutes, 160 minutes, 170 minutes, 180 minutes, 190 minutes, 200 minutes, or minute increments of these in the individual after administration of $H_2S$.

In addition, the invention provides methods of using such molecules as vasodilator agents (e.g., to lower blood pressure) and methods of treating (e.g., alleviating) conditions associated with constriction of vasculature (e.g., vascular beds) in an individual in need thereof, comprising administering an effective amount of a compound represented by the following structural formula:

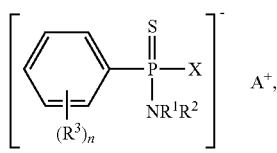

or a pharmaceutically acceptable salt thereof.

Examples of conditions associated with constriction of vasculature include hypertension, angina pectoris, peripheral vascular disease, myocardial infarction, stroke, heart failure, cardiomyopathy (Su, Y W., et al., *Circ. J.*, 73(4):741-749 (2009), atherosclerosis (Muellner, M K, et al., *Biochem. J.*, Epub (Mar. 5, 2009); Jeney, V., et al., *Free Radic. Biol. Med.*, 46(5):616-623 (2009)), pulmonary hypertension (Li, X H., et al., *Exp. Biol. Med.*, Epub (Feb. 20, 2009); Chunyu, Z., et al., *Biochem. Biophys. Res. Comm.*, 302(4):810-816 (2003); Qingyou, Z., et al., *Biochem. Biophys. res. Comm.*, 317(1):30-37 (2004); Li, X., et al., *Heart Vessels*, 23(6):409-419 (2008); Li, X H., et al., *Zhongguo Yi Xue Yuan Xue Bao*, 28(2):159-163 (2006); Li, X H., et al., *Zhonghua Er Ke Za Zhi*, 44(12):941-945 (2006)); Li, X H., et al., *Acta Pharmol. Sin.*, 27(8):971-980 (2006); Li, X., et al., *Life Sci.*, 81(10): 841-849 (2007)), kidney dysfunction (Xia, M., et al., *J. Pharmacol. Exp. Ther.*, Epub (Feb. 26, 2009)), erectile dysfunction (Srilatha, B., et al., *J. Sex Med.*, 4(5):1304-1311 (2007); d'Emmanuele di Villa Bianca, R., et al., *Proc. Natl. Acad. Sci., USA*, 106(11):451304518 Epub (March 2009); Shukla, N., et al., *BJU Int.*, Epub (Feb. 23, 2009)), intestinal ischemia (Liu, H., et al., *J. Pharm. Pharmacol.*, 61(2):207-212 (2009); Yusof, M., et al., *Am. J. Heart Circ. Physiol.*, 296(3):H686-H876 (2009)), metabolic disease (Feng, X., et al., *Biochem. Biophys. Res. Comm.*, 380(1):153-159 (2009); Yusuf, M., et al., *Biochem. Biophys. Res. Comm.*, 333(4):1146-1152 (2005); Wu., L., et al., *Lab Invest.*, 89(1):59-67 (2009); Yang, W., et al., *J. Physiol.*, 569:519-531 (2005); Kaneko, Y, et al., *Cytokine*, 45(2):117-123 (2008)), asthma (Chen, Y H., et al., *Cytokine* 45(2):117-123 (2008); Wu, R., et al., *Zhonghua Jie He Hu Xi Za Zhi*, 30(7):522-526 (2007)), acute respiratory distress syndrome (Muzaffar, S., et al., *Br. J. Pharmacol.*, 155(7):984-994 (2008); Muzaffar, S., et al., *J. Vasc. Res.*, 45(6):521-528 (2008)), and eye disease (Monjok, E M., et al., *Exp. eye Res.*, 87(6):612-616 (2008); Kulkarni, K H., et al., *Neurochem. Res.*, 34(3):400-406 (2009)).

Additional experiments herein show that administration of GYY4137 (50 mg/kg, i.v.) to anesthetized rats 10 min after lipopolysaccharide (LPS, 4 mg/kg, i.v.) decreased the slowly-developing hypotension. GYY4137 inhibited LPS-induced TNF-α production in rat blood and reduced the LPS-evoked rise in NF-κB activation, inducible nitric oxide synthase/cyclooxygenase-2 expression and generation of $PGE_2$ and nitrate/nitrite in RAW 264.7 macrophages. GYY4137 (50 mg/kg, i.p.) administered to conscious rats 1 h or 2 h after (but not 1 h before) LPS decreased the subsequent (4 h) rise in plasma proinflammatory cytokines (TNF-α, IL-1β, IL-6), nitrite/nitrate, C-reactive protein and L-selectin. GYY4137 administration also decreased the LPS-evoked increase in lung myeloperoxidase activity, increased plasma concentration of the anti-inflammatory cytokine, IL-10, and decreased tissue damage as determined histologically and by measurement of plasma creatinine and alanine aminotransferase activity. Time-expired GYY4137 (50 mg/kg, i.p.) did not affect LPS-induced rise in plasma TNF-α or lung myeloperoxidase activity. GYY4137 also decreased the LPS-mediated upregulation of liver transcription factor (NF-B and STAT-3). These results indicate an antiinflammatory effect of GYY4137.

Accordingly, another aspect of the invention is a method of treating inflammation in an individual in need thereof comprising administering an effective amount of a compound represented by the following structural formula:

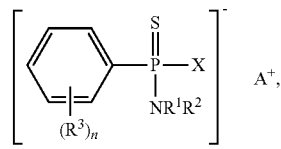

or a pharmaceutically acceptable salt thereof.

In one aspect, the inflammation is systemic inflammation. In another aspect, the systemic inflammation is caused by endotoxic shock. In yet another aspect, the compound is administered after inflammation has occurred in the individual. For example, the compound is administered about 10 minutes, 20 minutes, 30 minutes, 40 minutes, 50 minutes, 1 hour, 2 hours 3 hours, 4 hours, 5 hours, 8 hours, 10 hours, 12 hours, 14 hours, 16 hours, 18 hours, 20 hours, 24 hours, 48 hours, 72 hours, etc, or increments thereof, after inflammation has occurred in the individual. The skilled practitioner can readily ascertain the dosing and administration regime based upon patient condition, age and other factors.

In other aspects, the invention is directed to use of a compound represented by the following structural formula:

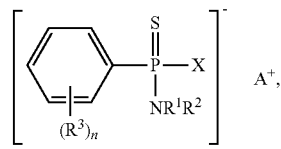

or a pharmaceutically acceptable salt thereof, for the manufacture of a medicament to administer hydrogen sulfide ($H_2S$) slowly and sustainably.

In other aspects, the invention is directed to use of a compound represented by the following structural formula:

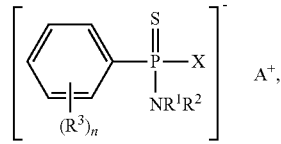

or a pharmaceutically acceptable salt thereof, for the manufacture of a medicament to induce vasodilation.

In other aspects, the invention is directed to use of a compound represented by the following structural formula:

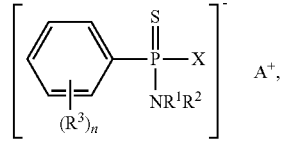

or a pharmaceutically acceptable salt thereof, for the manufacture of a medicament to a lower blood pressure.

In other aspects, the invention is directed to use of a compound represented by the following structural formula:

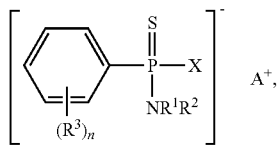

a pharmaceutically acceptable salt thereof for the manufacture of a medicament to treat a condition associated with constriction of one or more vascular bed.

In other aspects, the invention is directed to use of a compound represented by the following structural formula:

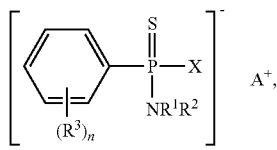

or a pharmaceutically acceptable salt thereof, for the manufacture of a medicament to a method of treat hypertension.

In other aspects, the invention is directed to use of a compound represented by the following structural formula:

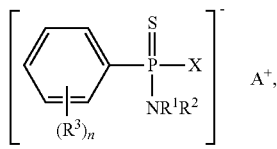

or a pharmaceutically acceptable salt thereof, for the manufacture of a medicament to treat inflammation.

Based on the biological effect of $H_2S$ to relax blood vessels, reduce blood pressure and protect against inflammation in experimental animals, provided herein are chemical entities with the ability to release $H_2S$ slowly and in a sustained fashion both in vitro and in vivo. The methods described herein have been demonstrated using the chemical compound GYY4137. As used herein, "GYY4137" is one of a series of chemicals which were synthesized as described in Example 1 (FIG. 1). GYY4137 is known to promote vulcanization of rubber and is not related to any therapeutic effect (U.S. Pat. No. 2,954,379). However, GYY4137 has not previously been reported to exhibit any effect on the cardiovascular system (or any other biological system) in animals or in man and, therapeutic efficacy for this compound have not been lodged. As shown herein, unlike standard $H_2S$ donors, GYY4137 released $H_2S$ slowly over minutes or hours and elevated plasma levels of this gaseous mediator in plasma of treated rats for up to 3 h. GYY4137 caused slow relaxation of rat aortic rings, dilated the preconstricted rat renal vasculature in vitro and both lowered blood pressure and reduced/prevented L-N(G) nitroarginine methyl ester (L-NAME) evoked hypertension in the rat in vivo. These effects were either partially or completely prevented by glibenclamide ($K_{ATP}$ channel blocker) and as such presumed to be mediated by released $H_2S$. A particular aspect of the invention is the use of GYY4137 as a vasodilator agent.

Hydrogen sulphide ($H_2S$) has long been recognised as an environmental toxicant generated, for example, as a by-product of numerous industrial processes, present within volcanic discharge and found at high levels in sewage facilities. Interestingly, other gases with essentially similar profiles of activity, including nitric oxide (NO) and carbon monoxide (CO), were also once considered solely as metabolic toxicants but are now recognised as naturally occurring mediators exerting a range of biological effects with physiological and/or pathophysiological significance. $H_2S$ is formed naturally from cysteine in mammalian (Kamoun, P. (2004) Amino Acids, 26, 243-254) cells by two pyridoxal phosphate dependent enzymes, cystathionine γ lyase (CSE) and cystathionine☐β synthetase (CBS). In recent years, $H_2S$ has been reported to dilate blood vessels both in vitro (Zhao, W., et al. (2001) EMBO J., 20, 6008-6016) and in vivo (Zhao, W., et al. (2001) EMBO J., 20, 6008-6016; Ali, M Y, et al., (2006) Br J. Pharmacol. 149, 625-634) by opening smooth muscle cell $K_{ATP}$ channels (Zhao, W., Wang, R. (2002) Am. J. Physiol. Heart Circ., Physiol., 283, H474-480) and to play as yet not clearly defined roles in disease states such as hypertension (Yan, H., Du, J., Tang, C. (2004) Biochem. Biophys. Res. Commun., 313, 22-27), myocardial infarction (Zhu, Y Z, et al. (2007) J Appl Physiol., 102, 261-268), septic (Li, L., et al., (2005) FASEB J., 19, 1196-1198) and haemorrhagic shock (Mok, Y. Y. P., et al. (2004) Br. J. Pharmacol., 143, 881-889), arthritis (Bhatia, M., et al., (2005) Br. J. Pharmacol., 145, 141-144) and in pancreatitis (Bhatia, M., et al., (2004) FASEB J. 19, 623-625). Interestingly, many of the biological properties of $H_2S$ mimic the activity of both NO and CO leading to the suggestion that $H_2S$ may function together with these other gases to form a functional triumvirate of endogenous gaseous mediators.

In recent years, research in the field of both NO and CO has been greatly facilitated by the development of numerous organic compounds which, either spontaneously or by enzymatic cleavage, release free NO/CO the effects of which on cells, tissues and intact animals (including man) can then be studied. To date, only one such $H_2S$ releasing drug has been routinely used in biological experiments. Sodium hydrosulfide (NaHS) dissolves in aqueous buffer to yield $Na^+$ and hydrosulfide ($HS^-$) anion which then reacts with $H^+$ to form $H_2S$. Whilst NaHS is often referred to as an '$H_2S$ donor drug' the process described above represents a simple, instantaneous chemical equilibrium and as such $H_2S$ generation from NaHS cannot be controlled which detracts from its use as a donor drug.

Recognising the need for organic molecules (compound) capable of the slow release of H2S over extended (c.f. NaHS) periods of time, provided herein are organic, water-soluble molecules with the ability to release $H_2S$ spontaneously. In one aspect, the compound is represented by the following structural formula:

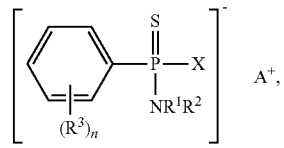

In a particular aspect, the invention relates to the identification of morpholin-4-ium 4-methoxyphenyl(morpholino)phosphinodithioate (hereinafter referred to as GYY4137) as a novel vasodilator agent with potential therapeutic applications in clinical conditions associated with excess vasoconstriction or in which a vasodilator would be of benefit.

The term "alkyl", used alone or as part of a larger moiety such as "arylalkyl" or "cycloalkylalkyl" means a straight or branched hydrocarbon radical having 1-10 carbon atoms and includes, for example, methyl, ethyl, n-propyl, isopropyl, n-butyl, sec-butyl, isobutyl, tert-butyl, n-pentyl, i-pentyl, n-hexyl, n-heptyl, n-octyl, n-nonyl, n-decyl and the like. Unless otherwise described, exemplary substituents for a substituted alkyl group include the values and specific values described for $R^4$.

The term "cycloalkyl" means a monocyclic, bicyclic or tricyclic, saturated hydrocarbon ring having 3-12 carbon atoms and includes, for example, cyclopropyl, cyclobutyl, cyclopentyl, cyclohexyl, cycloheptyl, cyclooctyl, bicyclo[2.2.2]octyl, bicyclo[2.2.1]heptyl, spiro[4.4]nonane, adamantyl and the like. Unless otherwise described, exemplary substituents for a substituted cycloalkyl group include the values and specific values described for $R^4$.

"Aryl", used alone or as part of a larger moiety as in "arylalkyl", means a 6-10 membered carbocyclic aromatic monocyclic or polycyclic ring system. Examples include phenyl and naphthyl. The term "aryl" also includes phenyl rings fused to non-aromatic carbocyclic ring or to a heterocyclyl group. The term "aryl" may be used interchangeably with the terms "aromatic group", "aryl ring" "aromatic ring", "aryl group" and "aromatic group". Unless otherwise described, exemplary substituents for a substituted aryl group include the values and specific values described for $R^4$.

"Hetero" refers to the replacement of at least one carbon atom member in a ring system with at least one heteroatom selected from N, S, and O. A hetero ring may have 1, 2, 3, or 4 carbon atom members replaced by a heteroatom.

"Heterocyclyl" refers to a saturated or unsaturated, non-aromatic, monocyclic or polycyclic ring system of 3 to 20 atoms, 3 to 12 atoms, or 3 to 8 atoms, containing one to four ring heteroatoms chosen from O, N and S. Exemplary heterocyclyls include pyrrolidine, pyrrolidin-2-one, 1-methylpyrrolidin-2-one, piperidine, piperidin-2-one, 2-pyridone, 4-pyridone, piperazine, 1-(2,2,2-trifluoroethyl)piperazine, piperazin-2-one, 5,6-dihydropyrimidin-4-one, pyrimidin-4-one, tetrahydrofuran, tetrahydropyran, tetrahydrothiophene, tetrahydrothiopyran, isoxazolidine, 1,3-dioxolane, 1,3-dithiolane, 1,3-dioxane, 1,4-dioxane, 1,3-dithiane, 1,4-dithiane, oxazolidin-2-one, imidazolidin-2-one, imidazolidine-2,4-dione, tetrahydropyrimidin-2(1H)-one, morpholine, N-methylmorpholine, morpholin-3-one, 1,3-oxazinan-2-one, thiomorpholine, thiomorpholine 1,1-dioxide, tetrahydro-1,2,5-thiaoxazole 1,1-dioxide, tetrahydro-2H-1,2-thiazine 1,1-dioxide, hexahydro-1,2,6-thiadiazine 1,1-dioxide, tetrahydro-1,2,5-thiadiazole 1,1-dioxide and isothiazolidine 1,1-dioxide. Unless otherwise described, exemplary substituents for a substituted heterocyclyl group include the values and specific values described for $R^4$.

"Heterocyclyl" also includes heteroaryl groups. The term "heteroaryl" means a 5-10 membered monovalent heteroaromatic monocyclic and polycylic ring radical containing 1 to 4 heteroatoms independently selected from N, O, and S. The term "heteroaryl" also includes monocyclic heteroaryl ring fused to non-aromatic carbocyclic ring or to a heterocyclyl group. Heteroaryl groups include furyl, thienyl, thiophenyl, pyrrolyl, oxazolyl, thiazolyl, imidazolyl, pyrazolyl, isoxazolyl, isothiazolyl, oxadiazolyl, triazolyl, thiadiazolyl, pyridinyl, pyridinyl-N-oxide, pyridazinyl, pyrimidinyl, pyrazinyl, indolizinyl, indolyl, isoindolyl, benzo[b]furyl, benzo[b]thienyl, indazolyl, benzimidazolyl, benzthiazolyl, purinyl, 4H-quinolizinyl, quinolinyl, isoquinolinyl, quinazolinyl, benzothienyl, benzofuranyl, 2,3-dihydrobenzofuranyl, benzodioxolyl, benzimidazolyl, indazolyl, benzisoxazolyl, benzoxazolyl, benzothiazolyl, cinnolinyl, phthalzinyl, quinazolinyl, quinoxalinyl, 1,8-naphthyridinyl, 1,2,3-triazolyl, 1,2,4-triazolyl, 1,3,4-oxadiazolyl, 1,2,5-thiadiazolyl, 1,2,5-thiadiazolyl-1-oxide, 1,2,5-thiadiazolyl-1,1-dioxide, 1,3,4-thiadiazolyl, 1,2,4-triazinyl, 1,3,5-triazinyl, tetrazolyl, and pteridinyl. The terms "heteroaryl", "heteroaryl ring", and "heteroaryl group" are used interchangeably herein. Unless otherwise described, exemplary substituents for a substituted heterocyclyl group include the values and specific values described for $R^4$.

One embodiment of the invention is a method of administering hydrogen sulfide ($H_2S$) slowly and sustainably to an individual in need thereof comprising administering an effective amount of a compound represented by Structural Formula (I):

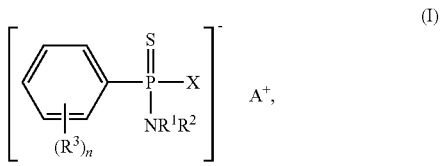

or a pharmaceutically acceptable salt thereof. Values and specific values for the variables of Structural Formula (I) are as follows:

X is O or S and $A^+$ is present; or

X is halogen, OMs or OTs and $A^+$ is absent. As used herein, "OMs" is a mesylate group represented by the chemical formula —$OS(O)_2CH_3$. As used herein, "OTs" is tosylate group represented by the chemical formula

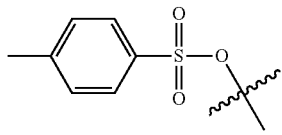

In one embodiment, X is O or S and $A^+$ is present. In a specific embodiment, X is S and $A^+$ is present. In another embodiment, X is O and $A^+$ is present.

Alternatively, X is halogen, OMs or OTs and $A^+$ is absent. In a specific alternative embodiment, X is halogen and $A^+$ is absent. In another specific alternative embodiment, X is Cl and $A^+$ is absent. In another specific alternative embodiment, X is OMs and $A^+$ is absent. In another specific alternative embodiment, X is OTs and $A^+$ is absent.

When present, $A^+$ is a monovalent cation. As used herein a "cation" is a positively charged ion. As used herein "monovalent" means that the charge of the cation is +1. Cations can be monoatomic or polyatomic.

In one embodiment, the monovalent cation is a monoatomic cation. A monoatomic cation contains one positively charged atom. Examples of monoatomic cations include, but are not limited to $H^+$, $Li^+$, $Na^+$, $K^+$ or $Cu^+$. In one embodiment, the monovalent cation is a metal cation. In a specific embodiment, $A^+$ is selected from lithium, sodium or potassium. In another specific embodiment, $A^+$ is potassium. Alternatively, $A^+$ is $H^+$.

In one embodiment, the monovalent cation is a polyatomic cation. A polyatomic cation is a positively charged molecule that contains more than one atom. Unless otherwise described, exemplary substituents for a substituted a polyatomic cation include the values and specific values described for $R^4$.

Examples of polyatomic cations include, but are not limited to $NH_4^+$, $N(C_1-C_4\text{alkyl})H_3^+$ (for example, $N(\text{methyl})H_3^+$ or $N(\text{ethyl})H_3^+$), $N(\text{benzyl})H_3^+$, $N(\text{phenyl})H_3^+$, and $H_3O^+$. In a specific example, $A^+$ is selected from $NH_4^+$, $N(C_1-C_4\text{alkyl})H_3^+$ (for example, $N(\text{methyl})H_3^+$ or $N(\text{ethyl})H_3^+$), $N(\text{benzyl})H_3^+$, and $N(\text{phenyl})H_3^+$. In another specific embodiment, $A^+$ is $N(\text{benzyl})H_3^+$.

Alternatively, $A^+$ is a polyatomic cation that includes a heterocyclyl or a heteroaryl, wherein each heterocyclyl or a heteroaryl contain a nitrogen atom that can be protonated. In one embodiment, $A^+$ is selected from piperidinium, morpholin-4-ium, thiomorpholin-4-ium, piperazin-1-ium, 4-methylpiperazin-1-ium, 4-phenyl-piperazin-1-ium, pyridinium, pyridazin-1-ium, pyrimidin-1-ium, pyrazin-1-ium, 1H-pyrrolium, 1H-pyrazol-1-ium, 1H-imidazol-1-ium, pyrazolidin-1-ium, pyrrolidinium, imidazolidin-1-ium, each optionally substituted with one to three groups represented by $R^4$. In a specific embodiment, $A^+$ is selected from:

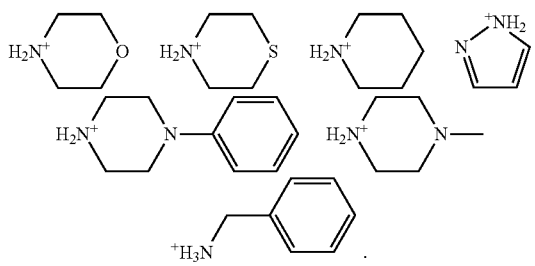

$R^1$ and $R^2$ are each independently (a) hydrogen; or (b) $(C_1-C_{10})$alkyl, $(C_2-C_{10})$alkenyl, $(C_2-C_{10})$alkynyl, aryl$(C_0-C_3)$alkyl, heteroaryl$(C_0-C_3)$alkyl, cycloalkyl$(C_0-C_3)$alkyl, heterocyclyl$(C_0-C_3)$alkyl, heteroaryl$(C_0-C_3)$alkyl, each optionally substituted with one to three groups represented by $R^4$; or $R^1$ and $R^2$, along with the nitrogen to which they are attached, form a monocyclic heterocyclyl, wherein the heterocyclyl formed may contain 0, 1 or 2 heteroatoms in addition to the nitrogen atom, wherein the heterocyclyl is optionally substituted by one or more groups selected from halogen, hydroxy, $(C_1-C_4)$alkyl, $(C_1-C_4)$alkoxy, or phenyl, wherein the $(C_1-C_4)$alkyl, $(C_1-C_4)$alkoxy, or phenyl is optionally substituted with halogen, hydroxy, $(C_1-C_4)$alkyl, or $(C_1-C_4)$alkoxy.

In a specific embodiment, $R^1$ and $R^2$, along with the nitrogen to which they are attached, form a heterocyclyl; and the heterocyclyl is selected from pyrrolidinyl, imidazolidinyl, pyrazolidinyl, dihydropyrrolyl, pyrrolyl, imidazolyl, pyrazolyl, triazolyl, oxazolidinyl, thiazolidinyl, oxazolyl, thiazolyl, piperidinyl, hydropyrimidinyl, piperazinyl, pyridinyl, pyridazinyl, pyrimidinyl, triazinyl, morpholinyl, and thiomorpholinyl, each of which is optionally substituted by halogen, hydroxy, $(C_1-C_4)$alkyl, $(C_1-C_4)$alkoxy, or phenyl. In a specific embodiment, $R^1$ and $R^2$, along with the nitrogen to which they are attached, form a heterocyclyl, and the heterocyclyl is selected from pyrazolyl, piperidinyl, piperazinyl, morpholinyl, and thiomorpholinyl, each of which is optionally substituted by halogen, hydroxy, $(C_1-C_4)$alkyl, $(C_1-C_4)$alkoxy, or phenyl. Specific substituents for the heterocyclyl formed include methyl and phenyl.

In an alternate embodiment, $R^1$ and $R^2$ are each independently (a) hydrogen; or (b) $(C_1-C_{10})$alkyl, $(C_2-C_{10})$alkenyl, $(C_2-C_{10})$alkynyl, aryl$(C_0-C_3)$alkyl, heteroaryl$(C_0-C_3)$alkyl, cycloalkyl$(C_0-C_3)$alkyl, heterocyclyl$(C_0-C_3)$alkyl, heteroaryl$(C_0-C_3)$alkyl, each optionally substituted with one to three groups represented by $R^4$. In a specific embodiment, $R^1$ and $R^2$ are each independently (a) hydrogen; or (b) $(C_1-C_4)$alkyl, $(C_2-C_4)$alkenyl, $(C_2-C_4)$alkynyl, $(C_3-C_8)$cycloalkyl, phenyl, benzyl, each optionally substituted with one to three groups represented by $R^4$. In a specific embodiment, $R^1$ and $R^2$ are the same. In an alternative specific embodiment, $R^1$ is different from $R^2$.

In a specific embodiment, $R^1$ is hydrogen and $R^2$ is selected from $(C_1-C_{10})$alkyl, $(C_2-C_{10})$alkenyl, $(C_2-C_{10})$alkynyl, aryl$(C_0-C_3)$alkyl, heteroaryl$(C_0-C_3)$alkyl, cycloalkyl$(C_0-C_3)$alkyl, heterocyclyl$(C_0-C_3)$alkyl, heteroaryl$(C_0-C_3)$alkyl, each optionally substituted with one to three groups represented by $R^4$. In another specific embodiment, $R^1$ is hydrogen or $(C_1-C_4)$alkyl; and $R^2$ is $(C_1-C_4)$alkyl or benzyl. In another specific embodiment, $R^1$ is hydrogen and $R^2$ is benzyl.

Each $R^3$ is independently selected from halogen, hydroxy, $(C_1-C_4)$alkyl, halo$(C_1-C_4)$alkyl, hydroxy$(C_1-C_4)$alkyl, $(C_1-C_4)$alkoxy, halo$(C_1-C_4)$alkoxy, and hydroxy$(C_1-C_4)$alkoxy. In a specific embodiment, $R^3$ is halogen, hydroxy, methyl, ethyl, propyl, isopropyl, butyl, t-butyl, hydroxy methyl, hydroxyethyl, hydroxymethyoxy, hydroxyethyoxy, methoxy, ethoxy, propoxy, butoxy, t-butyloxy, or $—CF_3$.

Each $R^4$ is independently selected from halogen, hydroxy, $(C_1-C_4)$alkyl, halo$(C_1-C_4)$alkyl, hydroxy$(C_1-C_4)$alkyl, $(C_1-C_4)$alkoxy, halo$(C_1-C_4)$alkoxy, and hydroxy$(C_1-C_4)$alkoxy. In a specific embodiment, $R^3$ is halogen, hydroxy, methyl, ethyl, propyl, isopropyl, butyl, t-butyl, hydroxy methyl, hydroxyethyl, hydroxymethyoxy, hydroxyethyoxy, methoxy, ethoxy, propoxy, butoxy, t-butyloxy, or $—CF_3$.

n is 0-3. In another specific embodiment, n is 0. In a specific embodiment n is 0 or 1. Alternatively, n is 1, 2 or 3. In a specific embodiment, n is 1. In another specific embodiment, n is 2. In yet another specific embodiment, n is 3.

In one embodiment of Structural Formula (I),

X is O or S and $A^+$ is present; or

X is Cl, OMs or OTs and $A^+$ is absent;

$A^+$ is a monovalent cation;

$R^1$ and $R^2$ are each independently (a) hydrogen; or (b) $(C_1-C_{10})$alkyl, $(C_2-C_{10})$alkenyl, $(C_2-C_{10})$alkynyl, aryl$(C_0-C_3)$alkyl, heteroaryl$(C_0-C_3)$alkyl, cycloalkyl$(C_0-C_3)$alkyl, heterocyclyl$(C_0-C_3)$alkyl, heteroaryl$(C_0-C_3)$alkyl, each optionally substituted with one to three groups represented by $R^4$; or $R^1$ and $R^2$, along with the nitrogen to which they are attached, form a monocyclic heterocyclyl, wherein the heterocyclyl formed may contain 0, 1 or 2 heteroatoms in addition to the nitrogen atom, wherein the heterocyclyl is optionally substituted by one or more groups selected from halogen, hydroxy, $(C_1-C_4)$alkyl, $(C_1-C_4)$alkoxy, or phenyl, wherein the $(C_1-C_4)$alkyl, $(C_1-C_4)$alkoxy, or phenyl is optionally substituted with halogen, hydroxy, $(C_1-C_4)$alkyl, or $(C_1-C_4)$alkoxy;

Each $R^3$ is independently selected from halogen, hydroxy, $(C_1-C_4)$alkyl, halo$(C_1-C_4)$alkyl, hydroxy$(C_1-C_4)$alkyl, $(C_1-C_4)$alkoxy, halo$(C_1-C_4)$alkoxy, and hydroxy$(C_1-C_4)$alkoxy;

Each $R^4$ is independently selected from halogen, hydroxy, $(C_1-C_4)$alkyl, halo$(C_1-C_4)$alkyl, hydroxy$(C_1-C_4)$alkyl, $(C_1-C_4)$alkoxy, halo$(C_1-C_4)$alkoxy, and hydroxy$(C_1-C_4)$alkoxy; and n is 0-3;

or a pharmaceutically acceptable salt thereof.

In a first specific embodiment of Structural Formula (I)
X is S;
$A^+$ is selected from lithium, sodium or potassium. Specifically, $A^+$ is potassium. Alternatively, $A^+$ is $H^+$.

$R^1$ and $R^2$ are each independently (a) hydrogen; or (b) $(C_1-C_{10})$alkyl, $(C_2-C_{10})$alkenyl, $(C_2-C_{10})$alkynyl, aryl$(C_0-C_3)$alkyl, heteroaryl$(C_0-C_3)$alkyl, cycloalkyl$(C_0-C_3)$alkyl, heterocyclyl$(C_0-C_3)$alkyl, heteroaryl$(C_0-C_3)$alkyl, each optionally substituted with one to three groups represented by $R^4$. Specifically, $R^1$ and $R^2$ are each independently (a) hydrogen; or (b) $(C_1-C_4)$alkyl, $(C_2-C_4)$alkenyl, $(C_2-C_4)$alkynyl, $(C_3-C_8)$cycloalkyl, phenyl, benzyl, each optionally substituted with one to three groups represented by $R^4$. More specifically, $R^1$ is hydrogen or $(C_1-C_4)$alkyl; and $R^2$ is $(C_1-C_4)$alkyl or benzyl. Even more specifically, $R^1$ is hydrogen and $R^2$ is benzyl, or a pharmaceutically acceptable salt thereof, and the values and specific values of the remainder of the variables are as described for Structural Formula (I).

In a second specific embodiment of Structural Formula (I)
X is S;
$A^+$ is selected from $NH_4^+$, $N(C_1-C_4 alkyl)H_3^+$ (for example, $N(methyl)H_3^+$ or $N(ethyl)H_3^+$), $N(benzyl)H_3^+$, and $N(phenyl)H_3^+$. Specifically, $A^+$ is $N(benzyl)H_3^+$.

$R^1$ and $R^2$ are each independently (a) hydrogen; or (b) $(C_1-C_{10})$alkyl, $(C_2-C_{10})$alkenyl, $(C_2-C_{10})$alkynyl, aryl$(C_0-C_3)$alkyl, heteroaryl$(C_0-C_3)$alkyl, cycloalkyl$(C_0-C_3)$alkyl, heterocyclyl$(C_0-C_3)$alkyl, heteroaryl$(C_0-C_3)$alkyl, each optionally substituted with one to three groups represented by $R^4$. Specifically, $R^1$ and $R^2$ are each independently (a) hydrogen; or (b) $(C_1-C_4)$alkyl, $(C_2-C_4)$alkenyl, $(C_2-C_4)$alkynyl, $(C_3-C_8)$cycloalkyl, phenyl, benzyl, each optionally substituted with one to three groups represented by $R^4$. More specifically, $R^1$ is hydrogen or $(C_1-C_4)$alkyl; and $R^2$ is $(C_1-C_4)$alkyl or benzyl. Even more specifically, $R^1$ is hydrogen and $R^2$ is benzyl, or a pharmaceutically acceptable salt thereof, and the values and specific values of the remainder of the variables are as described for Structural Formula (I).

In a third specific embodiment of Structural Formula (I)
X is S;
$A^+$ is selected from piperidinium, morpholin-4-ium, thiomorpholin-4-ium, piperazin-1-ium, 4-methylpiperazin-1-ium, 4-phenyl-piperazin-1-ium, pyridinium, pyridazin-1-ium, pyrimidin-1-ium, pyrazin-1-ium, 1H-pyrrolium, 1H-pyrazol-1-ium, 1H-imidazol-1-ium, pyrazolidin-1-ium, pyrrolidinium, imidazolidin-1-ium. Specifically, $A^+$ is selected from:

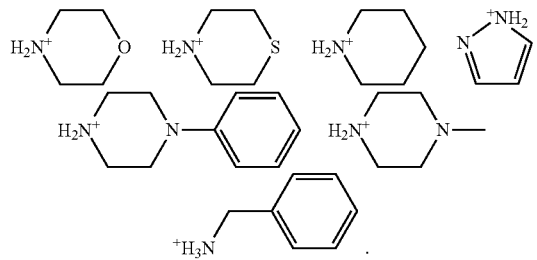

$R^1$ and $R^2$ are each independently (a) hydrogen; or (b) $(C_1-C_{10})$alkyl, $(C_2-C_{10})$alkenyl, $(C_2-C_{10})$alkynyl, aryl$(C_0-C_3)$alkyl, heteroaryl$(C_0-C_3)$alkyl, cycloalkyl$(C_0-C_3)$alkyl, heterocyclyl$(C_0-C_3)$alkyl, heteroaryl$(C_0-C_3)$alkyl, each optionally substituted with one to three groups represented by $R^4$. Specifically, $R^1$ and $R^2$ are each independently (a) hydrogen; or (b) $(C_1-C_4)$alkyl, $(C_2-C_4)$alkenyl, $(C_2-C_4)$alkynyl, $(C_3-C_8)$cycloalkyl, phenyl, benzyl, each optionally substituted with one to three groups represented by $R^4$. More specifically, $R^1$ is hydrogen or $(C_1-C_4)$alkyl; and $R^2$ is $(C_1-C_4)$alkyl or benzyl. Even more specifically, $R^1$ is hydrogen and $R^2$ is benzyl, or a pharmaceutically acceptable salt thereof, and the values and specific values of the remainder of the variables are as described for Structural Formula (I).

In a fourth specific embodiment of Structural Formula (I)
X is S;
$A^+$ is selected from lithium, sodium or potassium. Specifically, $A^+$ is potassium. Alternatively, $A^+$ is $H^+$.

$R^1$ and $R^2$, along with the nitrogen to which they are attached, form a monocyclic heterocyclyl, wherein the heterocyclyl formed may contain 0, 1 or 2 heteroatoms in addition to the nitrogen atom, wherein the heterocyclyl is optionally substituted by one or more groups selected from halogen, hydroxy, $(C_1-C_4)$alkyl, $(C_1-C_4)$alkoxy, or phenyl, wherein the $(C_1-C_4)$alkyl, $(C_1-C_4)$alkoxy, or phenyl is optionally substituted with halogen, hydroxy, $(C_1-C_4)$alkyl, or $(C_1-C_4)$alkoxy.

Specifically, $R^1$ and $R^2$, along with the nitrogen to which they are attached, form a heterocyclyl; and the heterocyclyl is selected from pyrrolidinyl, imidazolidinyl, pyrazolidinyl, dihydropyrrolyl, pyrrolyl, imidazolyl, pyrazolyl, triazolyl, oxazolidinyl, thiazolidinyl, oxazolyl, thiazolyl, piperidinyl, hydropyrimidinyl, piperazinyl, pyridinyl, pyridazinyl, pyrimidinyl, triazinyl, morpholinyl, and thiomorpholinyl, each of which is optionally substituted by halogen, hydroxy, $(C_1-C_4)$alkyl, $(C_1-C_4)$alkoxy, or phenyl. Even more specifically, $R^1$ and $R^2$, along with the nitrogen to which they are attached, form a heterocyclyl; and the heterocyclyl is selected from pyrazolyl, piperidinyl, piperazinyl, morpholinyl, and thiomorpholinyl, each of which is optionally substituted by halogen, hydroxy, $(C_1-C_4)$alkyl, $(C_1-C_4)$alkoxy, or phenyl, or a pharmaceutically acceptable salt thereof, and the values and specific values of the remainder of the variables are as described for Structural Formula (I).

In a fifth specific embodiment of Structural Formula (I)
X is S;
$A^+$ is selected from $NH_4^+$, $N(C_1-C_4 alkyl)H_3^+$ (for example, $N(methyl)H_3^+$ or $N(ethyl)H_3^+$), $N(benzyl)H_3^+$, and $N(phenyl)H_3^+$. Specifically, $A^+$ is $N(benzyl)H_3^+$.

$R^1$ and $R^2$, along with the nitrogen to which they are attached, form a monocyclic heterocyclyl, wherein the heterocyclyl formed may contain 0, 1 or 2 heteroatoms in addition to the nitrogen atom, wherein the heterocyclyl is optionally substituted by one or more groups selected from halogen, hydroxy, $(C_1-C_4)$alkyl, $(C_1-C_4)$alkoxy, or phenyl, wherein the $(C_1-C_4)$alkyl, $(C_1-C_4)$alkoxy, or phenyl is optionally substituted with halogen, hydroxy, $(C_1-C_4)$alkyl, or $(C_1-C_4)$alkoxy.

Specifically, $R^1$ and $R^2$, along with the nitrogen to which they are attached, form a heterocyclyl; and the heterocyclyl is selected from pyrrolidinyl, imidazolidinyl, pyrazolidinyl, dihydropyrrolyl, pyrrolyl, imidazolyl, pyrazolyl, triazolyl, oxazolidinyl, thiazolidinyl, oxazolyl, thiazolyl, piperidinyl, hydropyrimidinyl, piperazinyl, pyridinyl, pyridazinyl, pyrimidinyl, triazinyl, morpholinyl, and thiomorpholinyl, each of which is optionally substituted by halogen, hydroxy, $(C_1-C_4)$alkyl, $(C_1-C_4)$alkoxy, or phenyl. Even more specifically, $R^1$ and $R^2$, along with the nitrogen to which they are attached, form a heterocyclyl; and the heterocyclyl is selected from pyrazolyl, piperidinyl, piperazinyl, morpholinyl, and thiomorpholinyl, each of which is optionally substituted by halogen, hydroxy, $(C_1-C_4)$alkyl, $(C_1-C_4)$alkoxy, or phenyl, or a pharmaceutically acceptable salt thereof, and the values and specific values of the remainder of the variables are as described for Structural Formula (I).

In a sixth specific embodiment of Structural Formula (I) X is S;

A⁺ is selected from piperidinium, morpholin-4-ium, thiomorpholin-4-ium, piperazin-1-ium, 4-methylpiperazin-1-ium, 4-phenyl-piperazin-1-ium, pyridinium, pyridazin-1-ium, pyrimidin-1-ium, pyrazin-1-ium, 1H-pyrrolium, 1H-pyrazol-1-ium, 1H-imidazol-1-ium, pyrazolidin-1-ium, pyrrolidinium, imidazolidin-1-ium. Specifically, A⁺ is selected from:

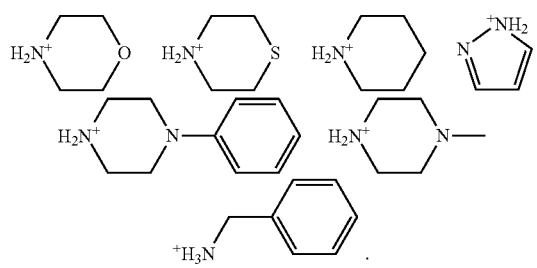

$R^1$ and $R^2$, along with the nitrogen to which they are attached, form a monocyclic heterocyclyl, wherein the heterocyclyl formed may contain 0, 1 or 2 heteroatoms in addition to the nitrogen atom, wherein the heterocyclyl is optionally substituted by one or more groups selected from halogen, hydroxy, ($C_1$-$C_4$)alkyl, ($C_1$-$C_4$)alkoxy, or phenyl, wherein the ($C_1$-$C_4$)alkyl, ($C_1$-$C_4$)alkoxy, or phenyl is optionally substituted with halogen, hydroxy, ($C_1$-$C_4$)alkyl, or ($C_1$-$C_4$)alkoxy.

Specifically, $R^1$ and $R^2$, along with the nitrogen to which they are attached, form a heterocyclyl; and the heterocyclyl is selected from pyrrolidinyl, imidazolidinyl, pyrazolidinyl, dihydropyrrolyl, pyrrolyl, imidazolyl, pyrazolyl, triazolyl, oxazolidinyl, thiazolidinyl, oxazolyl, thiazolyl, piperidinyl, hydropyrimidinyl, piperazinyl, pyridinyl, pyridazinyl, pyrimidinyl, triazinyl, morpholinyl, and thiomorpholinyl, each of which is optionally substituted by halogen, hydroxy, ($C_1$-$C_4$)alkyl, ($C_1$-$C_4$)alkoxy, or phenyl. Even more specifically, $R^1$ and $R^2$, along with the nitrogen to which they are attached, form a heterocyclyl; and the heterocyclyl is selected from pyrazolyl, piperidinyl, piperazinyl, morpholinyl, and thiomorpholinyl, each of which is optionally substituted by halogen, hydroxy, ($C_1$-$C_4$)alkyl, ($C_1$-$C_4$)alkoxy, or phenyl, or a pharmaceutically acceptable salt thereof, and the values and specific values of the remainder of the variables are as described for Structural Formula (I).

In a seventh specific embodiment of Structural Formula (I) X is O;

A⁺ is selected from lithium, sodium or potassium. Specifically, A⁺ is potassium. Alternatively, A⁺ is H⁺.

$R^1$ and $R^2$, along with the nitrogen to which they are attached, form a monocyclic heterocyclyl, wherein the heterocyclyl formed may contain 0, 1 or 2 heteroatoms in addition to the nitrogen atom, wherein the heterocyclyl is optionally substituted by one or more groups selected from halogen, hydroxy, ($C_1$-$C_4$)alkyl, ($C_1$-$C_4$)alkoxy, or phenyl, wherein the ($C_1$-$C_4$)alkyl, ($C_1$-$C_4$)alkoxy, or phenyl is optionally substituted with halogen, hydroxy, ($C_1$-$C_4$)alkyl, or ($C_1$-$C_4$)alkoxy.

Specifically, $R^1$ and $R^2$, along with the nitrogen to which they are attached, form a heterocyclyl; and the heterocyclyl is selected from pyrrolidinyl, imidazolidinyl, pyrazolidinyl, dihydropyrrolyl, pyrrolyl, imidazolyl, pyrazolyl, triazolyl, oxazolidinyl, thiazolidinyl, oxazolyl, thiazolyl, piperidinyl, hydropyrimidinyl, piperazinyl, pyridinyl, pyridazinyl, pyrimidinyl, triazinyl, morpholinyl, and thiomorpholinyl, each of which is optionally substituted by halogen, hydroxy, ($C_1$-$C_4$) alkyl, ($C_1$-$C_4$)alkoxy, or phenyl. Even more specifically, $R^1$ and $R^2$, along with the nitrogen to which they are attached, form a heterocyclyl; and the heterocyclyl is selected from pyrazolyl, piperidinyl, piperazinyl, morpholinyl, and thiomorpholinyl, each of which is optionally substituted by halogen, hydroxy, ($C_1$-$C_4$)alkyl, ($C_1$-$C_4$)alkoxy, or phenyl, or a pharmaceutically acceptable salt thereof, and the values and specific values of the remainder of the variables are as described for Structural Formula (I).

Another embodiment is method of administering hydrogen sulfide ($H_2S$) slowly and sustainably to an individual in need thereof comprising administering an effective amount of compound represented by a one of the following structural formulas:

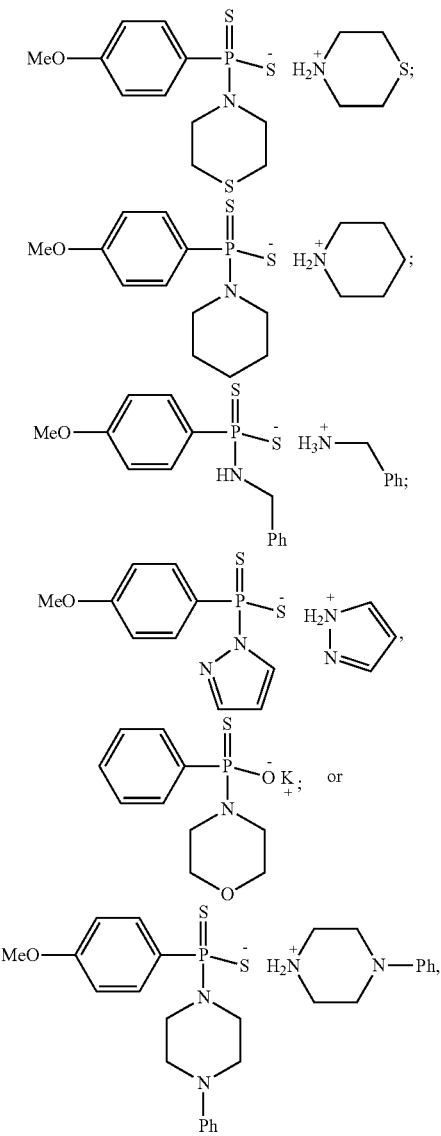

or a pharmaceutically acceptable salt thereof.

Another embodiment is method of administering hydrogen sulfide ($H_2S$) slowly and sustainably to an individual in need thereof comprising administering an effective amount of morpholin-4-ium 4 methoxyphenyl(morpholino)phosphinodithioate (GYY4137) to the individual.

Morpholin-4-ium 4 methoxyphenyl(morpholino)phosphinodithioate, also referred to herein as GYY4137, is represented by the following structural formula:

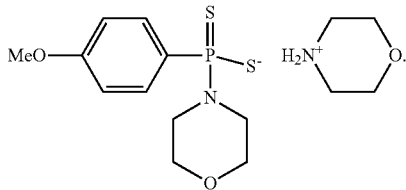 [SMILES: COc1ccc(P(=S)([S-])N2CCOCC2)cc1 ; C1COCC[NH2+]1]

In an eighth specific embodiment of Structural Formula (I), the compound is represented by following Structural Formula (II):

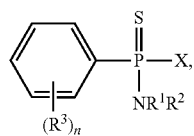

(II)

wherein

X is halogen, OMs or OTs. In a specific embodiment, X is Cl, OMs or OTs. In another specific embodiment, X is Cl. Alternatively, X is OMs. Alternatively, X is OTs.

$R^1$ and $R^2$ are each independently (a) hydrogen; or (b) $(C_1-C_{10})$alkyl, $(C_2-C_{10})$alkenyl, $(C_2-C_{10})$alkynyl, aryl$(C_0-C_3)$alkyl, heteroaryl$(C_0-C_3)$alkyl, cycloalkyl$(C_0-C_3)$alkyl, heterocyclyl$(C_0-C_3)$alkyl, heteroaryl$(C_0-C_3)$alkyl, each optionally substituted with one to three groups represented by $R^4$; or $R^1$ and $R^2$, along with the nitrogen to which they are attached, form a monocyclic heterocyclyl, wherein the heterocyclyl formed may contain 0, 1 or 2 heteroatoms in addition to the nitrogen atom, wherein the heterocyclyl is optionally substituted by one or more groups selected from halogen, hydroxy, $(C_1-C_4)$alkyl, $(C_1-C_4)$alkoxy, or phenyl, wherein the $(C_1-C_4)$alkyl, $(C_1-C_4)$alkoxy, or phenyl is optionally substituted with halogen, hydroxy, $(C_1-C_4)$alkyl, or $(C_1-C_4)$alkoxy.

In a specific embodiment, $R^1$ and $R^2$, along with the nitrogen to which they are attached, form a heterocyclyl, wherein the heterocyclyl is selected from pyrrolidinyl, imidazolidinyl, pyrazolidinyl, dihydropyrrolyl, pyrrolyl, imidazolyl, pyrazolyl, triazolyl, oxazolidinyl, thiazolidinyl, oxazolyl, thiazolyl, piperidinyl, hydropyrimidinyl, piperazinyl, pyridinyl, pyridazinyl, pyrimidinyl, triazinyl, morpholinyl, and thiomorpholinyl, each of which is optionally substituted by halogen, hydroxy, $(C_1-C_4)$alkyl, $(C_1-C_4)$alkoxy, or phenyl. In a specific embodiment, $R^1$ and $R^2$, along with the nitrogen to which they are attached, form a heterocyclyl, wherein the heterocyclyl is selected from pyrazolyl, piperidinyl, piperazinyl, morpholinyl, and thiomorpholinyl, each of which is optionally substituted by halogen, hydroxy, $(C_1-C_4)$alkyl, $(C_1-C_4)$alkoxy, or phenyl.

In an alternate embodiment, $R^1$ and $R^2$ are each independently (a) hydrogen; or (b) $(C_1-C_{10})$alkyl, $(C_2-C_{10})$alkenyl, $(C_2-C_{10})$alkynyl, aryl$(C_0-C_3)$alkyl, heteroaryl$(C_0-C_3)$alkyl, cycloalkyl$(C_0-C_3)$alkyl, heterocyclyl$(C_0-C_3)$alkyl, heteroaryl$(C_0-C_3)$alkyl, each optionally substituted with one to three groups represented by $R^4$. In a specific embodiment, $R^1$ and $R^2$ are each independently (a) hydrogen; or (b) $(C_1-C_4)$alkyl, $(C_2-C_4)$alkenyl, $(C_2-C_4)$alkynyl, $(C_3-C_8)$cycloalkyl, phenyl, benzyl, each optionally substituted with one to three groups represented by $R^4$. In a specific embodiment, $R^1$ and $R^2$ are the same. In an alternative specific embodiment, $R^1$ is different from $R^2$.

In a specific embodiment, $R^1$ is hydrogen and $R^2$ is selected from $(C_1-C_{10})$alkyl, $(C_2-C_{10})$alkenyl, $(C_2-C_{10})$alkynyl, aryl$(C_0-C_3)$alkyl, heteroaryl$(C_0-C_3)$alkyl, cycloalkyl$(C_0-C_3)$alkyl, heterocyclyl$(C_0-C_3)$alkyl, heteroaryl$(C_0-C_3)$alkyl, each optionally substituted with one to three groups represented by $R^4$. In another specific embodiment, $R^1$ is hydrogen or $(C_1-C_4)$alkyl; and $R^2$ is $(C_1-C_4)$alkyl or benzyl. In another specific embodiment, $R^1$ is hydrogen and $R^2$ is benzyl.

Each $R^3$ is independently selected from halogen, hydroxy, $(C_1-C_4)$alkyl, halo$(C_1-C_4)$alkyl, hydroxy$(C_1-C_4)$alkyl, $(C_1-C_4)$alkoxy, halo$(C_1-C_4)$alkoxy, and hydroxy$(C_1-C_4)$alkoxy. In a specific embodiment, $R^3$ is halogen, hydroxy, methyl, ethyl, propyl, isopropyl, butyl, t-butyl, hydroxy methyl, hydroxyethyl, hydroxymethyoxy, hydroxyethyoxy, methoxy, ethoxy, propoxy, butoxy, t-butyloxy, or —$CF_3$.

Each $R^4$ is independently selected from halogen, hydroxy, $(C_1-C_4)$alkyl, halo$(C_1-C_4)$alkyl, hydroxy$(C_1-C_4)$alkyl, $(C_1-C_4)$alkoxy, halo$(C_1-C_4)$alkoxy, and hydroxy$(C_1-C_4)$alkoxy. In a specific embodiment, $R^3$ is halogen, hydroxy, methyl, ethyl, propyl, isopropyl, butyl, t-butyl, hydroxy methyl, hydroxyethyl, hydroxymethyoxy, hydroxyethyoxy, methoxy, ethoxy, propoxy, butoxy, t-butyloxy, or —$CF_3$.

n is 0-3. In another specific embodiment, n is 0. In a specific embodiment m is 0 or 1. Alternatively, n is 1, 2 or 3. In a specific embodiment, n is 1. In another specific embodiment, n is 2. In yet another specific embodiment, n is 3.

In a first specific embodiment of Structural Formula (II)

X is Cl;

$R^1$ and $R^2$ are each independently (a) hydrogen; or (b) $(C_1-C_{10})$alkyl, $(C_2-C_{10})$alkenyl, $(C_2-C_{10})$alkynyl, aryl$(C_0-C_3)$alkyl, heteroaryl$(C_0-C_3)$alkyl, cycloalkyl$(C_0-C_3)$alkyl, heterocyclyl$(C_0-C_3)$alkyl, heteroaryl$(C_0-C_3)$alkyl, each optionally substituted with one to three groups represented by $R^4$. Specifically, $R^1$ and $R^2$ are each independently (a) hydrogen; or (b) $(C_1-C_4)$alkyl, $(C_2-C_4)$alkenyl, $(C_2-C_4)$alkynyl, $(C_3-C_8)$cycloalkyl, phenyl, benzyl, each optionally substituted with one to three groups represented by $R^4$. More specifically, $R^1$ is hydrogen or $(C_1-C_4)$alkyl; and $R^2$ is $(C_1-C_4)$alkyl or benzyl. Even more specifically, $R^1$ is hydrogen and $R^2$ is benzyl, or a pharmaceutically acceptable salt thereof, and the values and specific values of the remainder of the variables are as described for Structural Formula (II).

In a second specific embodiment of Structural Formula (II)

X is Cl;

$R^1$ and $R^2$, along with the nitrogen to which they are attached, form a monocyclic heterocyclyl, wherein the heterocyclyl formed may contain 0, 1 or 2 heteroatoms in addition to the nitrogen atom, wherein the heterocyclyl is optionally substituted by one or more groups selected from halogen, hydroxy, $(C_1-C_4)$alkyl, $(C_1-C_4)$alkoxy, or phenyl, wherein the $(C_1-C_4)$alkyl, $(C_1-C_4)$alkoxy, or phenyl is optionally substituted with halogen, hydroxy, $(C_1-C_4)$alkyl, or $(C_1-C_4)$alkoxy.

Specifically, $R^1$ and $R^2$, along with the nitrogen to which they are attached, form a heterocyclyl; and the heterocyclyl is selected from pyrrolidinyl, imidazolidinyl, pyrazolidinyl, dihydropyrrolyl, pyrrolyl, imidazolyl, pyrazolyl, triazolyl, oxazolidinyl, thiazolidinyl, oxazolyl, thiazolyl, piperidinyl, hydropyrimidinyl, piperazinyl, pyridinyl, pyridazinyl, pyrimidinyl, triazinyl, morpholinyl, and thiomorpholinyl, each of which is optionally substituted by halogen, hydroxy, $(C_1-C_4)$alkyl, $(C_1-C_4)$alkoxy, or phenyl. Even more specifically, $R^1$ and $R^2$, along with the nitrogen to which they are attached, form a heterocyclyl; and the heterocyclyl is selected from pyrazolyl, piperidinyl, piperazinyl, morpholinyl, and thiomorpholinyl, each of which is optionally substituted by halogen, hydroxy, $(C_1-C_4)$alkyl, $(C_1-C_4)$alkoxy, or phenyl, or a pharmaceutically acceptable salt thereof, and the values and specific values of the remainder of the variables are as described for Structural Formula (II).

In a third specific embodiment of Structural Formula (II) X is OMs;
$R^1$ and $R^2$ are each independently (a) hydrogen; or (b) $(C_1-C_{10})$alkyl, $(C_2-C_{10})$alkenyl, $(C_2-C_{10})$alkynyl, aryl$(C_0-C_3)$alkyl, heteroaryl$(C_0-C_3)$alkyl, cycloalkyl$(C_0-C_3)$alkyl, heterocyclyl$(C_0-C_3)$alkyl, heteroaryl$(C_0-C_3)$alkyl, each optionally substituted with one to three groups represented by $R^4$. Specifically, $R^1$ and $R^2$ are each independently (a) hydrogen; or (b) $(C_1-C_4)$alkyl, $(C_2-C_4)$alkenyl, $(C_2-C_4)$alkynyl, $(C_3-C_8)$cycloalkyl, phenyl, benzyl, each optionally substituted with one to three groups represented by $R^4$. More specifically, $R^1$ is hydrogen or $(C_1-C_4)$alkyl; and $R^2$ is $(C_1-C_4)$alkyl or benzyl. Even more specifically, $R^1$ is hydrogen and $R^2$ is benzyl, or a pharmaceutically acceptable salt thereof, and the values and specific values of the remainder of the variables are as described for Structural Formula (II).

In a fourth specific embodiment of Structural Formula (II) X is OMs;
$R^1$ and $R^2$, along with the nitrogen to which they are attached, form a monocyclic heterocyclyl, wherein the heterocyclyl formed may contain 0, 1 or 2 heteroatoms in addition to the nitrogen atom, wherein the heterocyclyl is optionally substituted by one or more groups selected from halogen, hydroxy, $(C_1-C_4)$alkyl, $(C_1-C_4)$alkoxy, or phenyl, wherein the $(C_1-C_4)$alkyl, $(C_1-C_4)$alkoxy, or phenyl is optionally substituted with halogen, hydroxy, $(C_1-C_4)$alkyl, or $(C_1-C_4)$alkoxy.

Specifically, $R^1$ and $R^2$, along with the nitrogen to which they are attached, form a heterocyclyl; and the heterocyclyl is selected from pyrrolidinyl, imidazolidinyl, pyrazolidinyl, dihydropyrrolyl, pyrrolyl, imidazolyl, pyrazolyl, triazolyl, oxazolidinyl, thiazolidinyl, oxazolyl, thiazolyl, piperidinyl, hydropyrimidinyl, piperazinyl, pyridinyl, pyridazinyl, pyrimidinyl, triazinyl, morpholinyl, and thiomorpholinyl, each of which is optionally substituted by halogen, hydroxy, $(C_1-C_4)$alkyl, $(C_1-C_4)$alkoxy, or phenyl. Even more specifically, $R^1$ and $R^2$, along with the nitrogen to which they are attached, form a heterocyclyl; and the heterocyclyl is selected from pyrazolyl, piperidinyl, piperazinyl, morpholinyl, and thiomorpholinyl, each of which is optionally substituted by halogen, hydroxy, $(C_1-C_4)$alkyl, $(C_1-C_4)$alkoxy, or phenyl, or a pharmaceutically acceptable salt thereof, and the values and specific values of the remainder of the variables are as described for Structural Formula (II).

In a fifth specific embodiment of Structural Formula (II) X is OTs;
$R^1$ and $R^2$ are each independently (a) hydrogen; or (b) $(C_1-C_{10})$alkyl, $(C_2-C_{10})$alkenyl, $(C_2-C_{10})$alkynyl, aryl$(C_0-C_3)$alkyl, heteroaryl$(C_0-C_3)$alkyl, cycloalkyl$(C_0-C_3)$alkyl, heterocyclyl$(C_0-C_3)$alkyl, heteroaryl$(C_0-C_3)$alkyl, each optionally substituted with one to three groups represented by $R^4$. Specifically, $R^1$ and $R^2$ are each independently (a) hydrogen; or (b) $(C_1-C_4)$alkyl, $(C_2-C_4)$alkenyl, $(C_2-C_4)$alkynyl, $(C_3-C_8)$cycloalkyl, phenyl, benzyl, each optionally substituted with one to three groups represented by $R^4$. More specifically, $R^1$ is hydrogen or $(C_1-C_4)$alkyl; and $R^2$ is $(C_1-C_4)$alkyl or benzyl. Even more specifically, $R^1$ is hydrogen and $R^2$ is benzyl, or a pharmaceutically acceptable salt thereof, and the values and specific values of the remainder of the variables are as described for Structural Formula (II).

In a sixth specific embodiment of Structural Formula (II) X is OTs;
$R^1$ and $R^2$, along with the nitrogen to which they are attached, form a monocyclic heterocyclyl, wherein the heterocyclyl formed may contain 0, 1 or 2 heteroatoms in addition to the nitrogen atom, wherein the heterocyclyl is optionally substituted by one or more groups selected from halogen, hydroxy, $(C_1-C_4)$alkyl, $(C_1-C_4)$alkoxy, or phenyl, wherein the $(C_1-C_4)$alkyl, $(C_1-C_4)$alkoxy, or phenyl is optionally substituted with halogen, hydroxy, $(C_1-C_4)$alkyl, or $(C_1-C_4)$alkoxy.

Specifically, $R^1$ and $R^2$, along with the nitrogen to which they are attached, form a heterocyclyl; and the heterocyclyl is selected from pyrrolidinyl, imidazolidinyl, pyrazolidinyl, dihydropyrrolyl, pyrrolyl, imidazolyl, pyrazolyl, triazolyl, oxazolidinyl, thiazolidinyl, oxazolyl, thiazolyl, piperidinyl, hydropyrimidinyl, piperazinyl, pyridinyl, pyridazinyl, pyrimidinyl, triazinyl, morpholinyl, and thiomorpholinyl, each of which is optionally substituted by halogen, hydroxy, $(C_1-C_4)$alkyl, $(C_1-C_4)$alkoxy, or phenyl. Even more specifically, $R^1$ and $R^2$, along with the nitrogen to which they are attached, form a heterocyclyl; and the heterocyclyl is selected from pyrazolyl, piperidinyl, piperazinyl, morpholinyl, and thiomorpholinyl, each of which is optionally substituted by halogen, hydroxy, $(C_1-C_4)$alkyl, $(C_1-C_4)$alkoxy, or phenyl, or a pharmaceutically acceptable salt thereof, and the values and specific values of the remainder of the variables are as described for Structural Formula (II).

In a specific embodiment, the Structural Formula (II) is represented by the following structure:

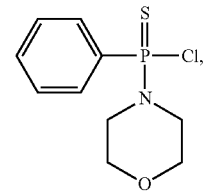 [SMILES: S=P(Cl)(c1ccccc1)N1CCOCC1]

or a pharmaceutically acceptable salt thereof.

Certain of the disclosed compounds may exist in various stereoisomeric forms. Stereoisomers are compounds that differ only in their spatial arrangement. Enantiomers are pairs of stereoisomers whose mirror images are not superimposable, most commonly because they contain an asymmetrically substituted carbon atom that acts as a chiral center. "Enantiomer" means one of a pair of molecules that are mirror images of each other and are not superimposable. Diastereomers are stereoisomers that are not related as mirror images, most commonly because they contain two or more asymmetrically substituted carbon atoms. The symbol "*" in a structural formula represents the presence of a chiral carbon center. "R" and "S" represent the configuration of substituents around one or more chiral carbon atoms. Thus, "R*" and "S*" denote the relative configurations of substituents around one or more chiral carbon atoms.

"Racemate" or "racemic mixture" means a compound of equimolar quantities of two enantiomers, wherein such mixtures exhibit no optical activity; i.e., they do not rotate the plane of polarized light.

"Geometric isomer" means isomers that differ in the orientation of substituent atoms in relationship to a carbon-carbon double bond, to a cycloalkyl ring, or to a bridged bicyclic system. Atoms (other than H) on each side of a carbon-carbon double bond may be in an E (substituents are on opposite sides of the carbon-carbon double bond) or Z (substituents are oriented on the same side) configuration.

"R," "S," "S*," "R*," "E," "Z," "cis," and "trans," indicate configurations relative to the core molecule.

The compounds of the invention may be prepared as individual isomers by either isomer-specific synthesis or resolved from an isomeric mixture. Conventional resolution techniques include forming the salt of a free base of each isomer of an isomeric pair using an optically active acid (followed by fractional crystallization and regeneration of the free base), forming the salt of the acid form of each isomer of an isomeric pair using an optically active amine (followed by fractional crystallization and regeneration of the free acid), forming an ester or amide of each of the isomers of an isomeric pair using an optically pure acid, amine or alcohol (followed by chromatographic separation and removal of the chiral auxiliary), or resolving an isomeric mixture of either a starting material or a final product using various well known chromatographic methods.

When the stereochemistry of a disclosed compound is named or depicted by structure, the named or depicted stereoisomer is at least 60%, 70%, 80%, 90%, 99% or 99.9% by weight pure relative to the other stereoisomers. When a single enantiomer is named or depicted by structure, the depicted or named enantiomer is at least 60%, 70%, 80%, 90%, 99% or 99.9% by weight optically pure. Percent optical purity by weight is the ratio of the weight of the enantiomer over the weight of the enantiomer plus the weight of its optical isomer.

When a disclosed compound is named or depicted by structure without indicating the stereochemistry, and the compound has at least one chiral center, it is to be understood that the name or structure encompasses one enantiomer of compound free from the corresponding optical isomer, a racemic mixture of the compound and mixtures enriched in one enantiomer relative to its corresponding optical isomer.

When a disclosed compound is named or depicted by structure without indicating the stereochemistry and has at least two chiral centers, it is to be understood that the name or structure encompasses a diastereomer free of other diastereomers, a pair of diastereomers free from other diastereomeric pairs, mixtures of diastereomers, mixtures of diastereomeric pairs, mixtures of diastereomers in which one diastereomer is enriched relative to the other diastereomer(s) and mixtures of diastereomeric pairs in which one diastereomeric pair is enriched relative to the other diastereomeric pair(s).

The compounds of the invention may be present in the form of pharmaceutically acceptable salts. For use in medicines, the salts of the compounds of the invention refer to non-toxic "pharmaceutically acceptable salts." Pharmaceutically acceptable salt forms include pharmaceutically acceptable acidic/anionic or basic/cationic salts.

Pharmaceutically acceptable acidic/anionic salts include, the acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrobromide, hydrochloride, hydroxynaphthoate, iodide, isethionate, lactate, lactobionate, malate, maleate, malonate, mandelate, mesylate, methylsulfate, mucate, napsylate, nitrate, pamoate, pantothenate, phosphate/diphospate, polygalacturonate, salicylate, stearate, subacetate, succinate, sulfate, hydrogensulfate, tannate, tartrate, teoclate, tosylate, and triethiodide salts.

Pharmaceutically acceptable basic/cationic salts include, the sodium, potassium, calcium, magnesium, diethanolamine, N-methyl-D-glucamine, L-lysine, L-arginine, ammonium, ethanolamine, piperazine and triethanolamine salts.

As used herein an "individual" refers to an animal, and in a particular aspect, a mammal. Examples of mammals include primates, a canine, a feline, a rodent, and the like. Specific examples include humans, dogs, cats, horses, cows, sheep, goats, rabbits, guinea pigs, rats and mice.

The term "individual in need thereof" refers to an individual who is in need of treatment or prophylaxis as determined by a researcher, veterinarian, medical doctor or other clinician. In one embodiment, an individual in need thereof is a mammal, such as a human.

The need or desire for administration according to the methods of the present invention is determined via the use of well known risk factors. The effective amount of a (one or more) particular compound is determined, in the final analysis, by the physician in charge of the case, but depends on factors such as the exact disease to be treated, the severity of the disease and other diseases or conditions from which the patient suffers, the chosen route of administration, other drugs and treatments which the patient may concomitantly require, and other factors in the physician's judgment.

As used herein, "effective amount" or "therapeutically effective amount" means an amount of the active compound that will elicit the desired biological or medical response in a tissue, system, subject, or human, which includes alleviation of the symptoms, in whole or in part, of the disorder being treated. The novel methods of treatment of this invention are for disorders known to those skilled in the art. In a particular aspect the amount (dosage) of $H_2S$ that is administered is from about 100 µmol/kg to about 200 µmol/kg.

The chemical compounds used in the methods described herein can be administered to a subject as part of a pharmaceutical composition. Formulations will vary according to the route of administration selected (e.g., solution, emulsion or capsule). A "pharmaceutical composition" comprises a (one or more) chemical compound described herein as the active ingredient and inert ingredient(s), such as pharmaceutically acceptable excipients, that make up the carrier. Standard pharmaceutical formulation techniques can be employed, such as those described in Remington's Pharmaceutical Sciences, Mack Publishing Company, Easton, Pa. Suitable pharmaceutical carriers for parenteral administration include, for example, sterile water, physiological saline, bacteriostatic saline (saline containing about 0.9% mg/ml benzyl alcohol), phosphate-buffered saline, Hank's solution, Ringer's lactate and the like. Formulations can also include small amounts of substances that enhance the effectiveness of the active ingredient (e.g., emulsifying, solubilizing, pH buffering, wetting agents). Methods of encapsulation compositions (such as in a coating of hard gelatin or cyclodextran) are known in the art. For inhalation, the agent can be solubilized and loaded into a suitable dispenser for administration (e.g., an atomizer or nebulizer or pressurized aerosol dispenser).

Any suitable route of administration can be used, for example, oral, dietary, topical, transdermal, rectal, parenteral (e.g., intravenous, intraarterial, intramuscular, subcutaneous injection, intradermal injection), inhalation (e.g., intrabronchial, intranasal or oral inhalation, intranasal drops), ocular, pulmonary, nasal, and the like may be employed. Administration can be local or systemic as indicated. The preferred mode of administration can vary depending on the particular agent chosen. Suitable dosage forms include tablets, troches, dispersions, suspensions, solutions, capsules, creams, ointments, aerosols, and the like.

EXEMPLIFICATION

Example 1

Synthesis of Compounds

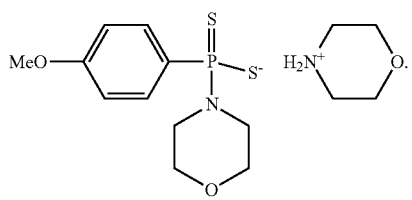

GYY4137

Chemical Synthesis of GYY4137:

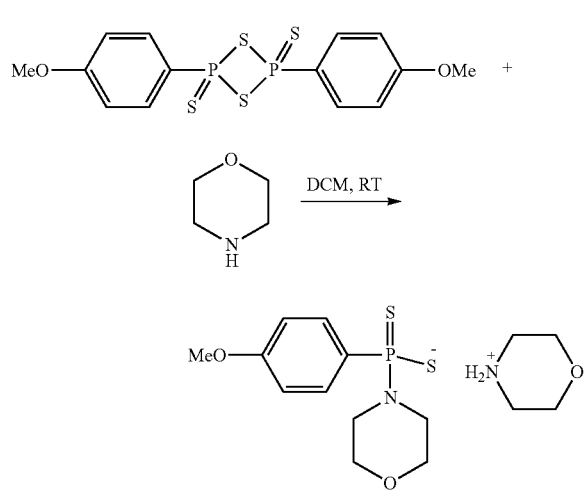

Morpholine (20 mmol) in methyl chloride ($CH_2Cl_2$, 6 mL) was added dropwise (room temperature) to a $CH_2Cl_2$ solution (6 mL) of 2,4-bis(4-methoxyphenyl)-2,4-dithioxo-1,3,2,4-dithiadiphosphetane (4.0 mmol). The reaction mixture was stirred at room temperature for 2 hours. The precipitate was filtered and washed several times with $CH_2Cl_2$. The product was a white solid (67% yield) and was pure as determined by 1H nuclear magnetic resonance.

Characterization of GYY4137

GYY4137 is a white solid with melting point of 159.8-164.0° C. The chemical structure of GYY4137 was indicated by NMR with the following characteristics, $^1$H NMR (300 MHz, acetone-$D_6$, 300K): δ=8.03-8.11 (m, 4H, arom CH), 6.88 to 6.90 (m, 2H, aromatic CH), 3.94 (m, 4H, CH), 3.82 (s, $CH_3$), 3.50-3.53 (m, 4H, CH), 3.36-3.40 (m, 4H, CH), 2.87-2.92 (dd, J=9.7, 5.4 Hz, CH), 2.04-2.09 (m, 4H, CH); $^{13}$C NMR (75 MHz, acetone-$D_6$, 300K): δ=132.7 (arom CH), 132.5 (arom CH), 112.2 (arom CH). 112.0 (arom CH), 66.8 ($CH_2$), 63.6 ($CH_3$), 54.6 ($CH_2$), 54.0 ($CH_2$), 44.9 ($CH_2$), 43.3 ($CH_2$); $^{31}$P NMR (150 MHz, acetone-$D_6$, 300K): δ=89.58 ppm. GYY4137 is soluble in water to the extent of approximately 30 mg/ml (79.8 mM).

Compounds B, C, D, E, H and I were prepared by a method similar to that described above for GYY4137.

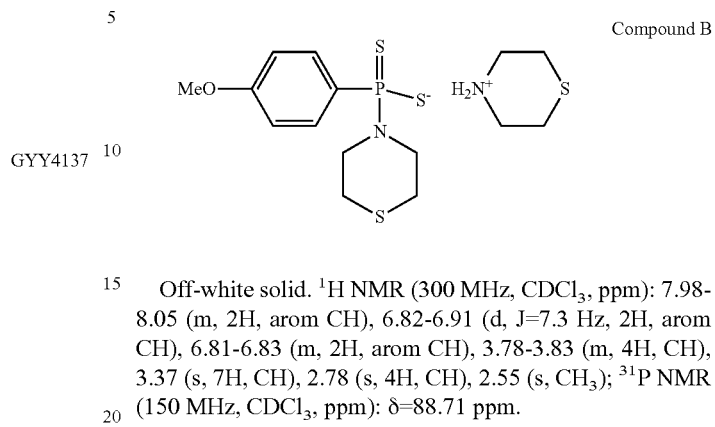

Compound B

Off-white solid. $^1$H NMR (300 MHz, CDCl$_3$, ppm): 7.98-8.05 (m, 2H, arom CH), 6.82-6.91 (d, J=7.3 Hz, 2H, arom CH), 6.81-6.83 (m, 2H, arom CH), 3.78-3.83 (m, 4H, CH), 3.37 (s, 7H, CH), 2.78 (s, 4H, CH), 2.55 (s, $CH_3$); $^{31}$P NMR (150 MHz, CDCl$_3$, ppm): δ=88.71 ppm.

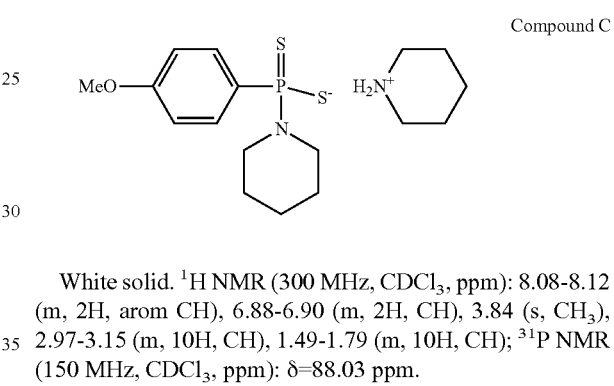

Compound C

White solid. $^1$H NMR (300 MHz, CDCl$_3$, ppm): 8.08-8.12 (m, 2H, arom CH), 6.88-6.90 (m, 2H, CH), 3.84 (s, $CH_3$), 2.97-3.15 (m, 10H, CH), 1.49-1.79 (m, 10H, CH); $^{31}$P NMR (150 MHz, CDCl$_3$, ppm): δ=88.03 ppm.

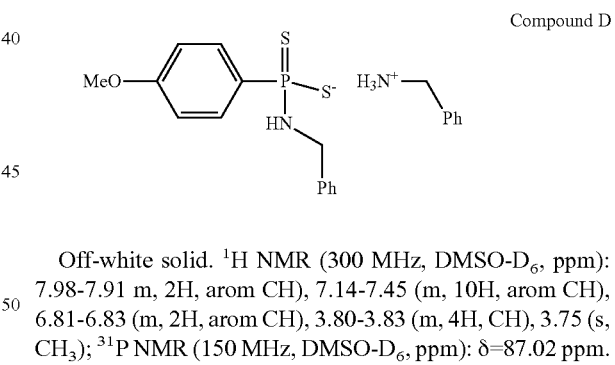

Compound D

Off-white solid. $^1$H NMR (300 MHz, DMSO-$D_6$, ppm): 7.98-7.91 m, 2H, arom CH), 7.14-7.45 (m, 10H, arom CH), 6.81-6.83 (m, 2H, arom CH), 3.80-3.83 (m, 4H, CH), 3.75 (s, $CH_3$); $^{31}$P NMR (150 MHz, DMSO-$D_6$, ppm): δ=87.02 ppm.

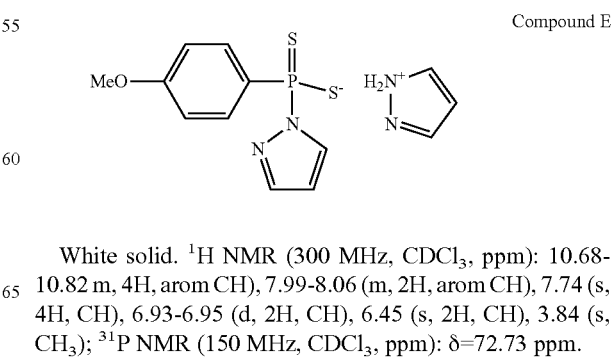

Compound E

White solid. $^1$H NMR (300 MHz, CDCl$_3$, ppm): 10.68-10.82 m, 4H, arom CH), 7.99-8.06 (m, 2H, arom CH), 7.74 (s, 4H, CH), 6.93-6.95 (d, 2H, CH), 6.45 (s, 2H, CH), 3.84 (s, $CH_3$); $^{31}$P NMR (150 MHz, CDCl$_3$, ppm): δ=72.73 ppm.

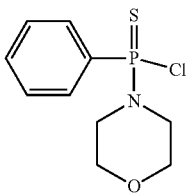

Compound F

Chemical Synthesis of Compound F:

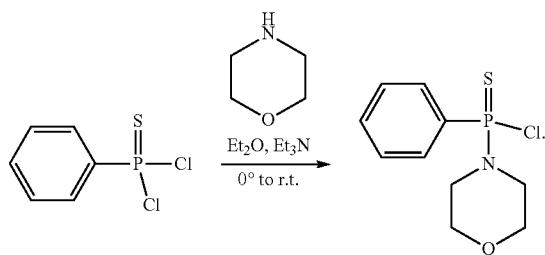

Phenylthiophosphonic dichloride (3 mL, 20 mmol) was dissolved in diethyl ether (Et$_2$O, 20 mL) and triethylamine (Et$_3$N, 20 mmol). Morpholine (1.74 g, 20 mmol) was next added drop-wise to the above mixture at 0° C. in an ice bath. After addition of morpholine, the reaction vessel was removed from the ice bath and the reaction mixture was left to stir overnight at room temperature. The white precipitate EtN$_3$.HCl that formed was filtered and the clear, slightly yellow filtrate concentrated on the vacuum rotary evaporator. Upon standing at ambient temperature, the off-white crystals formed were filtered and washed several times with Et$_2$O. The resulting product was obtained as off-white crystals (1 g, 19% yield). 4-morpholinylphenyl-phosphinothioic chloride was determined to be pure using $^1$H NMR and $^{31}$P NMR without further purification.

$^1$H NMR (300 MHz, D$_2$O, ppm): 7.46-7.82 (m, 5H, arom CH), 3.65-3.67 (m, 4H, CH), 2.67-2.99 (m, 4H, CH); $^{31}$P NMR (150 MHz, D$_2$O, ppm): δ=72.73 ppm.

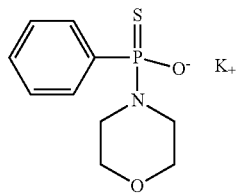

Compound G

Chemical Synthesis of Compound G:

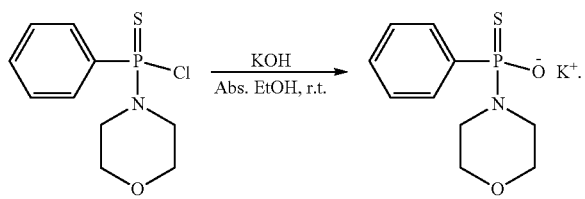

4-morpholinylphenyl-phosphinothioic chloride (0.13 g, 0.5 mmol) was dissolved in absolute ethanol (EtOH, 3.75 mL) and left to stir to give a clear solution. Next, potassium hydroxide (0.056 g, 1 mmol) dissolved in absolute ethanol (EtOH, 0.75 mL) was introduced drop-wise to the above mixture. The resultant mixture was again left to stir overnight. The off-white precipitate that formed was filtered and washed several times with diethyl ether. The end product was obtained as a beige solid (26.7 mg, 19% yield). The final product was determined to be pure using $^1$H NMR and $^{31}$P NMR without further purification.

$^1$H NMR (300 MHz, D2O, ppm): 7.46-7.82 (m, 5H, arom CH), 3.65-3.67 (m, 4H, CH), 2.67-2.99 (m, 4H, CH); $^{31}$P NMR (150 MHz, D$_2$O, ppm): δ=63.65 ppm.

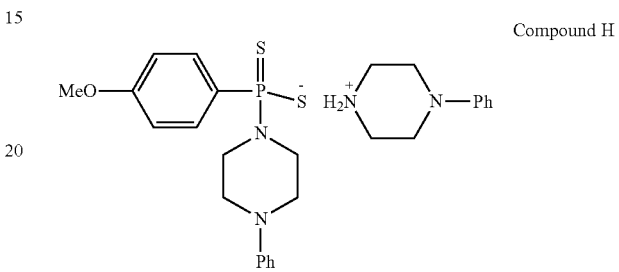

Compound H

White solid. $^1$H NMR (300 MHz, DMSO-D$_6$, ppm): 7.88-7.95 (m, 2H, arom CH), 6.69-7.24 (m, 12H, arom CH), 3.71 (s, 3H, CH$_3$), 3.20-3.30 (m, 8H, CH$_2$), 2.45-2.96 (m, 8H, CH$_2$)

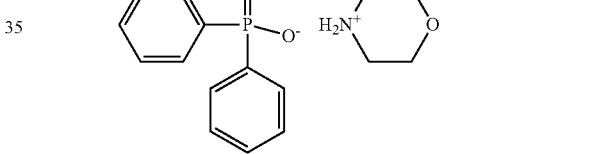

Compound I

White solid. $^1$H NMR (300 MHz, CDCl$_3$, ppm): 7.73-7.80 (m, 4H, arom CH), 7.30-7.34 (m, 6H, arom CH), 3.66-3.69 (t, J=4.8 4H, CH$_2$CH$_2$), 2.83-2.87 (t, J=4.8 4H, CH$_2$CH$_2$)

Example 2

Characterization of Water-Soluble Hydrogen Sulfide-Releasing Molecule (GYY4137)

Materials and Methods

Chemical Synthesis of GYY4137 and Release of H$_2$S In Vitro and In Vivo

Morpholine (20 mmol) in methyl chloride (CH$_2$Cl$_2$, 6 mL) was added dropwise (room temperature) to a CH$_2$Cl$_2$ solution (6 mL) of 2,4-bis(4-methoxyphenyl)-2,4-dithioxo-1,3,2,4-dithiadiphosphetane (4.0 mmol). The reaction mixture was stirred at room temperature for 2 hours. The precipitate was filtered and washed several times with CH$_2$Cl$_2$. The product was a white solid (67% yield) and was pure as determined by $^1$H nuclear magnetic resonance. GYY4137 (melting point, 159.8° C. to 164.0° C.) is soluble in water up to 30 mg/mL (pH 7.4) (FIG. 1). The nuclear magnetic resonance characteristics of GYY4137 are as follows: $^1$H nuclear magnetic resonance (300 MHz, acetone-D6, 300K): δ=8.03 to 8.11 (m, 2H, aromatic CH), δ=6.88 to 6.90 (m, 2H, aromatic CH), 3.94 (m, 4H, CH), 3.82 (s, CH$_3$), 3.50 to 3.53 (m, 4H, CH), 3.36 to 3.40 (m, 4H, CH), 2.87 to 2.92 (dd, J=9.7, 5.4 Hz, CH), 2.04 to 2.09 (m, 4H, CH); $^{13}$C nuclear magnetic resonance (75 MHz, acetone-D6, 300K): δ=132.7 (aromatic CH), 132.5 (aromatic CH), 112.2 (aromatic CH), 112.0 (aromatic CH), 66.8 (CH$_2$), 63.6 (CH$_3$), 54.6 (CH$_2$), 54.0 (CH$_2$), 44.9 (CH$_2$), 43.3 (CH$_2$). The infrared (film) values were 3019 cm$^{-1}$, 1215 cm$^{-1}$, and 756 cm$^{-1}$.

H$_2$S release from GYY4137 in vitro was assessed with the use of 5,5'-dithiobis-(2-nitrobenzoic acid) (DTNB) and by amperometry. For DTNB experiments, phosphate buffer (100 mmol/L, pH 3.0, 7.4, or 8.5) was incubated (4° C. to 37° C.) with GYY4137 or NaHS (1 mmol/L; 100 μL), and, at appropriate times, aliquots (20 μL) were removed and added to 96-well microplates containing DTNB (1 mmol/L; 50 μL) and HEPES buffer (1 mol/L, 50 μL, pH 8.0), and absorbance was measured at 1412 nm. The concentration of H2S formed from GYY4137 was calculated from a standard curve of NaHS (1 to 500 μmol/L).

For amperometry experiments, GYY4137 (1 mmol/L) or NaHS (100 μmol/L) was added to an incubation chamber (World Precision Instruments; WPI) containing phosphate buffer (100 mmol/L; pH 7.4, 400 μL). H$_2$S formation was detected with the use of a 2-mm H$_2$S-selective microelectrode (ISO—H$_2$S-2; WPI) attached to an Apollo 1100 Free Radical Analyser (WPI) and shown as picoamps current generated, as described previously (Whiteman, M., et al., *Nitric Oxide*, 14:A40. Abstract (2006)).

For in vivo experiments, male Sprague-Dawley (weight, 230 to 260 g) rats were anesthetized (2 mL/kg IP) with a mixture of ketamine (24% vol/vol) and medetomidine (16% vol/vol). A femoral artery and vein were cannulated for blood withdrawal and injection of GYY4137 (133 μmol/kg IV or IP) or NaHS (20 μmol/kg IV), respectively. Blood (0.5 mL) was withdrawn at timed intervals, anticoagulated with heparin (50 U/mL), and centrifuged (2000 g, 20 minutes). Plasma H$_2$S concentration was assayed spectrophotometrically after H$_2$S was trapped with zinc acetate, as described previously (Li, L., et al., *FASEB J.*, 19:1196-1198 (2005)). The zinc acetate assay measures free H$_2$S plus related species including HS$^-$ (hydrosulfide anion) and S$_2^-$ (sulfide). Accordingly, results for plasma H$_2$S reported herein indicate the sum total of these species. All experiments on intact animals were undertaken with the approval of the local National University of Singapore Institutional Animal Care and Use Committee.

Effect of GYY4137 on Smooth Muscle Cell Viability

Normal rat aortic vascular smooth muscle cells (A10) were obtained from the American Type Culture Collection (ATCC, Manassas, Va.). Cells were cultured in Dulbecco's modified Eagle's medium containing fetal calf serum and antibiotics, and cell viability, cell cycle distribution, and p53 expression were determined as described previously (Baskar, R., et al., *FASEB J.*, 21:247-255 (2007)). In separate experiments, cultured cells were exposed to sodium nitroprusside, forskolin, or GYY4137 (all 100 μmol/L) for 45 minutes in the presence of isobutyl methylxanthine (300 μmol/L), and cAMP and cGMP were measured by enzyme-linked immunosorbent assay (R&D Systems, Minneapolis, Minn.).

Effect of GYY4137 on Rat Aorta

Rat (male, Sprague-Dawley; weight, 250 to 300 g) aortic rings were prepared as described previously (Ali, M. Y., et al., *Br. J. Pharmacol.*, 149:609-620 (2006). 13 Dose-response curves to NaHS were performed cumulatively while each aortic ring was exposed to a single concentration of GYY4137. In some experiments, responses to NaHS (300 μmol/L) or GYY4137 (200 μmol/L) were evaluated in aortic rings preincubated (30 minutes) with the K$_{ATP}$ channel blockers glibenclamide (Ceron, P. I. B., et al., *J. Pharmacol. Exp. Ther.* 298:686-694 (2001)) (10 μmol/L) or PNU37883A (Wellman, G. C., et al., *Br. J. Pharmacol.*, 128:909-916) (1999) (10 μmol/L), the NO synthase inhibitor N$^G$-nitro-L-arginine methyl ester (L-NAME) (50 μmol/L), the cyclooxygenase inhibitor indomethacin (Berkenboom, G., et al., *Eur. J. Pharmacol.*, 193:81-86 (1999)) (2.8 μmol/L), the soluble guanylate cyclase inhibitor ODQ (Feelisch, M., et. al., *Mol. Pharmacol.*, 56:243-253 (1999)) (3 μmol/L), the adenylate cyclase inhibitor SQ23356 (Janciauskiene, S. M., et al., *J. Biol. Chem.*, 282:8573-8582 (2007)) (50 μmol/L), or a mixture of apamin (100 nmol/L) and charybdotoxin (Pérez-Vizcaíno, F., et al., *Br. J. Pharmacol.*, 128:1419-1426) (1999) (50 nmol/L) to block the effect of endothelium-derived hyperpolarizing factor. The effect of both NaHS and GYY4137 was also evaluated in endothelium-denuded rings, as was the time course of effect as determined by the ability to reduce the contraction to a standard concentration of phenylephrine (200 nmol/L).

Effect of GYY4137 on Perfused Kidney and Heart

For experiments using perfused kidney or heart, Sprague-Dawley rats (male; weight, 230 to 270 g) were anesthetized as described above. The renal artery was cannulated and the kidney perfused as described previously (Moore, P. K., et al., *J. Pharm. Pharmacol.*, 41:426-429 (1989)). The heart was also removed and perfused (Langendorff preparation) as described elsewhere (Xiao, X. H., et al., *Circ. Res.*, 85:723-730 (1999)). In kidneys, dose-response curves (volumes <10 μL) were obtained for bolus-injected noradrenaline, angiotensin II, or U46619. GYY4137 (100 to 500 mmol/L) was added to the perfusing Krebs' solution, and the responses to each agonist was repeated. After 60 minutes, kidneys were reperfused with normal Krebs' solution to assess the reversibility of the GYY4137 effect. Hearts were perfused with Krebs' solution containing either GYY4137 (100 μmol/L) or NaHS (100 μmol/L), and left ventricular diastolic pressure was monitored. In separate experiments, the effect of GYY4137 (10 to 100 μmol/L) or NaHS (100 μmol/L) on heart rate (bpm) was determined.

Antihypertensive Effect of GYY4137

The methods used to assess the effect of GYY4137 on blood pressure in the anesthetized rat have been described previously (Mok, Y. Y. P., et al., *Br. J. Pharmacol.*, 143:881-889 (2004)) and (Ali, M. Y., et al., *Br. J. Pharmacol.*, 149: 609-620 (2006)). The effect of GYY4137 (26.6 to 133 μmol/kg IV) and NaHS (2.5 to 20 μmol/kg IV) was determined. The effect of pretreating animals (5 minutes before GYY4137) with PNU37883A (26.2 μmol/kg IP) or its vehicle (dimethyl sulfoxide, 0.15 mL/kg IP) on the vasodepressor effect of GYY4137 was assessed, as was the effect of GYY4137 (133 μmol/kg) and NaHS (2.5 μmol/kg) administered intravenously 30 minutes before a hypertensive dose of L-NAME (185 μmol/kg IV). In other experiments, the effect of GYY4137 (133 μmol/kg IV) on the response to sodium nitroprusside (10 nmol/kg) was also evaluated.

The effect of GYY4137 on blood pressure of conscious, male spontaneously hypertensive rats (SHR) and normotensive Wistar-Kyoto (WKY) rats (age, 7 weeks; weight, 221 to 257 g) was studied. Systolic blood pressure was monitored with the use of a tail cuff connected to a PowerLab (AD Instruments Inc, Australia) attached to a computer running Chart (version 5.1). Blood pressure was determined (9:30 to 10:30 AM) before administration of GYY4137 (133 μmol/kg IP) or saline (1.0 mL/kg IP) and again for up to 28 days after drug injection was started. Drug administration was halted on day 14.

Statistical Analysis

Data are mean±SEM. Statistical analysis was by 1-way ANOVA or repeated-measures ANOVA, followed by the post hoc Tukey test or by the Student t test, as appropriate.

Results

Figure 2B:
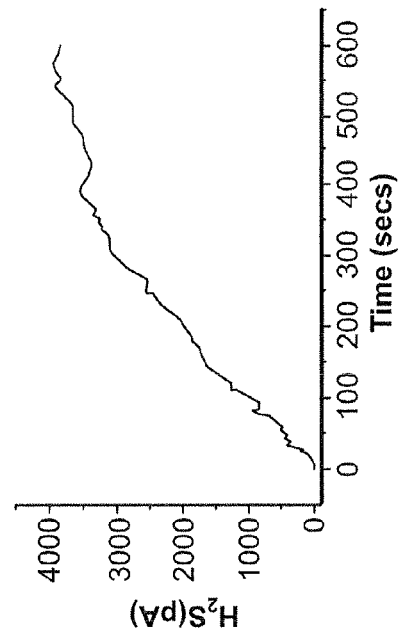
FIGS. 2A-2D are graphs showing release of $H_2S$ from NaHS (100 μmol/L) (2A) and GYY4137 (1 mmol/L) (2B) in phosphate buffer (pH 7.4, except 2C) in vitro as determined by amperometry (measured as picoamps) or spectrophotometrically (2C, 2D) with the use of DTNB. Effect of pH and time (2C) and temperature (2D) on the release of $H_2S$ from GYY4137 is shown. In 2C, symbols for pH 7.4 and pH 8.5 overlap. Where no error bars are indicated, error lies within dimensions of symbol. Results show representative tracings (A, B) of at least 4 similar measurements and for 2C and 2D are mean±SEM; n=6.
Figure 2D:
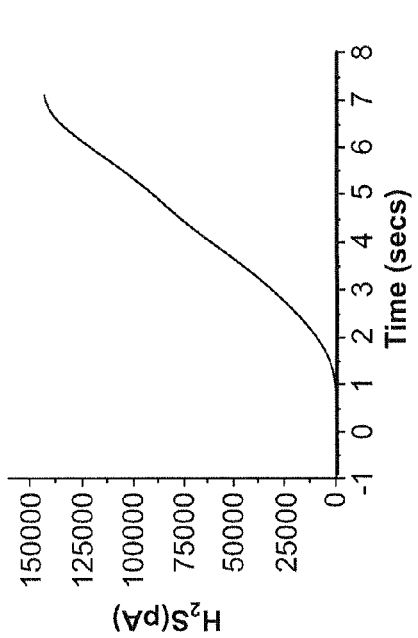
Figure 2A:
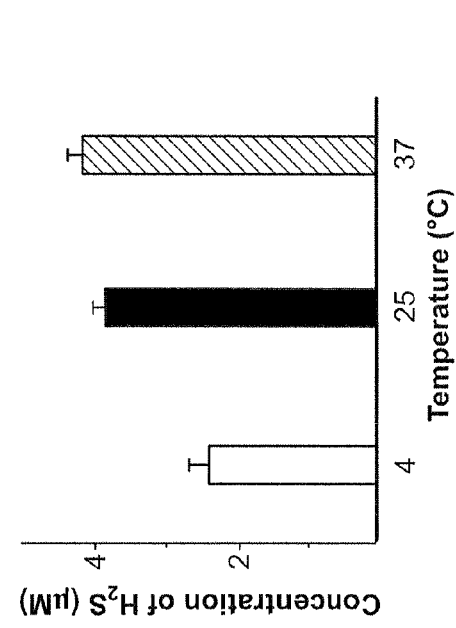

Release of $H_2S$ From GYY4137 In Vitro and In Vivo $H_2S$ release from NaHS was instantaneous in the DTNB assay. Indeed, $H_2S$ generation from NaHS was so rapid that a time course was not attempted. Real-time assessment of $H_2S$ release from NaHS by amperometry showed peak signal generation (for $H_2S$) within 5 to 8 seconds (FIG. 2A).

Figure 2C:
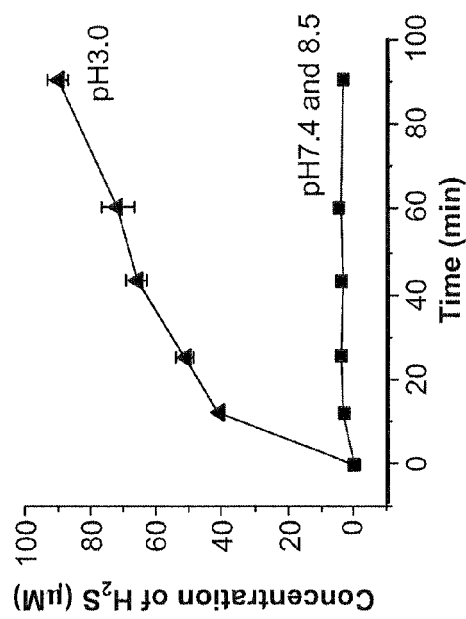

In contrast, release of $H_2S$ from GYY4137 (pH 6.5) was slower, peaking at ≈6 to 10 minutes with the use of the $H_2S$ microelectrode (FIG. 2B) or the DTNB (FIG. 2C) assay. On incubation, GYY4137 releases low amounts of $H_2S$ over a sustained period in aqueous solution (pH 7.4, 37° C.). The rate of $H_2S$ release from GYY4137 (1 mmol/L, i.e., 100 nmol incubated) was 4.17±0.5 nmol/25 min (n=6, DTNB assay). When incubated in aqueous buffer (pH 7.4, 37° C.), $H_2S$ release climbed for 15 minutes and then plateaued at 75 minutes (FIG. 2C). Release of $H_2S$ from GYY4137 was pH dependent (FIG. 2C) and temperature dependent (FIG. 2D), with less release at 4° C. and greater release at pH 3.0.

After administration (intravenous or intraperitoneal) of GYY4137 to anesthetized rats, plasma $H_2S$ (defined as $H_2S$, $HS^-$, and $S_2^-$) concentration was increased at 30 minutes and remained elevated over the 180-minute time course of the experiment (FIG. 3A). In contrast, NaHS administered to anesthetized rats did not elevate plasma $H_2S$ levels at these time points (FIG. 3B).

Effect of GYY4137 on Vascular Smooth Muscle Cell Viability

Figure 4A:
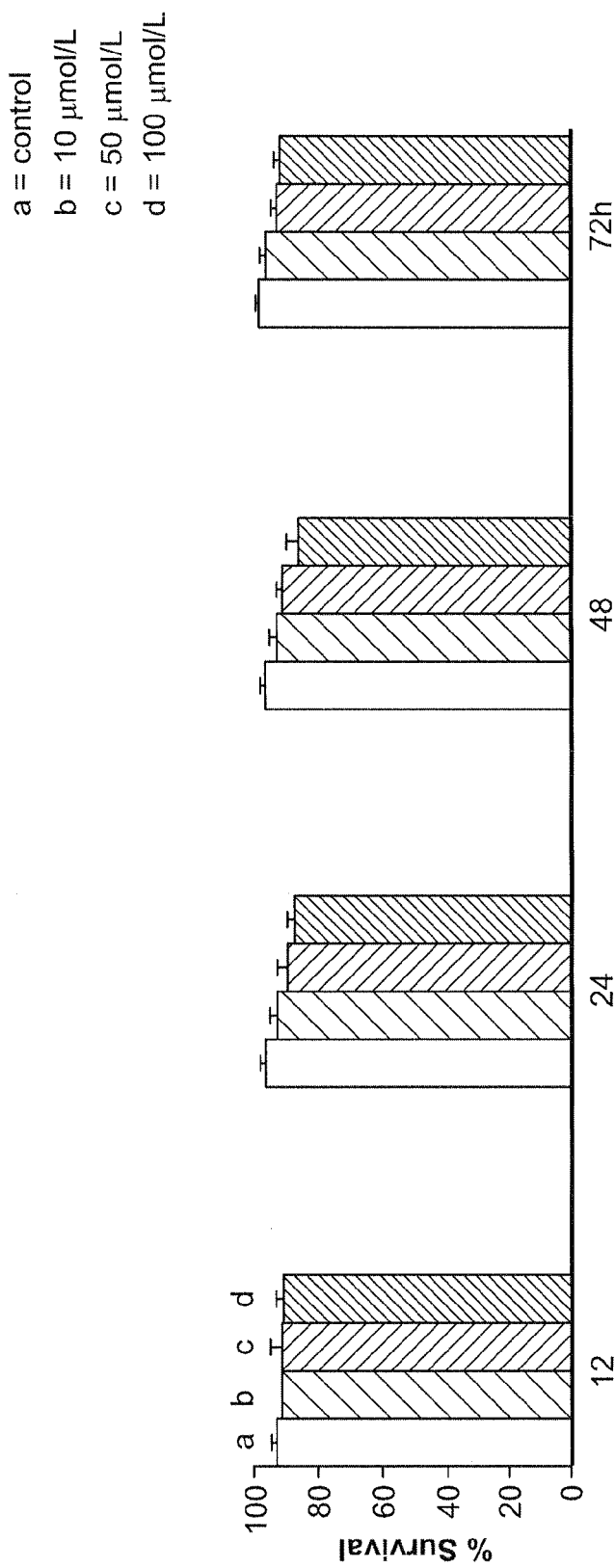

Treatment of rat vascular smooth muscle cells with GYY4137 (up to 100 μmol/L) for up to 72 hours did not cause detectable cytotoxicity (FIG. 4A), change cell cycle distribution (FIG. 4B), or induce p53 expression in these cells (FIG. 4C).

Isolated Rat Aortic Ring

Figure 5A:
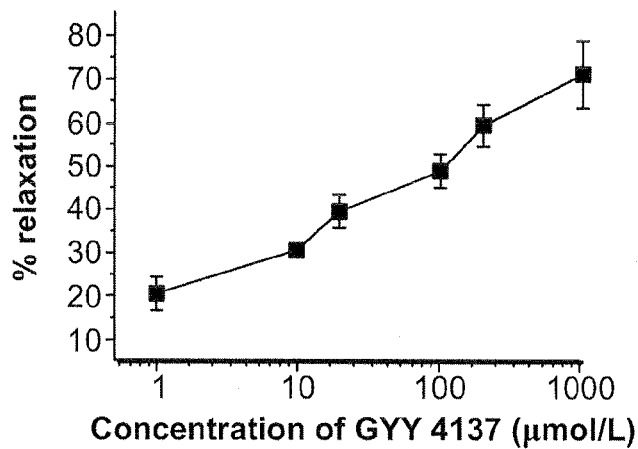
FIGS. 5A-5E are graphs of dose-response curves (5A, 5B) and time course of effect (5C) of GYY4137 and NaHS on phenylephrine-precontracted rat aorta. For the time course experiments (5C), separate rings were exposed to phenylephrine (200 nmol/L) and then to approximate $EC_{70}$s of either GYY4137 (200 μmol/L) or NaHS (300 μmol/L) followed at timed intervals thereafter by phenylephrine (200 nmol/L). Results are expressed as percent contraction where response to phenylephrine before drug addition is shown as 100%. The effects of glibenclamide (GLIB; 10 μmol/L), L-NAME (50 μmol/L), ODQ (3 μmol/L), indomethacin (INDO, 2.8 μmol/L), SQ233356 (50 μmol/L) PNU37883A (10 μmol/L), a combination of apamin (100 nmol/L) and charybdotoxin (50 nmol/L) (5A and 5C), and removal of the endothelial layer (−EC) on the response to GYY4137 (200 μmol/L) and NaHS (300 μmol/L) are shown in 5D and 5E. Results are mean±SEM; n=8 to 21. *P<0.05 vs control.
Figure 5B:
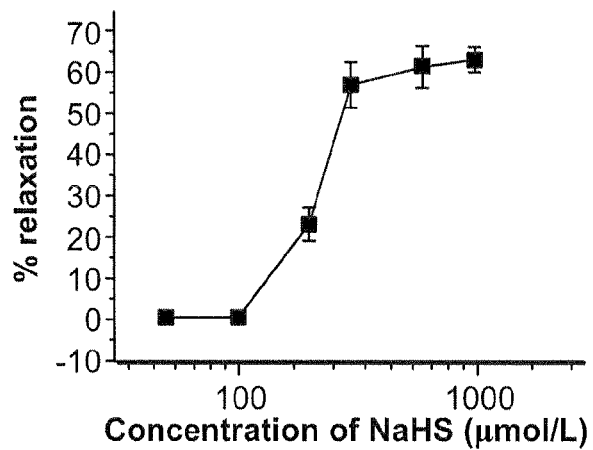
Figure 5C:
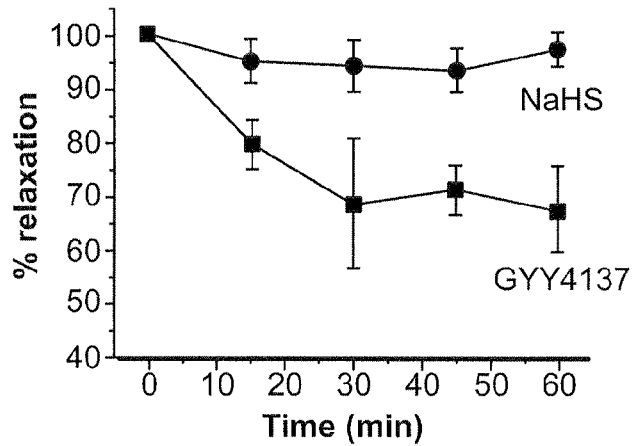

NaHS caused rapid, transient, and reversible (≈20 to 30 seconds) relaxation of aortic rings, whereas the effect of GYY4137 was slower in onset (≈10 minutes) and sustained (≈40 minutes). GYY4137 ($EC_{50}$, 115.7±6.7 μmol/L; $E_{max}$, 74.8±4.7%; n=8) was more potent than NaHS ($EC_{50}$, 274.1±22.2 μmol/L; $E_{max}$, 63.4±3.3%; n=11) (FIGS. 5A, 5B). The time course of effect of GYY4137 was also studied. The response to a standard concentration of phenylephrine was decreased 15 minutes after GYY4137 addition and remained reduced for at least an additional 45 minutes. In contrast, NaHS did not reduce the effect of added phenylephrine (FIG. 5C).

Figures 5D, 5E:
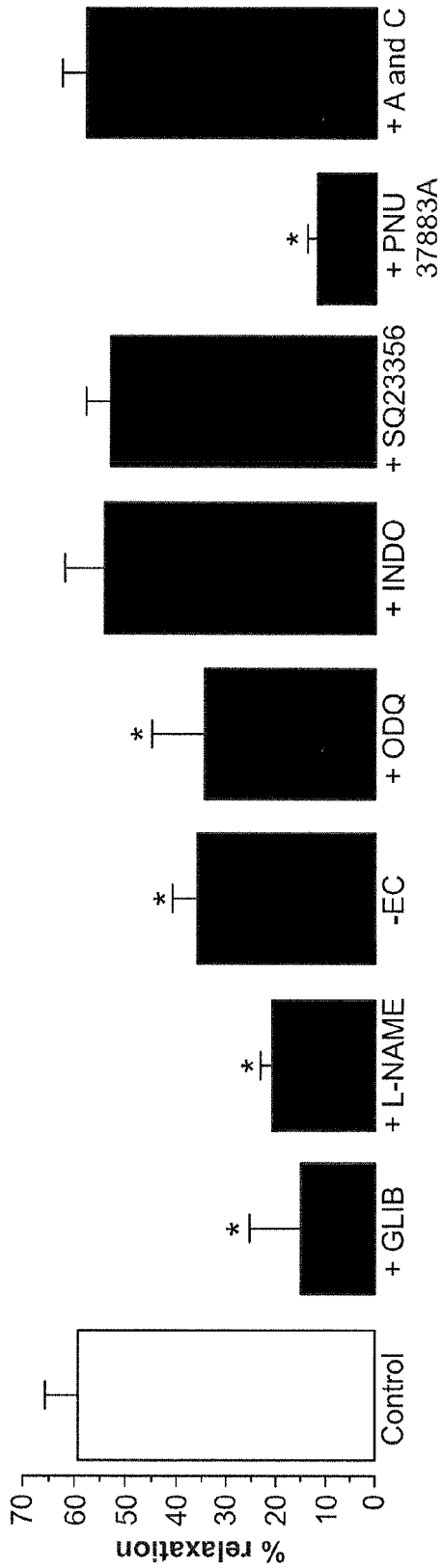

The effect of antagonists on the vasorelaxant response to GYY4137 and NaHS was also examined. The effect of GYY4137 and NaHS was reduced by $K_{ATP}$ channel blockers (glibenclamide or PNU37883A) but not by indomethacin, SQ23356, or a mixture of apamin and charybdotoxin. Removal of the endothelium or exposure of intact rings to L-NAME or ODQ reduced the vasorelaxant effect of both GYY4137 and NaHS (FIGS. 5D and 5E).

Incubation of cultured vascular smooth muscle cells with sodium nitroprusside or forskolin increased cGMP (24.5±1.3 versus 9.7±0.9 nmol/L; n=6; P=0.0001) and cAMP (79.6±1.6 vs 11.3±1.4 nmol/L; n=6; P=0.0001) concentrations, respectively. In contrast, GYY4137 (100 μmol/L) did not directly affect the concentration of either cGMP (10.7±1.9 nmol/L; n=6; P=0.64) or cAMP (12.74±1.4 nmol/L; n=6; P=0.50) under identical experimental conditions.

Perfused Rat Kidney and Heart

Figures 6A, 6B:
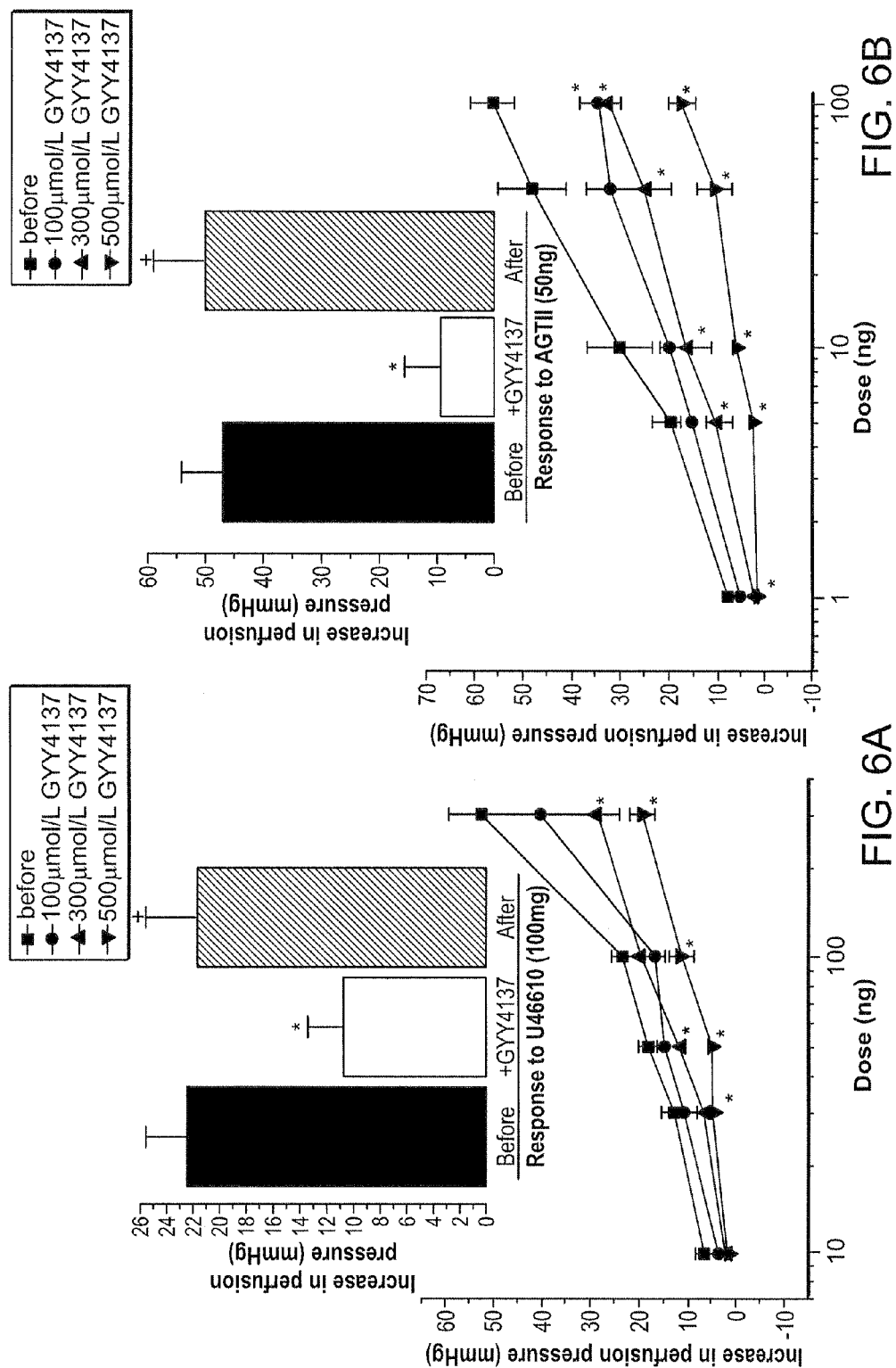
FIGS. 6A-6D are graphs of the effect of GYY4137 (100 to 500 μmol/L) on vasoconstrictor responses of isolated perfused rat kidney to U46619 (6A), angiotensin II (AGT II) (6B), and noradrenaline (NA) (6C). Insets to each figure show vasoconstrictor response to a single dose of each agonist before, during, and after exposure to GYY4137 (500 μmol/L) to show reversibility of effect. 6D, Effect of GYY4137 (100 μmol/L) on the response to angiotensin II in the absence and presence of PNU37883A (10 μmol/L). Results show increase in perfusion pressure (mm Hg) and are mean±SEM; n=6 to 8. *P<0.05 vs control.
Figures 6C, 6D:
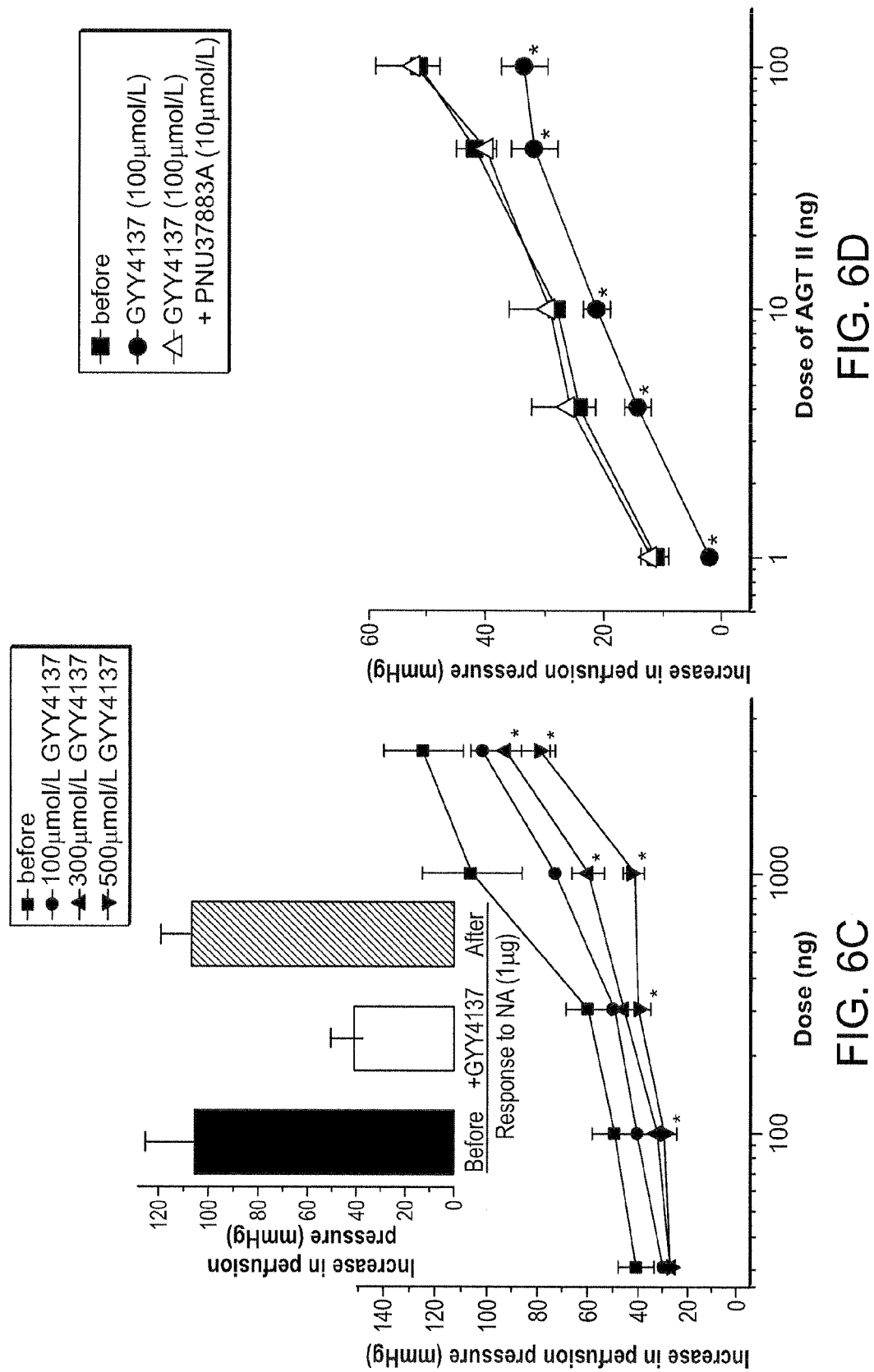

The effect of bolus injection of NaHS in the rat kidney was complex, with low doses causing transient falls in perfusion pressure (e.g., 10 nmol; 10.2±2.8 mm Hg; n=10), whereas higher doses (e.g., 5 μmol) caused a biphasic response made up of a fall (11.6±4.5 mm Hg; n=8) followed by a rise (22.7±6.7 mm Hg; n=8) in perfusion pressure. In contrast, bolus injection of GYY4137 (0.4 to 4.0 μmol) did not consistently affect renal perfusion pressure. The effect of GYY4137 was therefore assessed indirectly by reduction of the vasoconstrictor response to standard agonists. Bolus injection of U46619, angiotensin II, or noradrenaline caused dose-related vasoconstriction. GYY4137 (100 to 500 μmol/L) in the perfusing Krebs' solution caused concentration-related vasorelaxation, the effect of which was lost when the drug was removed from the perfusing solution (FIG. 6A through 6C) or when angiotensin II was tested in the presence of PNU37883A (FIG. 6D). Exposure of isolated hearts to NaHS (100 μmol/L) reduced cardiac contractility (left ventricular diastolic pressure) by 42.0±7.8% (n=7) and heart rate by 53.2±6.6% (n=9) at 30 minutes. GYY4137 by itself did not affect cardiac contractility or heart rate (FIGS. 7A-7B).

Effect of GYY4137 on Blood Pressure of Normotensive and SHR

Figure 8A:
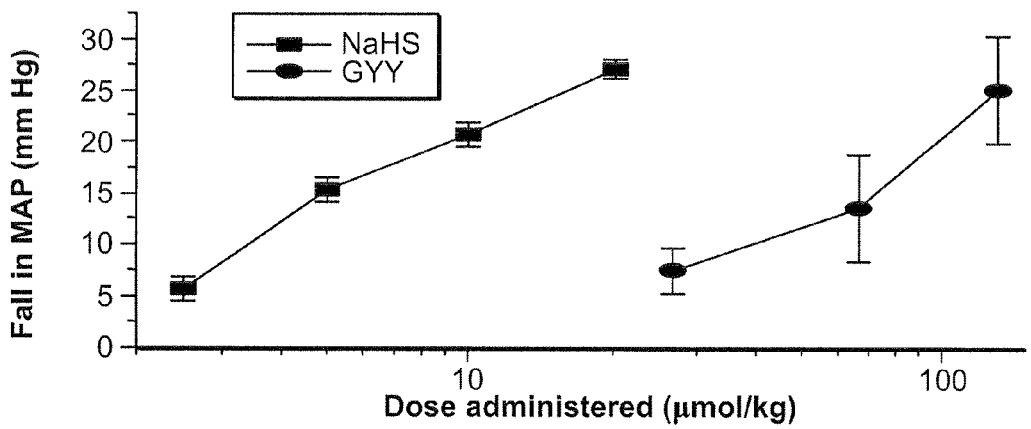
FIGS. 8A-8C show 8A, Effect of GYY4137 (GYY) (26.6 to 133 μmol/kg IV measured at 120 minutes) and NaHS (2.5 to 20 μmol/kg IV) on blood pressure in the anesthetized rat. MAP indicates mean arterial pressure. Results show mean±SEM; n=6. 8B, Effect of GYY4137 (133 μmol/kg) or NaHS (2.5 μmol/kg) on the hypertensive response to L-NAME (185 μmol/kg) injected at T=0 (indicated by vertical, dashed line). Results show mean±SEM; n±6. *P<0.05 vs saline+L-NAME. 8C, Effect of chronic (14 consecutive days) administration of GYY4137 (133 μmol/kg IP) or saline on systolic blood pressure of SHR or normotensive WKY rats. Drug administration commenced on day 0 (Start) and ceased on day 14 (Stop), after which systolic blood pressure was monitored for an additional 14 days. Results show mean±SEM; n=8. *P<0.05 vs pretreatment values.

NaHS (2.5 to 20 μmol/kg) caused immediate, transient (10 to 30 seconds), and dose-related falls in blood pressure in anesthetized rats (FIG. 8A). GYY4137 (26.6 to 133 μmol/kg) caused a slowly developing fall in blood pressure that was apparent at 30 minutes and continued declining to 120 minutes after injection. GYY4137 modestly increased heart rate in these animals (e.g., at 133 μmol/kg, 250.1±12.0 bpm, 60 minutes versus 213.5±3.2 bpm before drug injection; n=6; P=0.01). Pretreatment with PNU37883A did not significantly affect blood pressure (e.g., at 15 minutes after PNU37883A, 117.2±3.7 mm Hg versus 105.6±3.5 mm Hg; n=5; P=0.053, before injection). However, PNU37883A injection blocked the vasodepressor effect of GYY4137 (e.g., at 120 minutes, 120.6±4.1 mm Hg versus 117.2±3.7 mm Hg; n=5; P=0.56). In separate experiments, GYY4137 (133 μmol/kg) did not affect the vasodepressor response to sodium nitroprusside (33.1±7.02 mm Hg fall before versus 29.3±5.6 mm Hg fall 30 minutes after injection; n=5; P=0.68).

Figure 8B:
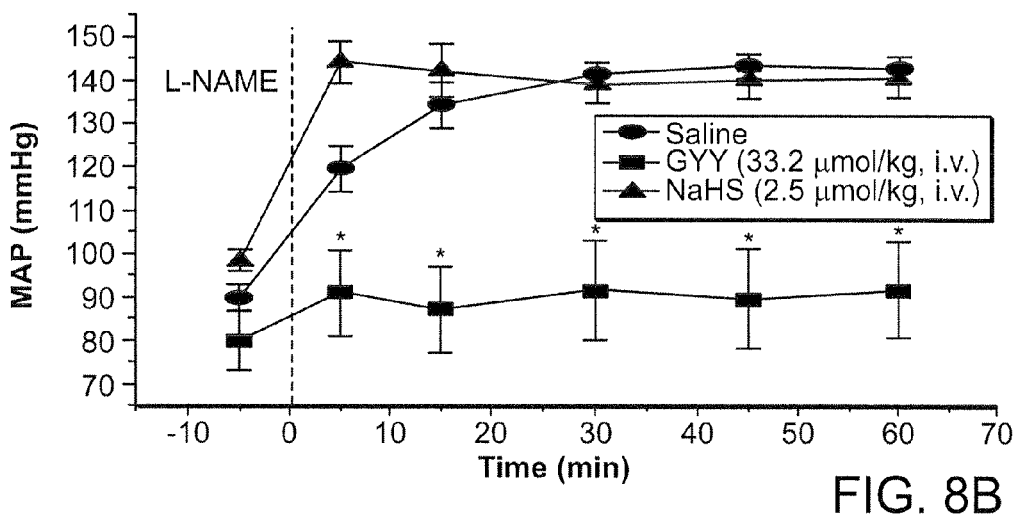
Figure 8C:
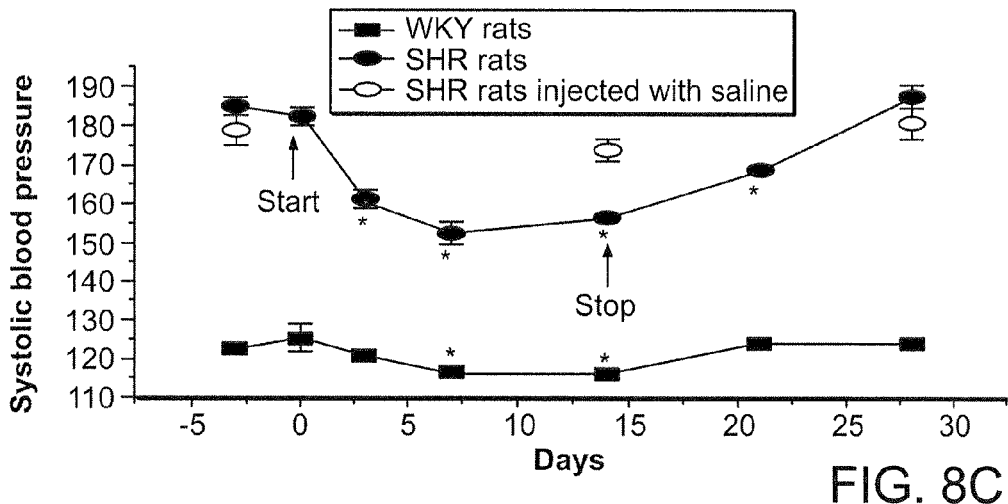

Two approaches were taken to examine the antihypertensive effect of GYY4137. First, acute injection of GYY4137 (133 μmol/kg IV) but not NaHS (2.5 μmol/kg IV) or saline 30 minutes before L-NAME administration reduced the L-NAME-mediated hypertension (FIG. 8B). Second, chronic treatment of conscious animals with GYY4137 reduced systolic blood pressure (FIG. 8C). The fall in blood pressure was apparent after 2 days and was still present after 14 days of treatment and was considerably greater in SHR than in normotensive animals. Treatment of rats with saline did not affect blood pressure. On cessation of drug therapy, blood pressure of WKY rats returned to preinjection values within 7 days, at which point blood pressure of SHR was still significantly reduced. Blood pressure of all animals returned to normal within 14 days of cessation of treatment. Daily treatment with GYY4137 did not affect weight gain (e.g., at 14 days, WKY, 64.9±14.5 g and SHR, 55.2±13.2 g versus saline-injected WKY, 60.1±10.7 g and SHR, 59.8±8.9 g; n=8; P=0.79 and P=0.78, respectively) and, although not evaluated objectively, did not cause discernible signs of toxicity such as deterioration of fur condition, sedation, altered locomotor activity, or other gross behavioral changes.

Discussion

Described herein is the chemical synthesis and characterization of the cardiovascular effects of GYY4137, a novel molecule that, unlike NaHS, decomposes slowly to generate small amounts of H2S in vitro and in vivo. GYY4137 was originally described ≈50 years ago as an accelarant for the vulcanization of rubber, but there have been no previous reports of its biological activity.

In aqueous solution at physiological temperature and pH, $H_2S$ release from GYY4137 is a slow process with ≈4% to 5% $H_2S$ generated from a starting concentration of 1 mmol/L within 25 minutes. In contrast, $H_2S$ generation from NaHS is more or less instantaneous and certainly far too rapid to establish a time course of release even at room temperature. Release of $H_2S$ from GYY4137 in vitro is both temperature and pH dependent, with limited generation on ice (4° C.) and enhanced release under acidic conditions (pH 3.0). The finding that H promotes $H_2S$ release from the parent molecule implies an electrophilic attack directed against the thione ring structure of GYY4137 structure.

A sustained increase in plasma $H_2S$ (defined as $H_2S$, $HS^-$, and $S_2^-$) concentration was observed for up to 180 minutes after intravenous or intraperitoneal administration of GYY4137 in anesthetized rats. As shown previously in vitro, these data therefore suggest that GYY4137 (unlike NaHS) releases $H_2S$ slowly when injected in the anesthetized rat.

GYY4137 did not cause significant cytotoxic effect or alter the cell cycle profile or p53 expression of cultured rat vascular smooth muscle cells. We (Baskar, R., et al., *FASEB J.*, 21:247-255 (2007)) and others (Yang, G., et al., *FASEB J.*, 18:1782-1784 (2004)) have previously reported that NaHS (at similar concentrations and time course) promoted the apoptotic cell death of cultured fibroblasts and smooth muscle cells. That GYY4137 did not cause apoptosis in the present experiments may be explained by differences in the relative rates of $H_2S$ release from the 2 drugs. Thus, large amounts of $H_2S$ released over a short time frame (seconds) by NaHS may trigger signaling pathways leading to cell death, whereas this does not occur with the slower but sustained release of lower amounts of $H_2S$ from GYY4137. The ability of $H_2S$ to regulate cell viability in vivo may therefore be concentration and time dependent. At low concentrations, as may occur in physiological conditions (mimicked by GYY4137), cells remain unscathed by $H_2S$, but, at high concentrations, as may occur in pathological states (and mimicked by NaHS), a cytotoxic/proapoptotic effect becomes evident. These experiments highlight the usefulness of a slow-releasing $H_2S$ donor in advancing our understanding of the biological significance of this gas.

The effect of GYY4137 on cardiovascular function was also studied with a range of in vitro and in vivo pharmacological preparations. GYY4137 caused a slow relaxation of precontracted rat aortic rings, whereas the effect of NaHS was more rapid in onset and transient. GYY4137 was more potent presumably because aortic rings were in contact with the drug for longer times (compared with NaHS) and hence were exposed to accumulated $H_2S$ over a longer time period. The effect of GYY4137 and NaHS was inhibited by glibenclamide and PNU37883A and reduced by endothelium removal and pretreatment with L-NAME and ODQ, which block the formation/vascular response to NO, respectively. In contrast, inhibition of cyclooxygenase enzyme activity (with indomethacin) or blocking the effect of vasodilator prostanoids such as prostaglandin $I_2$ and prostaglandin $E_2$ on adenylate cyclase (with SQ23356) did not affect the response to either GYY4137 or NaHS, suggesting that augmented endothelial prostanoid generation plays no part in the response to either $H_2S$ donor. Similarly, direct measurement of cAMP/cGMP in cultured vascular smooth muscle revealed no significant effect of GYY4137, again indicating no direct action on guanylate or adenylate cyclase enzyme activity. Finally, a combination of apamin and charybdotoxin did not alter the response to either drug, again suggesting the lack of involvement of endothelium-derived hyperpolarizing factor. Taken together, these data support the hypothesis that both NaHS and GYY4137 open vascular smooth muscle cell $K_{ATP}$ channels and that at least part of the effect of both agents in this tissue involves the release of endogenous NO from endothelial cells. Essentially similar conclusions have been reached by other authors studying the effect of NaHS on rat aortic rings. (Zhao, W., et al., *EMBO J.*, 20:6008-6016 (2001)). In contrast, several $H_2S$-releasing organic persulfides present in garlic have been shown to relax rat aortic rings by an endothelium-independent mechanism (Benavides, G., et al., *Proc. Natl. Acad. Sci. USA*, 104:17977-17982 (2007)). Other researchers have reported an endothelium-dependent component of the vasodilator response to garlic (Ashraf, M. Z., et al., *J. Ethnopharmacol.*, 90:5-9 (2004)). The precise role of NO in the response of blood vessels to H2S is therefore unclear. The $O_2$ concentration at which experiments are conducted may determine the endothelium/NO dependence of the effect of $H_2S$ because a high (i.e., 95%) level of oxygen reportedly promotes the involvement of NO in this response (Benavides, G., et al., *Proc. Natl. Acad. Sci. USA*, 104:17977-17982 (2007)).

GYY4137 was a vasodilator in the perfused rat kidney. Low doses of NaHS produced short-lived falls in renal perfusion pressure, as described previously in the rat mesenteric vasculature (Cheng, Y., et al., *Am. J. Physiol.*, 287:H2316-H2323 (2004)). However, higher doses caused a biphasic relaxation/constriction response, the mechanism of which warrants further study. $H_2S$ can contract isolated blood vessels either by quenching released NO (Ali, M. Y., et al., *Br. J. Pharmacol.*, 149:609-620 (2006)), by inhibiting endothelial NO synthase (Geng, B., et al., *Am. J. Physiol.*, 293:1608-1618 (2007)), or by oxidation of $H_2S$ to a vasoconstrictor molecule in conditions of high oxygen tension (Koenitzer, J. R., et al., *Am. J. Physiol.*, 292:1953-1960 (2007)). Bolus injection of GYY4137 did not affect renal perfusion pressure, presumably because the drug is washed out of the tissue before sufficient breakdown to $H_2S$ occurs. However, addition of GYY4137 to the perfusing Krebs' solution dilated the renal vasculature, as evidenced by reduced response to vasoconstrictor drugs. This effect of GYY4137 was readily reversible and antagonized by PNU37883A, which indicates that, as in aortic rings, GYY4137 is a vasodilator by opening vascular smooth muscle $K_{ATP}$ channels in the kidney. These observations demonstrate that, in vitro, GYY4137 relaxes not only large-capacitance vessels but also small-resistance arterioles, implying a potential effect of this compound on blood pressure and tissue perfusion in vivo. In contrast to $H_2S$ (released rapidly from NaHS), it is likely that the vascular effect of $H_2S$ (released slowly from GYY4137) more closely parallels the biological effects of endogenous $H_2S$. In the isolated heart, exposure to NaHS (but not GYY4137) caused a negative inotropic and chronotropic effect, as reported previously (Geng, B., et al., *Biochem. Biophys. Res. Commun.*, 313:362-368 (2004)), presumably reflecting the explosive release of large amounts of $H_2S$ from NaHS. The slower release of $H_2S$ from GYY4137 leading to lower local concentrations of this gas may explain the lack of a direct effect of GYY4137 on cardiac contractility.

Bolus (intravenous) injection of GYY4137 had no immediate effect on blood pressure in the anesthetized rat but caused a slow fall in blood pressure for up to 2 hours accompanied by a progressive, presumably reflex rise in heart rate. In vivo, GYY4137 was ≈15 times less effective than NaHS as a vasodepressor, but the action was considerably more prolonged (i.e., 120 minutes versus 15 to 30 seconds). In addition, GYY4137 did not affect the vasodepressor response to sodium nitroprusside, implying no direct interference with the action of NO. PNU37883A reduced the vasodepressor effect of both GYY4137 and NaHS, suggesting that, in vivo as well as in vitro, the vasorelaxant effect of this agent occurs largely by opening vascular $K_{ATP}$ channels.

To determine whether the vasodepressor activity of GYY4137 in anesthetized rats translates into an antihypertensive effect, it was further observed that (1) acute GYY4137(but not NaHS) administration reduced the hypertensive effect of L-NAME in the anesthetized rat and (2) chronic GYY4137 administration reversibly decreased systolic blood pressure of both conscious SHR and normotensive WKY rats. This effect occurred within 2 days of starting treatment, and blood pressure of treated animals remained lower for the full 14 days. Thereafter, blood pressure slowly returned to normal, with significant hypotension (in SHR) still present 7 days after the last injection. After 14 days without treatment, blood pressure of SHR and WKY rats had normalized, with no rebound rise detected. The persistent hypotension of SHR after cessation of drug treatment suggests that GYY4137 produces longer-term changes in blood pressure control. Animals tolerated daily injection of GYY4137 well throughout the treatment period, with normal weight gain and no overt signs of toxicity. The present results show clearly that GYY4137 exerts a significant antihypertensive effect both acutely and after chronic administration.

In conclusion, described herein is the utilization of GYY4137 as a tool to further investigate the cardiovascular significance of $H_2S$. In particular, shown herein is that (1) exposing vascular smooth muscle cells to low concentrations of $H_2S$ over a prolonged period does not cause cell toxicity/apoptosis, which is in contrast to the effect of large quantities of $H_2S$ generated from NaHS; (2) low concentrations of $H_2S$, unlike NaHS, do not have any direct effect on cardiac rate/force of contraction in the isolated rat heart; (3) isolated blood vessels respond to the presence of low concentrations of $H_2S$ with a slowly developing but sustained vasorelaxation as opposed to the rapid and transient effect of NaHS on these blood vessels; (4) low quantities of $H_2S$ reduce the hypertensive effect of L-NAME in anesthetized rats (an effect not shared by NaHS); and (5) chronic treatment of SHR with GYY4137 causes a sustained fall in blood pressure. GYY4137 is a useful tool to probe the biological significance of $H_2S$ in cardiovascular and other systems and has therapeutic applications in cardiovascular disease.

Example 3

GYY4137, a Hydrogen Sulfide Releasing Molecule, Protects Against Endotoxic Shock in the Rat Hydrogen sulfide ($H_2S$) is formed from L-cysteine largely by the pyridoxal 5' phosphate-dependent enzymes, cystathionine γ lyase (CSE) and cystathionine β synthetase. $H_2S$ biosynthesis has been identified in a variety of mammalian tissues (e.g. lung, liver, stomach, colon, pancreas, brain) as well as in isolated vascular smooth muscle cells, acinar cells and neurons (Stipanuk, M. H. Ann. Rev. Nutr. 24:539-577 (2004)). Recently, $Ca^{2+}$/calmodulin-dependent $H_2S$ biosynthesis has also been recognised in vascular endothelial cells and $H_2S$ has been proposed to act as an additional endothelium-derived relaxing factor (Yang, G., et al., Science 322: 587-590 (2008)).

Over the last few years a number of potential physiological and pathophysiological roles for this gas have been proposed (for reviews, see Li, L. and Moore, P. K., Trends in Pharmacol. Sci, 28:84-90 (2008); Szabo, C., Nat. Rev. Drug Discov., 6:917-935 (2007)) and it is becoming increasingly clear that $H_2S$ is likely to have a role to play in mammalian biology alongside, and perhaps interacting with, other endogenous gases such as nitric oxide (NO) and carbon monoxide (CO). Possibly one of the most controversial areas of $H_2S$ biology at present is its role in inflammation (for review, see Wallace, J., Trends Pharmacol. Sci. 28:501-505 (2007)). Numerous conflicting data relating to the pro- and/or anti-inflammatory profile of activity of exogenous/endogenous $H_2S$ have been reported. For example, sodium hydrosulfide (NaHS), an $H_2S$ 'donor', has been reported both to dilate (Zhao, W., et al., EMBO J. 20:6008-6016 (2001))) and to constrict (Olson, K. R., et al., J. Exp. Biol. 209:4011-4023 (2006)) blood vessels, promote (Zhang, H., et al., J. Leukoc. Biol. 82:894-905 (2007); Dal-Secco, D., et al., J. Immunol. 181:4287-4298 (2008)) or decrease (Zanardo, R. C., et al., FASEB J. 20:2118-2120 (2006)) leukocyte/endothelium adhesion either by upregulating (Zhang, H., et al., J. Leukoc. Biol. 82:894-905 (2007); Dal-Secco, D., et al., J. Immunol. 181:4287-4298 (2008)) or downregulating (Zanardo, R. C., et al., FASEB J. 20:2118-2120 (2006); Fiorucci, S., et al., Gastroenterology 129:1210-1224 (2005)) ICAM-1 expression and to augment (Kawabata, A., et al., Pain 132:74-81 (2007)) or inhibit (Distrutti, E., et al., J. Pharmacol. Exp. Ther. 316:325-335 (2005)) pain perception. Moreover, both $H_2S$ donors (Li, L., et al., Free Radical Biology and Medicine, 42:706-719 (2006)) and CSE inhibitors (Bhatia, M., et al., FASEB J. 19:623-625 (2004); Collin, M., Br. J. Pharmacol. 146:498-505 (2005); Mok, Y. Y. P., et al., Br. J. Pharmacol. 143:881-889 (2004)) exhibit anti-inflammatory activity in a range of animal models of inflammation. An additional complicating factor in understanding the part played by H2S in inflammation is the ability of this gas to affect the bioavailability of NO which also plays a key part in inflammation. $H_2S$ can interact with NO in a number of ways including a direct chemical reaction to form a nitrosothiol (Yusuf, M., et al., Br. J. Pharmacol. 149:625-634 (2006)), inhibition of nitric oxide synthase (Kubo, S., et al., Toxicology 232:138-146 (2007)) and byquenching reactive oxygen species (Whiteman, M, et al., J. Neurochem. 90:765-768 (2004)).

Much of the current knowledge of the biology of $H_2S$ stems from the use of inhibitors of CSE such as DL-propargylglycine (PAG). However, PAG (and like drugs) target the pyridoxal 5' phosphate binding site of this enzyme and, as such, may affect other pyridoxal 5' phosphate-dependent enzymes as well. Recently, considerable emphasis has also been place on the use of NaHS as a 'tool' to model the biological effects of endogenous $H_2S$. In aqueous solution, NaHS releases large amounts of $H_2S$ over a period of a few seconds. As such, intact animals or cells exposed to NaHS would be expected to 'experience' very high concentrations of the gas over a very short time frame. Other so-called 'conventional' $H_2S$ donors such as Lawesson's compound and (5-(4-hydroxyphenyl)-3H-1,2-dithiole-3-thione) (Li, L., et al., Free Radical Biology and Medicine, 42:706-719 (2006)) also release $H_2S$ in a similarly explosive burst. Whilst the precise kinetic profile of endogenous $H_2S$ release within individual tissues has yet to be evaluated, it seems likely that cells will naturally be exposed to much lower concentrations of the gas but over longer time periods. It might therefore be argued that, depending on dose/concentration used, NaHS more closely mimics the toxic (c.f. the physiological) effects of $H_2S$. Indeed, some reports using NaHS as $H_2S$ donor agent suggest that the vasorelaxant effect of this gas in aortic rings in vitro may be secondary to effects on ATP generation (i.e. metabolic inhibition, Kiss, L., et al., Life Sci, 24:589-594 (2008)) or to changes in vascular smooth muscle intracellular pH (Lee, S. W., et al., Biochem Biophys Res Commun. 358:1142-1147 (2007)).

As shown in Example 2, GYY4137 (morpholin-4-ium 4 methoxyphenyl (morpholino)phosphinodithioate releases $H_2S$ slowly both in aqueous solution in vitro and following administration to the anaesthetized rat in vivo (Li, L., et al., Circulation 117:2351-2360 (2008) which is incorporated herein by reference in its entirety). Release of H2S from GYY4137 in aqueous solution was found to be pH-dependent with considerably greater release at pH 3.0 than at neutral or alkaline pH (Li, L., et al., Circulation 117:2351-2360 (2008) which is incorporated herein by reference in its entirety). At this stage, it seems likely that the first step of the molecular mechanism of $H_2S$ release from GYY4137 is protonation of the sulfide group to form a sulfhydryl moiety followed by hydrolysis to release $H_2S$. The identity of the other products formed after hydrolysis of GYY4137 is not yet known but, in preliminary experiments, NMR spectroscopy indicates that neither (4-methoxyphenyl)phosphonothioic O,O-acid nor (4-methoxyphenyl)phosphonic acid are produced by this reaction.

As also shown in Example 1, biologically, GYY4137 also causes a slowly developing but long-lasting relaxation of rat aortic rings in vitro and a fall in blood pressure of the rat in vivo (Li, L., et al., Circulation 117:2351-2360 (2008) which is incorporated herein by reference in its entirety). As such, the biological effects of GYY4137 are more likely to correspond to the activity of endogenous $H_2S$ than to the 'conventional' H2S donors used to date. Thus, as described herein, GYY4137 was used to examine further the part played by $H_2S$ in lipopolysaccharide (LPS)-evoked endotoxic shock (a model of systemic inflammation) in the rat.

Materials and Methods

Effect of GYY4137 on LPS-Induced Hypotension in the Anaesthetised Rat

Rats were anaesthetized (i.p.) with a mixture of ketamine (112.5 mg/kg) and xylazine (15 mg/kg) as previously described (Mok, Y.Y. P., et al., Br. J. Pharmacol. 143:881-889 (2004)). Mean arterial blood pressure was recorded from the carotid artery by means of a pressure transducer connected to a PowerLab (AD Instruments Ltd., Australia) running Chart v5. The left femoral vein was cannulated for administration of drugs. LPS (4 mg/kg) was injected intravenously (i.v.) as a bolus (1 ml/kg) followed 10 min later by i.v. administration of either GYY4137 (50 mg/kg) or vehicle (saline, 1 ml/kg). Mean arterial blood pressure was monitored continuously thereafter for a total period of 3 h. Results are shown as change in mean arterial blood pressure and are expressed as mm Hg.

Effect of GYY4137 on LPS-Induced Endotoxic Shock in the Conscious Rat

Male Sprague-Dawley rats (230-270 g) were maintained in the Animal Housing Unit in an environment with controlled temperature (21-24° C.) and lighting (12:12 h lightdarkness cycle). Standard laboratory chow and drinking water were provided ad libitum. A period of three days was allowed for animals to acclimatize before any experimental manipulations were undertaken. Bacterial endotoxin LPS (E. coli, serotype O127:B8; 4 mg/kg, ip) was administered to conscious rats. Control animals received saline (1 ml/kg, ip). GYY4137 (50 mg/kg, i.p.) or saline was administered either 1 h before (i.e. 'prophylactic'), or 1 h or 2 h after (i.e. 'therapeutic') LPS. Animals were killed by overdose of anesthetic (3 ml/kg, ip, of a mixture containing ketamine, 24% v/v, and medetomidine, 16% v/v) 4 h after LPS or saline injection and blood was removed by cardiac puncture into heparinized (50 units/ml) tubes. Plasma was stored at −80° C. until required and then thawed and used for biochemical assays as described below. Lungs and livers were also removed and sections subjected to histological examination as described below. Myeloperoxidase activity was also measured in lung homogenates. In some experiments, a solution of GYY4137 (7 mg/ml) was prepared in saline and left unstoppered at room temperature for 72 h. The anti-inflammatory effect of this 'decomposed GYY4137' was compared with that of GYY4137 (both 50 mg/kg, i.p.) following administration to conscious rats 1 h after LPS injection as described above. Lung myeloperoxidase activity and plasma TNF-α concentration were thereafter determined 4 h after LPS injection as described below.

Effect of GYY4137 on LPS Challenged-Rat Blood and RAW 264.7 Cells In Vitro

Blood (5-7 ml) was obtained by cardiac puncture from anesthetised rats. LPS-induced TNF-α formation in whole rat blood was determined as reported previously (Marshall, M., et al., Eur. J. Pharmacol. 483:317-322 (2004)). Blood was immediately anticoagulated with heparin (50 U/ml) and incubated (37° C., 1 h) with LPS (50 ng/ml) in the presence and absence of GYY4137 (10-1000 μM). After incubation, blood incubates were rapidly centrifuged (1000 g, 10 min) and aliquots of the resulting plasma assayed for the presence of TNF-α by ELISA as described below.

In separate experiments, mouse RAW 264.7 macrophages were cultured in complete Dulbecco's Modified Eagle Medium (containing 10% v/v fetal bovine serum, 100 U/ml penicillin and 100 mg/ml streptomycin, pH 7.4) at 37° C. in 5% $CO_2$ until about 70-80% confluence. Cells ($0.2 \times 10^6$ cells/ml) were then cultured overnight prior to the addition of GYY4137 (100 μM) or an appropriate volume of vehicle as well as LPS (1 μg/ml). After a further 24 h incubation period, NO production was determined by measurement of nitrate/nitrite levels in cell culture media by the Griess reaction as described below. $PGE_2$ production was determined using a $PGE_2$ enzyme immunoassay kit according to the manufacturer's instructions (Cayman, Mich., USA). In separate experiments, Western blot analysis was employed to determine the effect of GYY4137 (100 and 500 μM) on LPS-evoked changes in inducible nitric oxide synthase and cyclooxygenase-2 expression in RAE 264.7 macrophages as described previously [14]. In brief, 20-30 μg of protein was subjected to a 7.5-10% SDS gel. Following electrophoresis, the protein was transferred to a nitrocellulose membrane at 4° C. and subsequently hybridized with the appropriate primary antibody (Santa Cruz Biotech, Santa Cruz, Calif., USA) and β-actin (Sigma-Aldrich, Poole, Dorset, UK) as control. After incubation with the primary antibodies, membranes were washed and incubated with the respective secondary antibodies. Blots were visualized using SuperSignal West Dura Kit according to the manufacturer's protocol (Pierce, USA) on a Kodak ScientiWc Imaging system (Kodak, Conn., USA). NF-κB in nuclear extracts was assayed as described below.

Assay of Rat Lung Myeloperoxidase Activity

Neutrophil sequestration in lungs from GYY4137- and vehicle-treated rats subjected to LPS-induced endotoxic shock was quantified by measuring tissue myeloperoxidase activity as described elsewhere (Li, L., et al., FASEB J. 19:1196-1198 (2005)). Tissue samples were washed thoroughly in saline, homogenized in 20 mM phosphate buffer (pH 7.4), centrifuged (10,000 g, 10 min, 4° C.), and the resulting pellet resuspended in 50 mM phosphate buffer (pH 6.0) containing 0.5% v/v hexadecyltrimethylammonium bromide. The suspension was subjected to four cycles of freezing and thawing and further disrupted by sonication (40 s). Samples were then centrifuged (10,000 g, 5 min, 4° C.) and the supernatant used for the myeloperoxidase assay. The reaction mixture consisted of tissue supernatant (50 µl), tetramethylbenzidine (1.6 mM), sodium phosphate buffer (80 mM, pH 5.4) and hydrogen peroxide (0.3 mM). The total incubation volume was 100 µl. Incubations were conducted at 37° C. for 110 s, after which the reaction was terminated with 0.18 M $H_2SO_4$ (50 µl) and absorbance (405 nm) determined. Tissue myeloperoxidase activity was normalised for DNA concentration, which was determined spectrofluorimetrically according to a previously published procedure (Labarca, C. Paigen, K., Anal. Biochem. 102:344-352 (1980)). Results were calculated as myeloperoxidase activity per microgram of DNA and are shown as percentage increase over control.

Assay of Plasma Nitrite/Nitrate, IL-1β, TNF-α, IL-6, IL-10, L-Selectin and C-Reactive Protein, Amylase, Creatinine, Alanine Aminotransferase Nitrite/nitrate was determined spectrophotometrically in aliquots (80 µl) of plasma using the Griess reagent as described elsewhere (Li, L., et al., FASEB J. 19:1196-1198 (2005)). Plasma was centrifuged (14,000 g, 25 min, 4° C.) and filtered, and aliquots (80 µl) incubated (37° C., 30 min) in duplicate in 96-well plates with nitrate reductase (10 mU) in the presence of NADPH (100 µM) to reduce nitrate to nitrite. Thereafter, Griess reagent (containing 0.1% w/v N-(1-napthyl)ethylenediamine dihydrochloride and 1% w/v sulfanilamide in 5% v/v $H_3PO_4$) was added into the above mixture in a ratio of 1/1 (v/v) and incubated for 10 min at room temperature after which absorbance was determined at 550 nm in a 96-well microplate reader (Tecan Systems, Inc.). The concentration of nitrite (indicative of nitrate/nitrite in the original samples) was calculated from a standard curve of $NaNO_2$ (0.125-75 µM) and expressed as µM nitrite. Plasma IL-1β, TNF-α, IL-6, IL-10, L-selectin (R&D Systems Inc., USA) and C-reactive protein (BD Biosciences, USA) were determined by ELISA using commercially available kits according to the manufacturer's instructions. Plasma amylase, creatinine and alanine aminotransferase were measured using commercially available kits (Teco Diagnostics, USA). Amylase assay was based on the use of p-nitrophenyl D-maltoheptaoside as substrate, creatinine was measured by reaction with alkaline picrate (Jaffe reaction) and alanine aminotransferase by a kinetic method based on the oxidation of NADH by lactate dehydrogenase.

Assay of Liver NF-kB, AP-1 and STAT-3

Livers from GYY4137- and vehicle-injected LPS-treated rats were harvested and the nuclear proteins were extracted using a nuclear extraction kit (Panomics, USA) (Li, L., et al., FASEB J. 19:1196-1198 (2005)). The nuclear extracts (10-20 µg) were assayed in duplicate for activity using TransAM™ NF-κB p65 and AP-1 c-fos assay kits (Active Motif) according to the manufacturer's instructions. STAT-3 was assayed using a TransFactor Universal STAT-3 specific kit (Clontech, USA). The $OD_{450}$ or $OD_{655}$ (for STAT-3) was read on a 96-well microplate reader (Tecan System Inc.).

Histological Examination

Lung and liver segments (approx. 100 mg) were fixed in 10% v/v phosphate-buffered formalin (pH 7.4) for 24 h and then embedded in paraffin as described previously (Li, L., et al., Free Radical Biology and Medicine, 42:706-719 (2006)). Sections (4 µm) were cut using a microtome, stained with hematoxylin and eosin (H&E) and viewed by light microscopy at ×400 magnification.

Statistics

Data show mean±SEM with the number of observations indicated in parentheses. Statistical analysis was by one-way ANOVA followed by post hoc Tukey test. A P value of <0.05 was taken to indicate a statistically significant difference.

Results

Effect of GYY4137 on LPS-Induced Hypotension in the Anaesthetised Rat

Figure 9:
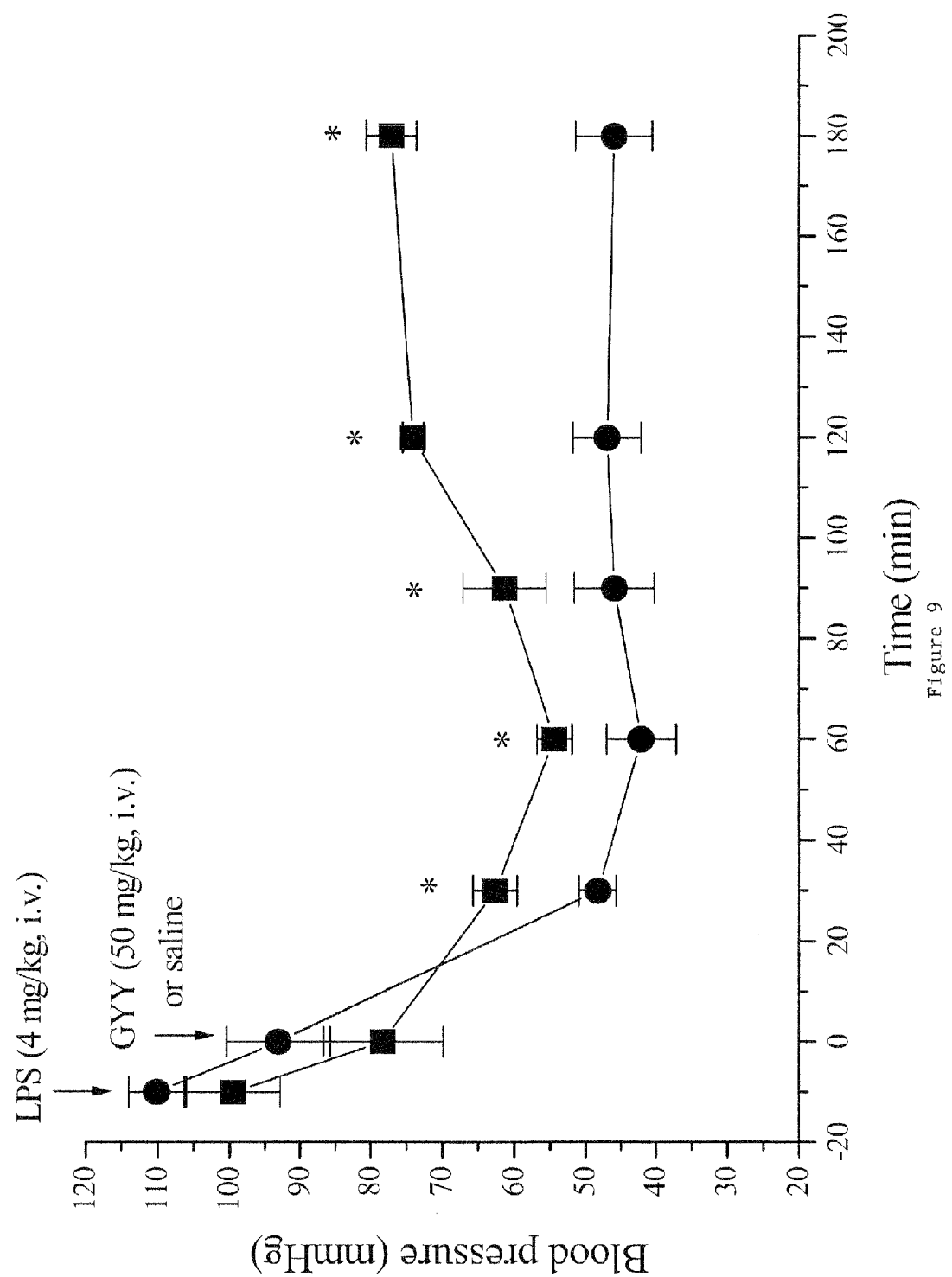
FIG. 9 is a graph of the effect of GYY4137 (50 mg/kg, i.v.) administered 10 min after LPS (4 mg/kg, i.v.) on mean arterial blood pressure in anesthetized rats. Data shows time course of LPS effect and is mean±s.e. mean, n=5, *P<0.05 c.f. LPS+saline.

Administration of LPS to anaesthetised rats resulted in a slowly developing fall in blood pressure which peaked at 60 min and then plateaued over the following 120 min. GYY4137 (50 mg/kg) but not vehicle (saline) injected 10 min after LPS significantly reversed the hypotensive effect of LPS at all time points from 30 min to 180 min (FIG. 9). At the end of the experiment, blood pressure of GYY4137-treated animals was about 40 mm Hg greater than that of control animals which approximates to a reversal of the LPS-evoked hypotension of about 65%.

Effect of GYY4137 on LPS-Induced TNF-α Formation in Rat Blood In Vitro

Figure 10:
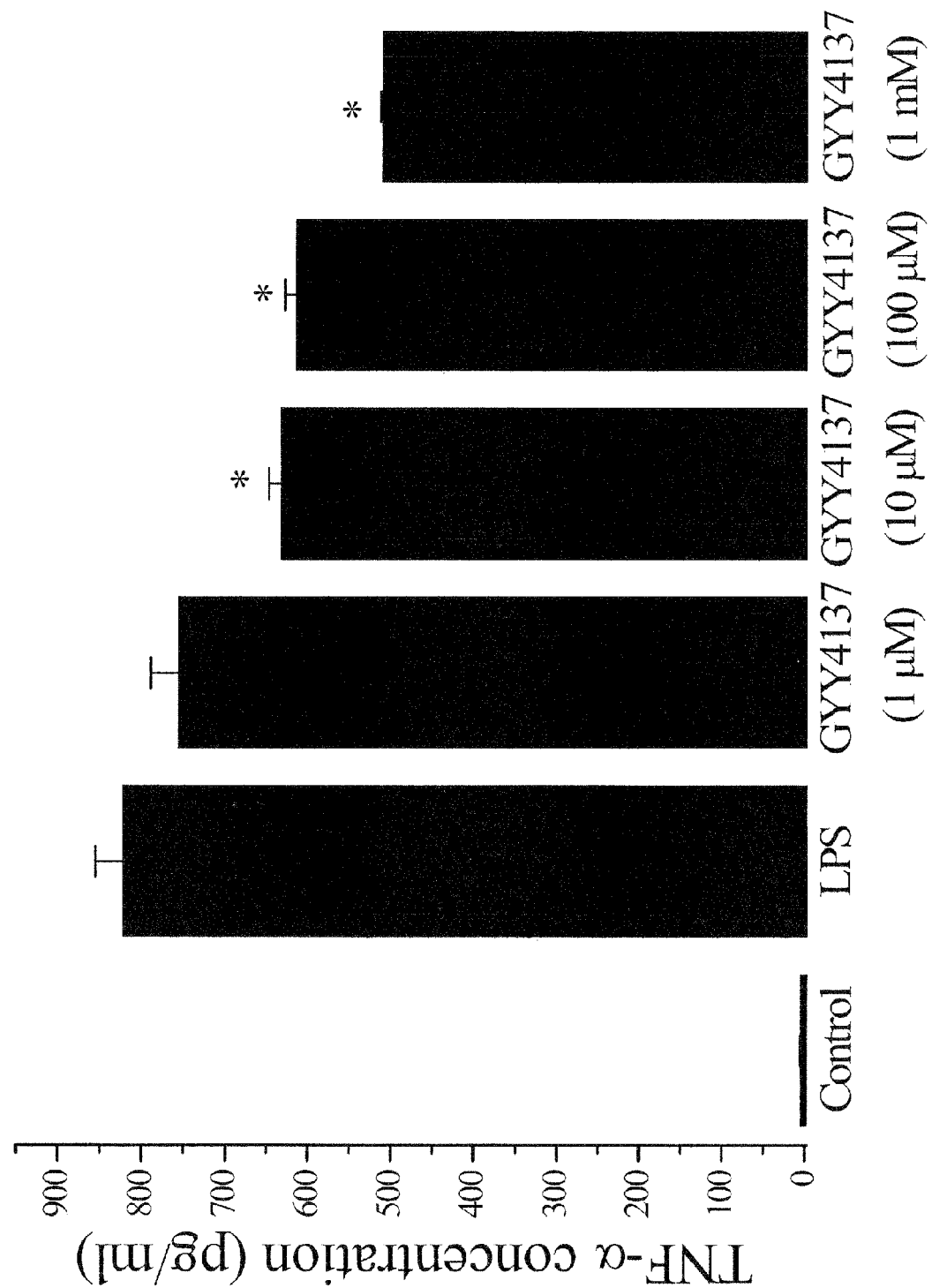
FIG. 10 is a graph of the effect of GYY4137 on LPS (50 ng/ml) induced TNF-α formation in incubated (37° C., 1 h) rat whole blood. No TNF-□α was detected in non-incubated rat whole blood. Results show mean±s.e. mean, n=4-7, *P<0.05 c.f. LPS alone.

Prior to examining the ability of GYY4137 to affect LPS-evoked inflammation in the rat in vivo, preliminary experiments were carried out to monitor the effect of this $H_2S$ donor on LPS-induced TNF-α secretion in rat blood and cultured macrophages in vitro. As expected, incubation of rat blood with LPS resulted in the formation of large amounts of TNF-α (822.1±32.8 pg/ml, n=7). Preincubation of rat blood with GYY4137 (10-1000 µM) concentration-dependently decreased the LPS-evoked increase in TNF-α concentration in these experiments (FIG. 10). For example, at the highest concentration used, GYY4137 (1 mM) inhibited LPS-evoked TNF-α formation in rat blood by 37.1±0.3% (n=4).

Effect of GYY4137 on LPS-Induced Inducible Nitric Oxide Synthase/Cyclooxygenase-2 Expression, Nitrite/Nitrate, $PGE_2$ Formation and NF-kB Expression in Cultured RAW 264.7 Cells In Vitro LPS challenge of RAW 264.7 cells in culture significantly increased inducible nitric oxide synthase and cyclooxygenase-2 expression (FIG. 11A), NF-κB activation (FIG. 11B), the biosynthesis of nitrite/nitrate (FIG. 11C) and $PGE_2$ (FIG. 11D) as well as the generation of TNF-α (FIG. 11E). As noted in rat blood, GYY4137 decreased the LPS-evoked rise in TNF-α (FIG. 11E). Interestingly, co-culture of RAW 264.7 cells in the presence of GYY4137 significantly decreased the LPS-evoked increase in NF-κB activation (FIG. 11B), nitrite/nitrate (FIG. 11C) and $PGE_2$ (FIG. 11D).

Figure 14A:
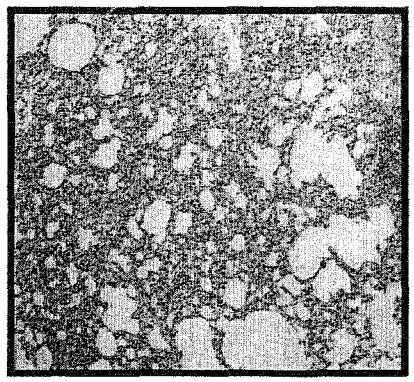
Figure 14B:
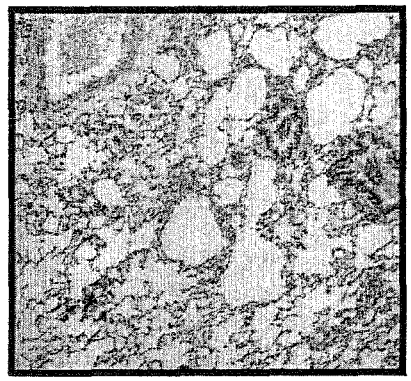
Figure 14C:
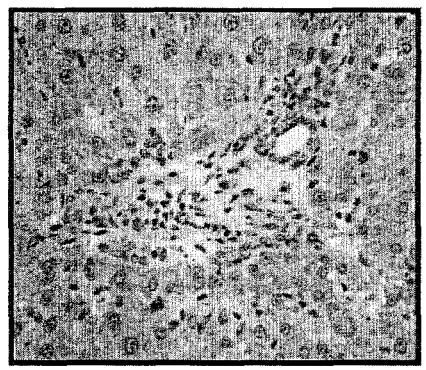
Figure 14D:
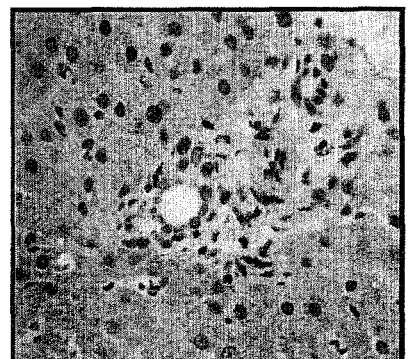
Figure 14E:
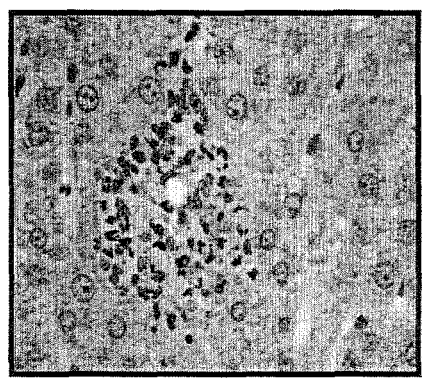

Effect of GYY4137 on Metabolic Markers of LPS-Induced Endotoxic Shock in the Rat LPS administration to conscious rats resulted in systemic inflammation as evidenced by significant increases in plasma cytokines (TNF-α, IL-1β, IL-6, IL-10) (FIGS. 12A-12D), nitrite/nitrate, C-reactive protein and L-selectin as well as elevated lung myeloperoxidase activity (FIGS. 13A-13D). Histological examination of lungs from LPS-treated rats also revealed features of inflammatory damage including mild interstitial edema and significant alveolar thickening due to the presence of numerous leukocytes (lymphocytes and neutrophils) (FIGS. 14A, 14B). Histological changes in livers from LPS-treated animals was also apparent in the form of portal tract inflammation and scattered chronic/active lobulitis (FIGS. 14C, 14D). Evidence of a state of endotoxic shock in these animals was also indicated by the presence of significantly raised plasma concentrations of creatinine and plasma alanine aminotransferase and amylase activity suggestive of the existence of kidney, liver and pancreas damage respectively (FIGS. 15A-15C).

Administration of GYY4137 1 h prior to LPS injection did not affect lung myeloperoxidase activity or alter the LPS-induced rise in plasma nitrite/nitrate, TNF-α, IL-1β, IL-6, IL-10, L-selectin, creatinine or amylase activity (FIGS. 12A-12D, 13A-13D, 15A-15C). However, 'prophylactic' administration of GYY4137 in this way did decrease plasma C-reactive protein concentration and plasma alanine aminotransferase activity (FIGS. 13A-13D and 15A-15C). Moreover, histological examination of lung and liver from such treated animals revealed no significant changes compared with tissues from LPS-treated animals (data not shown). Thus, overall, administration of GYY4137 as a pretreatment before LPS injection did not result in a significant anti-inflammatory effect.

Figure 14F:
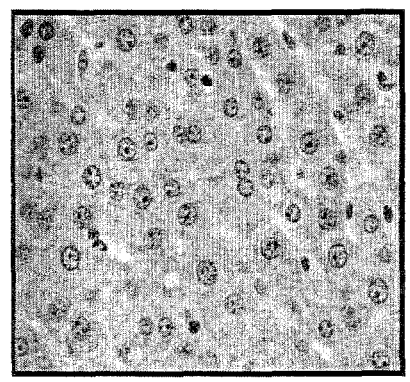

In contrast, administration of GYY4137 either 1 h or 2 h after LPS injection (i.e. post-treatment) decreased the LPS-evoked rise in plasma nitrite/nitrate, TNF-α, IL-1β, C-reactive protein, creatinine and alanine aminotransferase whilst 1 h (but not 2 h) posttreatment was also effective in reducing the LPS-evoked rise in plasma IL-6, IL-10 and L-selectin. Plasma amylase activity was unaffected by the administration of GYY4137 using any dose regimen (FIGS. 12A-12D, 13A-13D, 15A-15C). Histologically, both liver and lung from animals treated with GYY4137 1 h or 2 h LPS injection showed signs of inflammatory damage although in both cases this was less apparent than in animals administered LPS alone (FIGS. 14B, 14D, 14F).

The anti-inflammatory effect of 'decomposed GYY4137' was compared with that of GYY4137 in a separate series of experiments. In these animals, post-treatment (1 h) of animals with GYY4137 again decreased the LPS-evoked rise in lung myeloperoxidase activity and decreased the resulting rise in plasma TNF-α concentration. Interestingly, 'decomposed GYY4137' at the same dose and over the same time course had no effect on the ability of LPS to increase either lung myeloperoxidase activity or plasma TNF-α concentration in these animals (FIGS. 16A-16C).

Effect of GYY4137 on Rat Liver Transcription Factor Activation in the Rat

In an attempt to gain additional insight into the mechanisms underlying the effect of GYY4137 on LPS-induced upregulation of the above-mentioned markers of inflammation, further experiments were carried out to investigate its action on a range of intracellular transcription pathways known to play a part in the induction of these enzymes and in the formation of cytokines. In these experiments, administration of LPS resulted in a marked increase in NF-κB, AP-1/c-fos and STAT-3 activation in liver (FIGS. 17A-17C). Pretreatment of LPS-injected animals with GYY4137 significantly decreased NF-κB but had no effect on the other transcription factors. Administration of GYY4137 either 1 h or 2 h after LPS injection also decreased NF-κB activation although STAT-3 activation was augmented when GYY4137 was injected 1 h after LPS. Interestingly, GYY4137 did not affect rat liver AP-1 activation administered either before or after LPS (FIGS. 17A-17C).

Discussion

GYY4137 Partially Restores Blood Pressure in Endotoxic Shock

Endotoxic shock both in man and in animals is associated with slowly developing hypotension along with diminished blood vessel responsiveness to vasoconstrictor drugs and progressive organ hypoperfusion and dysfunction (Trzeciak, S., et al., Intensive Care Med. 34:2210-2217 (2008)). The metabolic changes which occur in endotoxic shock are widespread and complex but a major feature is known to be increased biosynthesis of vasodilator NO and prostanoids following upregulation of the cellular expression of inducible nitric oxide synthase and cyclooxygenase-2 respectively. In the present experiments, GYY4137 partially reversed the LPS-induced hypotension in anaesthetized rats.

The mechanism of action is unlikely to be due to a direct effect on the vasculature since we have previously reported that, in both normotensive and hypertensive rats, GYY4137 causes a slowly developing, modest fall (not rise) in blood pressure due to activation of vascular KATP channels by the released $H_2S$ (Li, L., et al., Circulation 117:2351-2360 (2008)). The mechanism(s) underlying the ability of GYY4137 to increase blood pressure in LPS-injected rats in the present study are likely to be complex. For example, it is possible that $H_2S$, released from GYY4137, reacts chemically with and thereby quenches vasodilator NO. Indeed, we have previously reported such an interaction between $H_2S$ (derived from NaHS) and NO (derived from sodium nitroprusside both in vitro (rat aortic ring) and in vivo (anaesthetized rat) (18). Such an interaction might be expected to increase blood pressure since NO is synthesized in large amounts by inducible nitric oxide synthase in such LPSPK-injected animals. However, we have previously reported that GYY4137 administration does not affect the vasodepressor response to sodium nitroprusside in anaesthetized rats presumably because the low amounts of $H_2S$ generated are insufficient to quench the NO present (Li, L., et al., Circulation 117:2351-2360 (2008)). Accordingly, direct quenching of excessive NO by GYY4137-derived $H_2S$ seems unlikely to account for its ability to partially reverse the LPS-induced hypotension in the present experiments. As an additional possibility, recent work has suggested that low concentrations of $H_2S$ increases $O_2$ consumption in mammalian blood vessels most likely by feeding electrons to the electron transport chain (Koenitzer, J. R., et al., Am. J. Physiol. 292:H1953-1960 (2007)). Since endotoxic shock is associated with a decline in $O_2$ utilization it is conceivable that such an effect may also contribute to the beneficial effect of GYY4137 in this condition. However, the precise effect of $H_2S$ on mitochondrial function is complex since this gas can act both as a substrate and an as inhibitor of cyctochrome oxidase (Nicholls, P., et al., Can. J. Biochem. 60:613-623 (1982)) and its effect and potency appears to be dependent to some extent on the degree of cellular integrity (e.g. Leschelle, X, et al., Biochem. Biophys. Acta 1725:201-212 (2005)). Whether an action on mitochondrial function underscores the beneficial effect of GYY4137 in the present experiments therefore requires further study.

Alternatively, GYY4137 may decrease tissue inducible nitric oxide synthase/cyclooxygenase-2 expression resulting in a fall in vasodilator 'drive' generated by both NO and prostanoids. Indeed, subsequent work both in LPS-exposed RAW 264.7 cells and in LPS-treated conscious rats (discussed below) adds weight to this possibility and suggests that the main cellular target for $H_2S$ in endotoxic shock is likely to be transduction of key pro-inflammatory enzymes/molecules by inhibiting the NF-κB pathway.

GYY4137 Inhibits Organ Dysfunction in Endotoxic Shock

In addition, to hypotension, LPS injection also significantly elevated plasma creatinine concentration and alanine aminotransferase activity but did not affect plasma amylase activity. The absolute rise in plasma creatinine/alanine aminotransferase observed in the present experiments is modest compared with other published reports (e.g. Collin, M., et al., J. Leukoc. Biol. 76:961-970 (2004)) most probably because we used less LPS (4 mg/kg c.f. 6 mg/kg) and a shorter time period of exposure (4 h c.f. 6 h). The shorter exposure period may also explain the lack of effect of LPS on plasma amylase activity which occurs later in the disease process. Nevertheless, we show here that GYY4137 decreased the LPS-induced rise in plasma alanine aminotransferase/creatinine suggesting a protective role for this compound in endotoxin-mediated liver and kidney dysfunction. The present data therefore supports previous recent reports in the literature indicating that $H_2S$ can be protective in endotoxic shock/organ dysfunction. For example, S-diclofenac administration decreased inflammation in LPS-injected rats (Li, L., et al., Free Radical Biology and Medicine, 42:706-719 (2006)), both endogenously generated and exogenously $H_2S$ protect the kidney against ischemia-reperfusion injury in vitro (Tripatara, P., et al., Lab. Invest. 88:1038-1048 (2008)) and sodium sulfide both attenuated reperfusion-induced hyperlactemia and improved vascular norepineprine-mediated vasoconstriction in anesthetized pigs following aortic occlusion (Simon, F., et al., Shock, 30:359-364 (2008)).

Anti-Inflammatory Effect of GYY4137 in Endotoxic Shock

In preliminary experiments, it was first noted that GYY4137 caused a concentration-related inhibition of LPS-induced TNF-α generation both in rat blood and cultured RAW 264.7 cells in vitro. The source of TNF-α in rat blood is likely to be blood-borne leukocytes (Marshall, M., et al., Eur. J. Pharmacol. 483:317-322 (2004)). The concentration/inhibition relationship in rat blood was shallow but even so it was interesting to note that even at a low concentration (10 μM) GYY4137 significantly inhibited TNF-α formation. GYY4137 (100 μM) also inhibited LPS-induced TNF-α formation from RAW 264.7 cells by approximately 40%. Since $H_2S$ release from GYY4137 is a slow process both in vitro and in vivo and, furthermore, any released $H_2S$ might be expected to be quickly broken down and/or bind rapidly to blood constituents it would appear that the gas may be a relatively potent inhibitor of TNF-α formation in these experiments. It was also reported that, in LPS-challenged RAW 264.7 cells, GYY4137 decreased the LPS-evoked activation of NF-κB, expression of inducible nitric oxide synthase and cyclooxygenase-2 enzymes and the consequent biosynthesis of nitrite/nitrate and $PGE_2$. As discussed later, a similar effect on NF-κB activation was detected in liver homogenates prepared from GYY4137-treated animals. Taken together these data raise the possibility that GYY4137 is anti-inflammatory effect in vivo by decreasing NF-κB transduction thereby inhibiting inducible nitric oxide synthase/cyclooxygenase-2 expression and decreasing the biosynthesis, not only of proinflammatory cytokines, but also of other pro-inflammatory mediators such as NO and prostanoids. It seems likely that this mechanism also contributes to the ability of GYY4137 to increase blood pressure of LPS-treated animals.

With these isolated cell experiments in mind, the effect of GYY4137 on the production of cytokines and other inflammatory molecules was examined in vivo. GYY4137 also exhibited anti-inflammatory activity in a model of endotoxic shock in the conscious rat as evidenced by its ability to inhibit the LPS-induced, (i) rise in lung myeloperoxidase activity (indicative of tissue neutrophil infiltration), (ii) increase in plasma pro-inflammatory cytokine (TNF-α, IL-1β and IL-6), nitrite/nitrate, C-reactive protein and L-selectin concentration and, (iii) lung and liver damage (assessed histologically). Intriguingly, GYY4137 also increased plasma concentration of the antiinflammatory cytokine, IL-10, in these animals. Clearly, such a spectrum of biological effects strongly suggests an anti-inflammatory profile of activity for GYY4137 which underscores the effectiveness of this compound in reducing the symptoms of endotoxic shock. In separate experiments, the effect of 'decomposed GYY4137' (i.e. GYY4137 which had been left at room temperature for 72 h to decompose and release its $H_2S$) was examined. Interestingly, such 'time expired' GYY4137 did not exhibit anti-inflammatory thus providing evidence that the effect of authentic (i.e. fresh) GYY4137 on LPS-evoked inflammation observed in this study was indeed secondary to $H_2S$ generation. Further work to establish the role of $H_2S$ in the effect of GYY4137 might perhaps include the use of $H_2S$ quenching agents. However, selective $H_2S$ quenching agents are, as yet, not available. Whilst both hemoglobin and myoglobin bind $H_2S$, they also bind both nitric oxide and carbon monoxide and as such are not selective.

A somewhat unexpected finding is that the anti-inflammatory effect of GYY4137 in endotoxic shock is dependent on the timing of its injection relative to LPS. Thus, little or no evidence of an anti-inflammatory effect was apparent when GYY4137 was injected 1 h before LPS but significant activity was detected when the drug was administered either 1 h or 2 h thereafter. One possible explanation for the time-dependent anti-inflammatory effect of GYY4137 may stem from the time course by which it releases $H_2S$ in vivo. GYY4137 administered to rats, at the same dose and route of administration as used in the present study, resulted in peak plasma concentrations of $H_2S$ after 30 min which slowly declined thereafter but remained elevated for a further 150 min thereafter (Li, L., et al., Circulation 117:2351-2360 (2008)). Although not estimated directly, it is likely that a similar time course of plasma $H_2S$ concentration occurred in the present study. Thus it is conceivable that the plasma $H_2S$ concentration following 'prophylactic' administration of GYY4137 may have peaked before LPS was injected. In contrast, plasma $H_2S$ levels would be expected to peak 2 h or 3 h after 'therapeutic' administration of the drug at a time when transcription factor activation (e.g. NF-κB) and consequent upregulation of tissue pro-inflammatory enzymes is taking place. However, it should be noted that little is know about the pharmacokinetic disposition of GYY4137 following injection in the rat. It is, for example, not clear whether this compound is preferentially concentrated in any specific target tissues. If this is indeed the case then it is possible that higher concentrations of $H_2S$ may be generated at such sites. Furthermore, the correlation between plasma $H_2S$ concentrations and the biological effects of GYY4137, and indeed other $H_2S$ donors, is not clear since, (i) rapid catabolism of $H_2S$ is likely in plasma and, (ii) local concentrations of H2S achieved at inflammatory sites may be different.

Mechanism of Anti-Inflammatory Effect of GYY4137

The observation that GYY4137 decreases the LPS-induced rise in a range of different pro-inflammatory cytokines and other molecules in LPS-injected animals points to an effect on those intracellular processes responsible for their biosynthesis. Interestingly, $H_2S$ has previously been reported to affect activation of NF-κB although the results obtained are variable. For example, $H_2S$ inhibited NF-κB activation in LPS-challenged RAW 264.7 macrophages maintained in culture (Oh, G. S., et al., Free Radic. Biol. Med. 41:106-119 (2006)) whilst exposure of rats to gaseous $H_2S$ decreased brain (cortical) NF-κB mRNA (Florian, B., et al., Neurosci Lett. 438:180-185 (2008)) and S-diclofenac administration decreased liver NF-κB activation in LPS-injected animals (Li, L., et al., Free Radical Biology and Medicine, 42:706-719 (2006)). $H_2S$ also decreased kidney NF-κB activation in a rat model of renal ischemia/reperfusion injury (Tripatara, P., et al., Lab. Invest. 88:1038-1048 (2008)). In contrast, NaHS has been shown to activate NF-κB in an interferon-γ (IF-γ primed human monocytic cell line (U937) (Zhi, L., et al. J. Leukoc. Biol. 81:1322-1332 (2007)).

Bearing in mind the ability of GYY4137 to inhibit NF-κB transduction in LPS-challenged RAW 264.7 cells, of particular interested was the evaluation of the effect of GYY4137 treatment on in vivo LPS-mediated changes in transcription factors known to play a part in the inflammatory process. LPS injection resulted 4 h thereafter in increased NF-κB, AP-1 and STAT-3 activation in liver homogenates. GYY4137 decreased the LPS-induced increase in liver NF-κB activation but did not affect LPS-induced upregulation of AP-1. GYY4137 administered 1 h after LPS also increased liver STAT-3 activation. Since activation of NF-κB upregulates production of numerous proinflammatory cytokines growth factors, chemokines, acute phase proteins, adhesion molecules and pro-inflammatory enzymes (e.g. inducible nitric oxide synthase, cyclooxygenase-2, HO-1) (for reviews, see Simmonds, R. E., et al., Rheumatology 47:584-590 (2008); Blackwell, T. S., et al. Am J Respir Crit. Care Med. 162:1095-101 (2000)) it seems reasonable to propose that inhibition of NF-κB activation accounts for the ability of GYY4137 to decrease LPSPK evoked upregulation of cytokines and other pro-inflammatory molecules. Furthermore, since STAT-3 upregulates the secretion of the anti-inflammatory cytokine, IL-10, both in cultured cells (Benkhart, E. M., et al. J. Immunol. 165:1612-1617 (2000)) and in the lungs of LPS-treated rats (Ikegami, M., et al. J. Appl. Physiol. 104:1753-1760 (2008)), it also seems that an effect on STAT-3 underlies the ability of GYY4137 to elevate plasma IL-10 concentration which, in turn, acts to attenuate LPS-induced inflammation. Whilst further experiments are needed it may be the case that at least part of the anti-inflammatory effect of GYY4137 is due to its ability to upregulate IL-10 production. This is the first report of such an effect of $H_2S$ on the STAT-3/IL-10 system.

CONCLUSION

That GYY4137 inhibits LPS-mediated systemic inflammation and endotoxic shock strongly suggests a predominantly anti-inflammatory effect of $H_2S$ under the experimental circumstances used in this model. Other 'slow releasing' $H_2S$ donors such as S-diclofenac and S-mesalamine (Li, L., et al., Free Radical Biology and Medicine, 42:706-719 (2006); Wallace, J. L., et al. Gastroenterology 132:261-271 (2007); Fiorucci, S., et al. Br. J. Pharmacol. 150:996-1002 (2007)) also decrease inflammation in this model. However, this conclusion appears to be at odds with the finding that NaHS augments inflammation and that CSE inhibitors such as PAG are anti-inflammatory (see Introduction for references). However, the data are not necessarily conflicting. $H_2S$ may exert both pro- and anti-inflammatory effects depending upon a variety of factors including the concentration of the gas achieved at the inflamed site. This is not a new concept. It has been known for several years that NO can also exert both pro- and antiinflammatory effects in animal models most likely by a similar mechanism viz. dilatation of blood vessels at high concentrations and inhibition of intracellular NF-κB transduction of pro-inflammatory molecules at low concentrations (Kang, J. L., et al., J Appl Physiol. 92:795-801 (2002); Janssen-Heininger, Y. M., et al. Free Radic Biol Med. 28:1317-1327 (2000)). Thus, it is likely that high concentrations of $H_2S$ (either due to injected NaHS or formed in large amounts during the early stages of tissue inflammation) augment inflammation most likely by dilating blood vessels, promoting edema and triggering hyperalgesia. High concentrations of NaHS therefore mimic this spectrum of pro-inflammatory activity whilst PAG (and other inhibitors of $H_2S$ biosynthesis) will exert anti-inflammatory activity. In contrast, low concentrations of $H_2S$ (either provided by GYY4137 or generated naturally at a later stage in the inflammatory response) are anti-inflammatory by interfering with activation of cellular transductions factors such as NF-κB and also STAT-3 thereby reducing the expression of pro-inflammatory molecules and/or upregulating expression of antiinflammatory molecules.

ABBREVIATIONS

AP-1 activator protein
CSE cystathionine γ lyase
GYY4137 morpholin-4-ium-4-methoxyphenyl(morpholino)phosphinodithioate
H2S hydrogen sulfide
IL-1β interleukin 1β
Il-6 interleukin-6
IL-10 interleukin-10
LPS lipopolysaccharide
NaHS sodium hydrosulfide
NF-κB nuclear factor κB
NO nitric oxide
PAG DL-propargylglycine
STAT-3 signal transduction and activator of transcription-3
TNF-α tumor necrosis factor-α

This application is related U.S. Provisional Application No. 60/936,578, filed on Jun. 21, 2007, entitled "Identification of Morpholin-4-ium 4 Methoxyphenyl (Morphonolino) Phosphinodithioate (GYY4137) as a Novel Vasodilator Agent", which is incorporated by reference in its entirety.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A method of treating a condition associated with constriction of one or more vascular beds in an individual in need thereof comprising administering an effective amount of morpholin-4-ium 4 methoxyphenyl(morpholino)phosphinodithioate (GYY4137) or a pharmaceutically acceptable salt thereof,
wherein the condition is a heart failure.

* * * * *